(12) United States Patent
Burgess et al.

(10) Patent No.: US 11,040,106 B2
(45) Date of Patent: Jun. 22, 2021

(54) CONJUGATES OF KINASE INHIBITORS AND CYANINE DYES

(71) Applicant: Small Molecule PPI Mimics LLC, College Station, TX (US)

(72) Inventors: Kevin Burgess, College Station, TX (US); Syed Muhammad Usama, College Station, TX (US)

(73) Assignee: Small Molecule PPI Mimics LLC, College Station, TX (US)

( * ) Notice: Subject to any disclaimer, the term of this patent is extended or adjusted under 35 U.S.C. 154(b) by 0 days.

(21) Appl. No.: 16/407,264

(22) Filed: May 9, 2019

(65) Prior Publication Data

US 2019/0343958 A1    Nov. 14, 2019

Related U.S. Application Data

(60) Provisional application No. 62/721,451, filed on Aug. 22, 2018, provisional application No. 62/669,792, filed on May 10, 2018.

(51) Int. Cl.
| | | |
|---|---|---|
| A61K 47/54 | (2017.01) | |
| A61K 31/545 | (2006.01) | |
| A61K 31/506 | (2006.01) | |
| A61K 31/519 | (2006.01) | |
| A61K 31/4545 | (2006.01) | |
| C09B 23/01 | (2006.01) | |

(52) U.S. Cl.
CPC ........ *A61K 47/545* (2017.08); *A61K 31/4545* (2013.01); *A61K 31/506* (2013.01); *A61K 31/519* (2013.01); *C09B 23/0083* (2013.01)

(58) Field of Classification Search
CPC .............. A61K 31/4545; A61K 31/506; A61K 31/519; A61K 47/545; C09B 23/0083; C09B 23/0075
USPC ........................................................ 514/264
See application file for complete search history.

(56) References Cited

U.S. PATENT DOCUMENTS

| | | |
|---|---|---|
| 2011/0008597 A1 | 1/2011 | Asai et al. |
| 2015/0183736 A1 | 7/2015 | Chung et al. |
| 2015/0335765 A1 | 11/2015 | Chung et al. |
| 2016/0357901 A1 * | 12/2016 | Burgess .............. C07D 401/14 |
| 2017/0354747 A1 | 12/2017 | Chung et al. |

OTHER PUBLICATIONS

Boobalan et al., Synthesis and biological assay of erlotinib analogues and BSA-conjugated erlotinib analogue. Bioorg Med Chem Lett. 2017;27(8):1784-1788.

* cited by examiner

*Primary Examiner* — Tracy Vivlemore
*Assistant Examiner* — Ebenezer O Sackey
(74) *Attorney, Agent, or Firm* — Wolf, Greenfield & Sacks, P.C.

(57) ABSTRACT

The present disclosure provides conjugates of kinase inhibitors and cyanine dyes, as well as related compositions, methods and uses.

11 Claims, 42 Drawing Sheets

| compound | solvent | $\lambda_{abs}$ (nm) | $\lambda_{em}$ (nm) | $\varepsilon_{max}$ (cm$^{-1}$M$^{-1}$) | $\Delta\lambda$ |
|---|---|---|---|---|---|
| ICG | MeOH | 783 | 817 | 237100 | 34 |
| | PBS | 779 | 807 | 111060 | 28 |
| | H$_2$O | 779 | 811 | 172560 | 32 |
| 1-CH$_2$ | MeOH | 781 | 807 | 232260 | 26 |
| | PBS | 775 | 799 | 149940 | 24 |
| | H$_2$O | 775 | 795 | 57540 | 20 |
| 1-NMe$_2$ | MeOH | 753 | 781 | 233680 | 28 |
| | PBS | 745 | 768 | 192460 | 23 |
| | H$_2$O | 743 | 765 | 152000 | 22 |

| compound | $\varepsilon_{max}$ (cm$^{-1}$M$^{-1}$) | Φ | brightness ($\varepsilon_{max}$ x Φ) |
|---|---|---|---|
| 1-CH$_2$ | 149940 | 0.025 | 3749 |
| 1-NMe$_2$ | 192460 | 0.051 | 9815 |

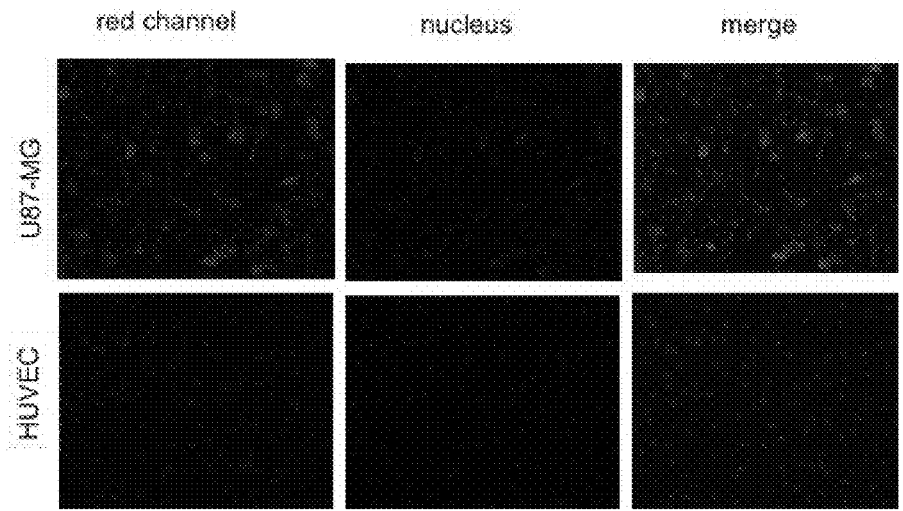
Figure 24 (7)
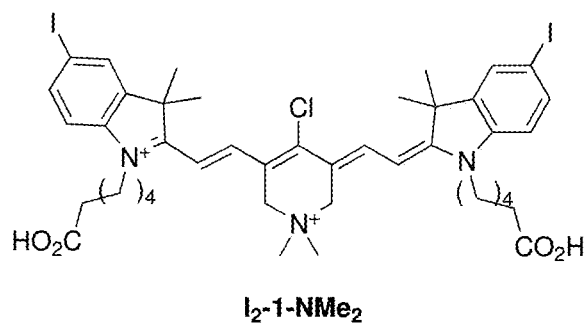
I$_2$-1-NMe$_2$
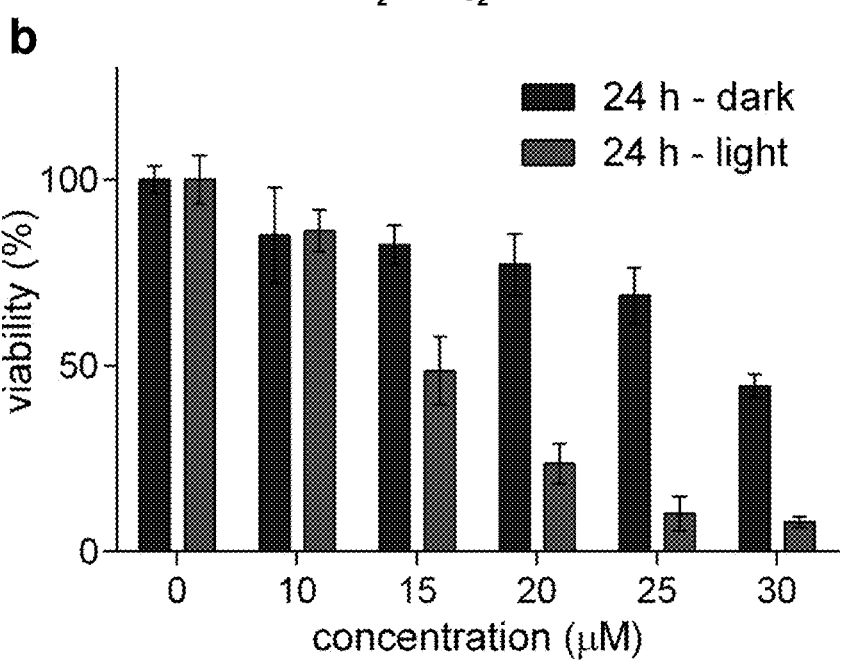
Figure 25

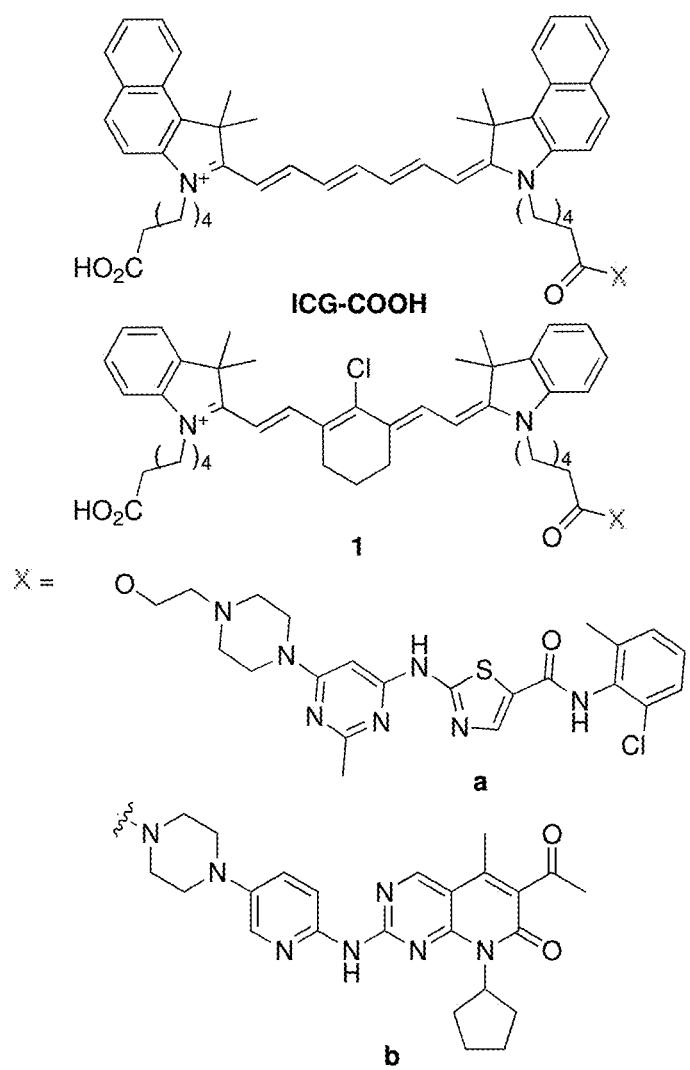
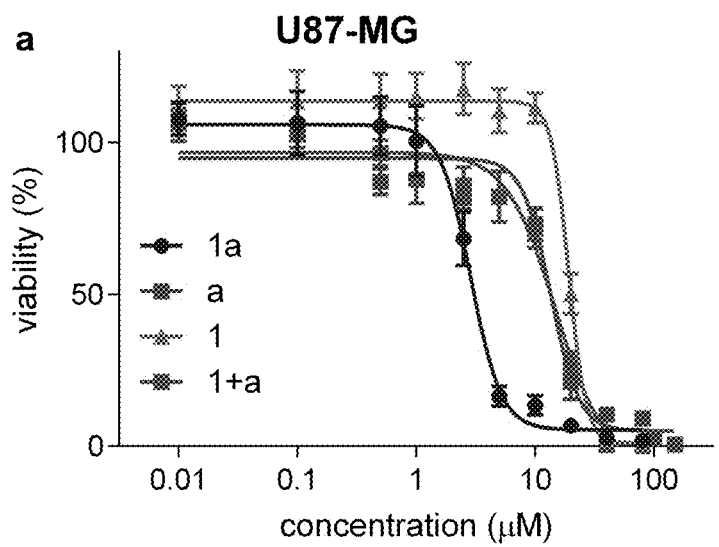
Figure 30A

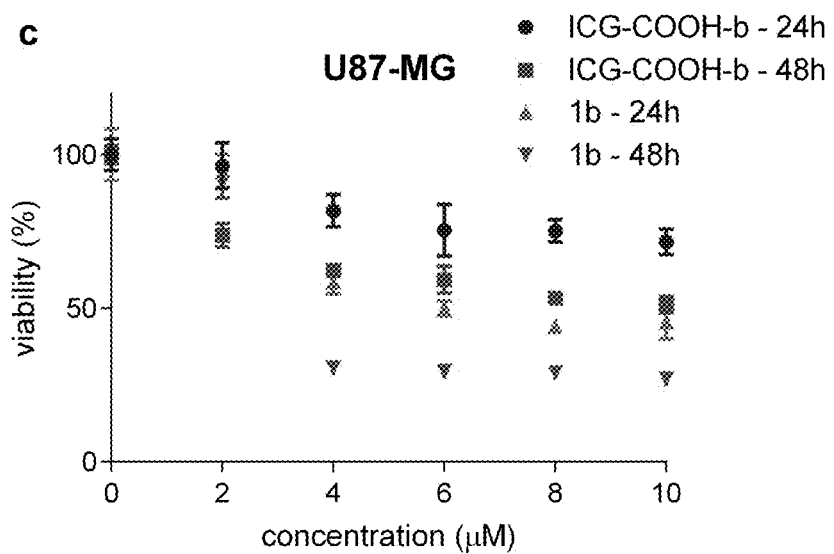
Figure 31C
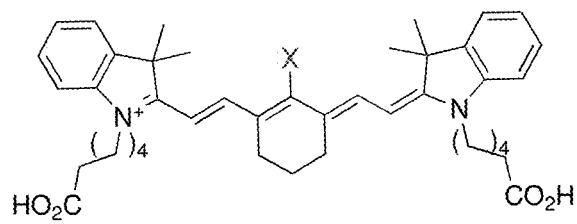
when X = Cl, 1; H, 4; Me, 5; Ph, 6
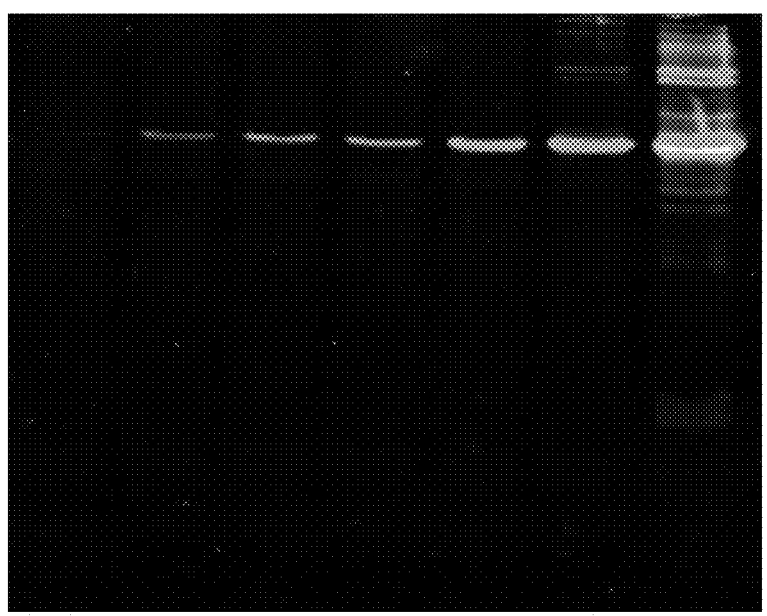
Figure 32 when X = Cl, 1-Cl; H, 1-H; Me, 1-Me; Ph, 1-Ph

CONJUGATES OF KINASE INHIBITORS AND CYANINE DYES

CROSS REFERENCE TO RELATED APPLICATIONS

This application claims the benefit of priority under 35 U.S.C. § 119(e) to U.S. Provisional Application No. 62/669,792, filed May 10, 2018; and U.S. Provisional Application No. 62/721,451, filed Aug. 22, 2018, which applications are incorporated herein by reference.

STATEMENT OF RIGHTS TO INVENTIONS MADE UNDER FEDERALLY SPONSORED RESEARCH

This invention was made with government support under grant number BC 141561 awarded by the Department of Defense. The government has certain rights in the invention.

BACKGROUND OF THE INVENTION

Cyanine dyes have been used for cancer therapy and imaging.[1-5] Many kinase inhibitors are FDA approved for clinical use in humans, but still their clinical applications tend to be limited.[6-8] A general problem with the first generation of kinase inhibitors is that tumor tend to develop "immunity". Immunity arises for several reasons, including: (i) kinase mutations in cancer cells, and (ii) upregulated efflux mechanisms that remove inhibitors from cells. In response, second generation kinase inhibitors that covalently bind to nucleophilic residues in the kinase active site have been developed. These tend to be more potent, but can have undesirable side-effects due to off-target binding. As such, there remains a need for new therapeutic compounds and methods for the treatment of cancer.

SUMMARY OF THE INVENTION

In one aspect, provided herein is a conjugate of Formula (I):

Cy-L-K    (I)

or a pharmaceutically acceptable salt thereof, wherein:
  Cy is a cyanine dye;
  L is a linker selected from optionally substituted aliphatic, optionally substituted heteroaliphatic, optionally substituted aryl, optionally substituted heteroaryl, or a combination thereof;
  K is moiety comprising a kinase inhibitor; and
  each — is a covalent bond.

In certain embodiments, Formula (I) is selected from:

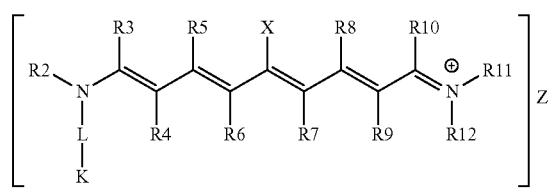

(Ia)

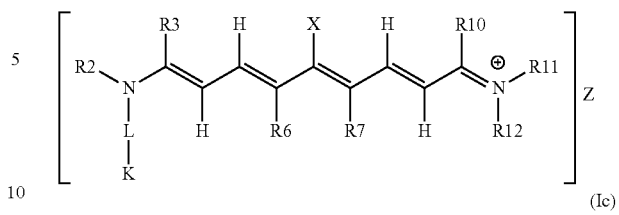

(Ib)

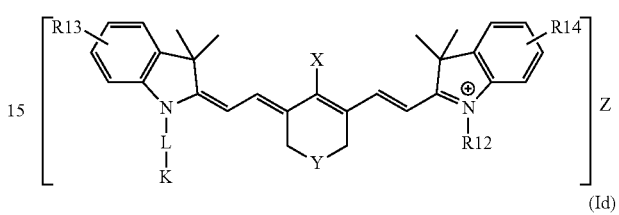

(Ic)

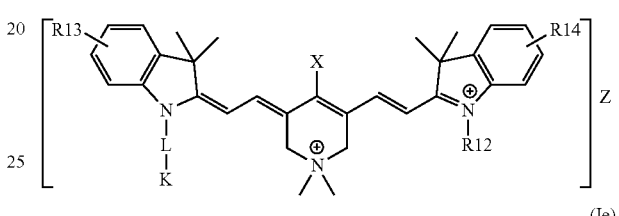

(Id)

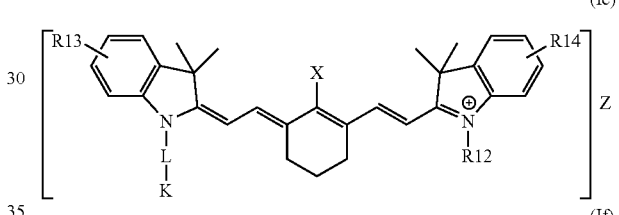

(Ie)

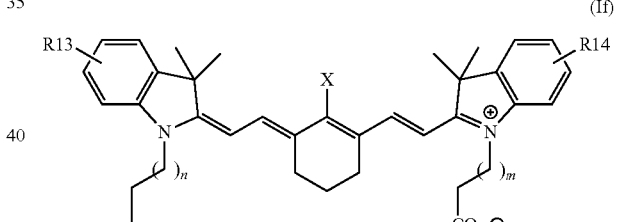

(If)

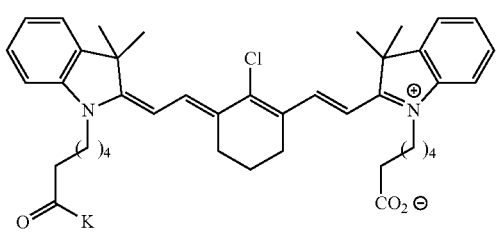

(Ig)

or a pharmaceutically acceptable salt thereof, wherein R2-R14, L, K, X and Z are as defined herein.

In another aspect, provided herein is a conjugate of Formula (II):

K-L-Cy-L-K    (II)

or a pharmaceutically acceptable salt thereof, wherein:
  Cy is a cyanine dye;
  each L independently is a linker selected from optionally substituted aliphatic, optionally substituted heteroaliphatic, optionally substituted aryl, optionally substituted heteroaryl, or a combination thereof;

each K independently is moiety comprising a kinase inhibitor; and each — is a covalent bond.

In certain embodiments, Formula (II) is selected from:

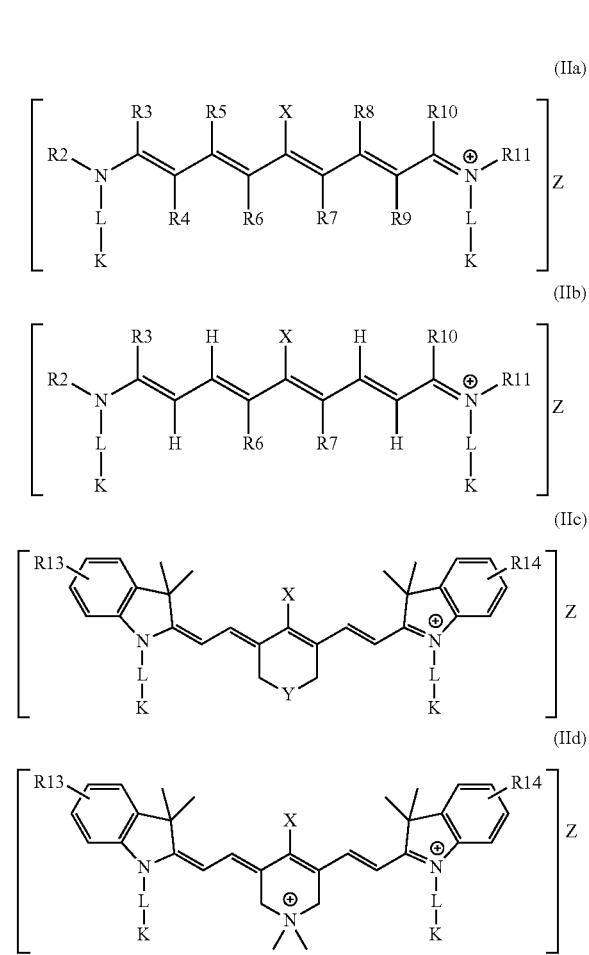

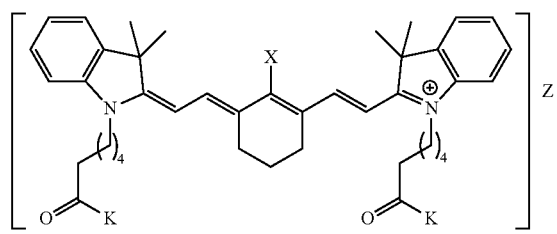

or a pharmaceutically acceptable salt thereof, wherein R2-R12, L, K, X and Z are as defined herein.

In another aspect, provided herein is a compound of Formula (III):

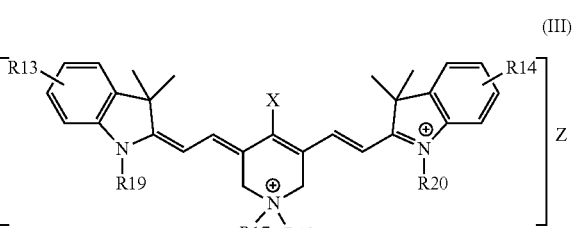

or a pharmaceutically acceptable salt thereof, wherein:

X is a leaving group;

Z is one or more anions to achieve electrical neutrality;

R13 and R14 independently are hydrogen or halogen;

R17 and R18 independently are alkyl, heteroalkyl, aryl or heteroaryl; and

R19 and R20 independently are hydrogen, optionally substituted aliphatic, optionally substituted heteroaliphatic, or a nitrogen protecting group.

In certain embodiments, the compound of Formula (III) is selected from:

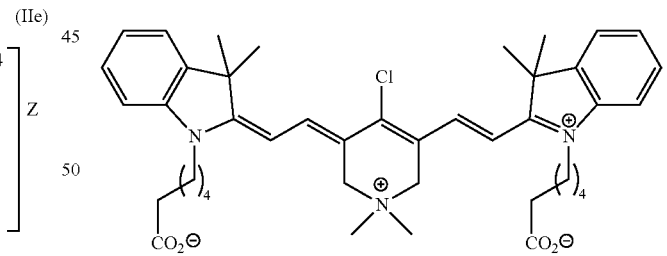

1-NMe₂

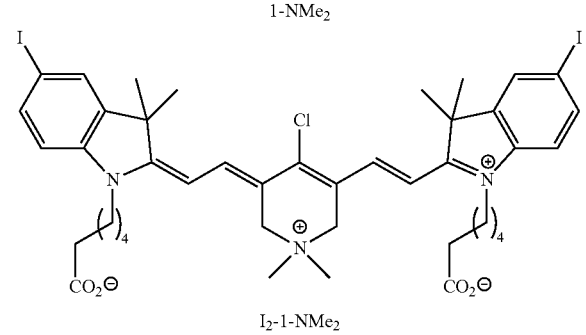

I₂-1-NMe₂

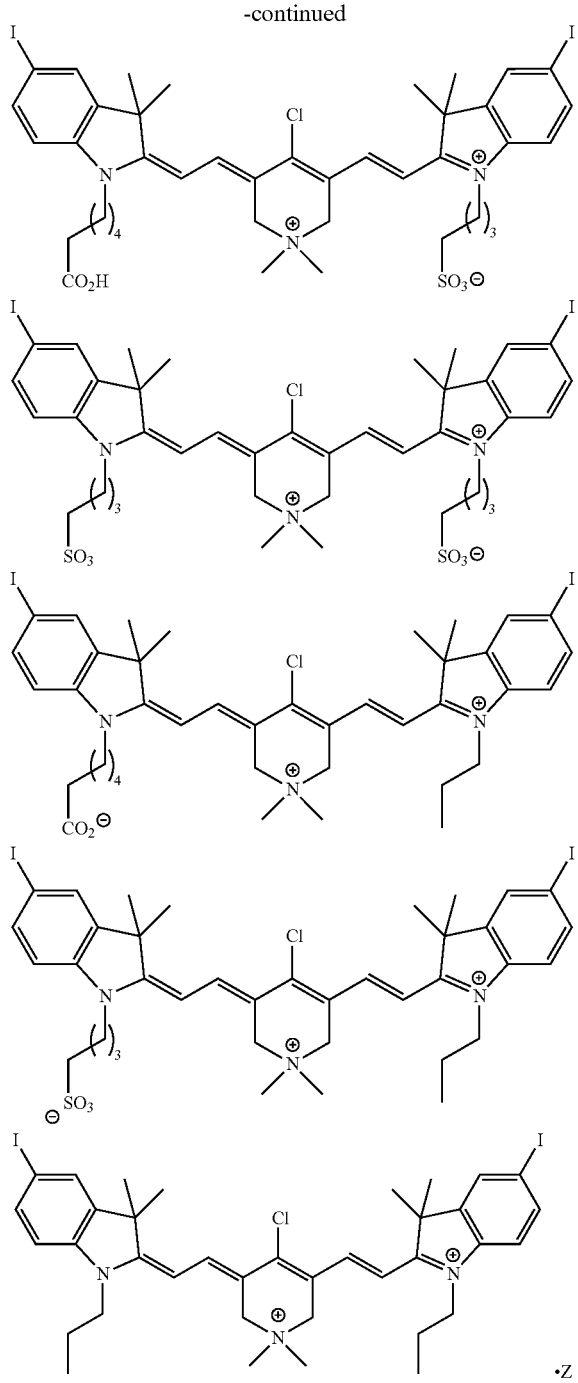

and pharmaceutically acceptable salts thereof.

In another aspect, provided herein is method of inhibiting the proliferation of a cancer cell, comprising contacting the cell with a conjugate as described herein.

In another aspect, provided herein is a method of treating cancer in a subject in need thereof, comprising administering to the subject a conjugate as described herein.

BRIEF DESCRIPTION OF THE DRAWINGS

FIG. 2 shows the synthesis scheme for 1a.

FIGS. 4A and 4B show cell viability assay of 1a on: a HEPG2 cells (liver cancer) (FIG. 4A); and U87-MG cells (glioblastoma) (FIG. 4B). 1a was more found to be toxic than individual 1, a or a combination of 1+a.

FIG. 5A shows morphology change;

FIG. 5B shows co-localization study in organelles, which showed it localizes more in mitochondria than lysosomes.

FIG. 24 shows 2aa uptake by U87-MG (GBM cells) cells as compared to HUVEC (normal cells). This shows the cancer cells uptake more of the compound than the "normal" HUVEC cells.

FIG. 25 shows light and dark toxicity of I2-1-NMe$_2$ on U87-MG (Glioblastoma) cells at different a, 6; b, 24 h at 10 mins irradiation. I2-1-NMe$_2$ showed was more toxic in light than in dark on U87-MG (Glioblastoma) cells.

FIGS. 30A to 30C show cytotoxicity of a, 1a; b, ICG-COOH-a; and c, comparison between 1a and ICG-COOH-a at 24 and 48 h on U87-MG (Glioblastoma). It was found that 1a was more toxic than ICG-COOH-a.

FIGS. 31A to 31C show cytotoxicity of a, 1b; b, ICG-COOH-b; and c, comparison between 1b and ICG-COOH-b at 24 and 48 h on U87-MG. It was found that 1b was more toxic than ICG-COOH-b.

FIG. 32 shows NIR-fluorescent gel image (>800 nm) of K562 cell lysate prior treated with different concentrations of 1-Cl for 20 h (30 μg of lysate protein was loaded in each well) in RPMI-1640 media containing 10% FBS.

FIG. 40C shows electrospray mass (ESI) spectra of: FIG. 40C, free HSA.

FIG. 41B shows analytical HPLC analyses for reactions of 0.5 mM HSA with 0.2 mM 1-Cl (in 1 M HEPES buffer pH 7.4) at 37° C. NIR-fluorescent gel image (>800 nm) of.

FIG. 44A: Without any blocking agents or abnormal conditions; FIG. 44B: pre-treated with 250 μM BSP to block OATPs for 10 mins; FIG. 44C: after the cells were pretreated with 1 mM DMOG for 24 h to induce hypoxia; and, FIG. 44D: when the cells were maintained at 0° C. for 30 mins to retard active transport. All images were collected using a Zeiss confocal microscope at 20× magnification.

DEFINITIONS

Figure 1:
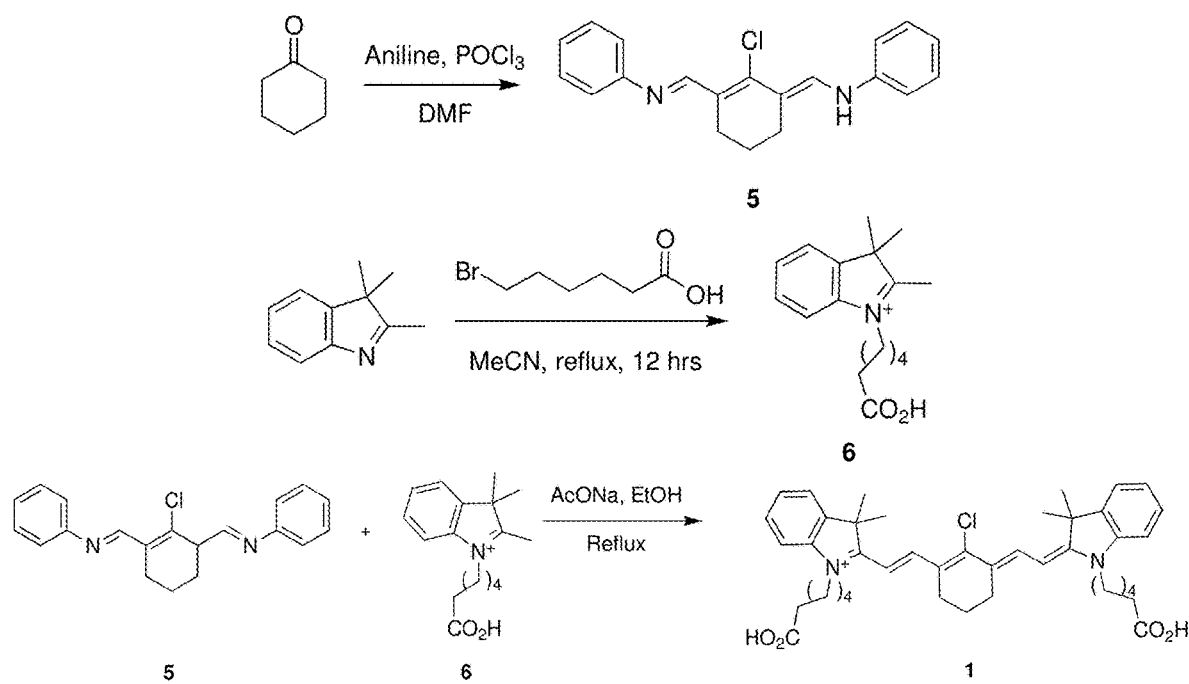
FIG. 1 shows the precursor for the synthesis of 1.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⌇ a single bond where the stereochemistry of the moieties immediately attached thereto is not specified, - - - is absent or a single bond, and ═══ or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., 2-methylpentyl, 3-methylpentyl, 2,2-dimethylbutyl, 2,3-dimethylbutyl, and n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("C-4 haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "carboxyalkyl" refers to an alkyl ester of the formula —CO$_2$(alkyl), wherein the alkyl moiety is as defined above.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

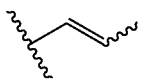

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

Groups recited herein in variable definitions are optionally substituted unless expressly provided otherwise. The term "optionally substituted" refers to being substituted or unsubstituted. In certain embodiments, aliphatic, alkyl, alkenyl, alkynyl, heteroaliphatic, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" heteroaliphatic, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{aa}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR, —OSO$_2$R, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^a$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$alkynyl, C$_{3-10}$ carbocyclyl, 3-14 membered heterocyclyl, C$_{6-4}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$ alkynyl, C$_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_1$-6alkyl, heteroC$_{2-6}$alkenyl, heteroC$_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$ (C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X is a counterion.

In certain embodiments, the carbon atom substituents are independently halogen, substituted or unsubstituted $C_{1-6}$ alkyl, —OR$^{aa}$, —SR$^{aa}$, —N(R$^{bb}$)$_2$, —CN, —SCN, —NO$_2$, —C(=O)R$^{aa}$, —CO$_2$R$^{aa}$, —C(=O)N(R$^{bb}$)$_2$, —OC(=O)R$^{aa}$, —OCO$_2$R$^{aa}$, —OC(=O)N(R$^{bb}$)$_2$, —NR$^{bb}$C(=O)R$^{aa}$, —NR$^{bb}$CO$_2$R, or —NR$^{bb}$C(=O)N(R$^{bb}$)$_2$. In certain embodiments, the carbon atom substituents are independently halogen, substituted or unsubstituted $C_{1-6}$ alkyl, —OR$^{aa}$, —SR$^{aa}$, —N(R$^{bb}$)$_2$, —CN, —SCN, or —NO$_2$.

The term "halo" or "halogen" refers to fluorine (fluoro, —F), chlorine (chloro, —Cl), bromine (bromo, —Br), or iodine (iodo, —I).

The term "-hydroxyl" or "—OH" refers to the group —OH. The term "substituted hydroxyl" or "substituted —OH," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{CC}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^a$, R$^{bb}$ and R$^{CC}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{CC}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X are as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R, —SO$_2$R$^{aa}$, —C(=NR$^{bb}$)R$^{aa}$, —C(=NR$^{cc}$)OR$^a$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amine protecting group" or an "amino protecting group"). The protecting group may be represented as "—PG". An amine group bearing a nitrogen protecting group, or two nitrogen protecting groups, may be referred to as a "protected amine." Nitrogen protecting groups include, but are not limited to, —OH, —OR, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^a$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-OHphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N—OHpiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)] methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(diOHboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-OHphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). The protecting group may be represented as "—PG". A hydroxyl group bearing an oxygen protecting group may be referred to as a "protected hydroxyl." Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$ and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, o-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "leaving group" is given its ordinary meaning in the art of synthetic organic chemistry and refers to an atom or a group capable of being displaced by a nucleophile.

Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, -OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, -OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. In certain embodiments, the leaving group is of the formula —SR$^{aa}$, —S(O)R$^{aa}$, —S(O)$_2$R$^{aa}$, —OC(O)R$^{aa}$, —OS(O)R$^{aa}$, —OS(O)$_2$R$^{aa}$, —OP(O)(R$^{aa}$)$_2$, —OP(O)(OR$^{aa}$)$_2$, —OP(=O)$_2$N(R$^{aa}$)$_2$, or —OP(=O)(NR$^{aa}$)$_2$, wherein R$^{aa}$ is as defined herein. Other non-limiting examples of leaving groups are water, ammonia, alcohols, ether moieties, thioether moieties, zinc halides, magnesium moieties, diazonium salts, and copper moieties.

The following definitions are more general terms used throughout the present application.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-OH-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, cows, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant produces fruit. In some embodiments, the plant is a tree or shrub.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease (e.g., a bacterial infection) described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease (e.g., a bacterial infection) but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The term "inhibition", "inhibiting", "inhibit," or "inhibitor" refer to the ability of a compound to reduce, slow, halt, and/or prevent activity of a particular biological process in a cell relative to vehicle.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, hematological malignancies. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenstrim's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM). Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma; sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

DETAILED DESCRIPTION

In one aspect, provided herein is a conjugate of Formula (I):

Cy-L-K (I)

or a pharmaceutically acceptable salt thereof, wherein:
Cy is a cyanine dye;
L is a linker selected from optionally substituted aliphatic, optionally substituted heteroaliphatic, optionally substituted aryl, optionally substituted heteroaryl, or a combination thereof;
K is moiety comprising a kinase inhibitor; and
each — is a covalent bond.

In another aspect, provided herein is a conjugate of Formula (II):

K-L-Cy-L-K (II)

or a pharmaceutically acceptable salt thereof, wherein:
Cy is a cyanine dye;
each L independently is a linker selected from optionally substituted aliphatic, optionally substituted heteroaliphatic, optionally substituted aryl, optionally substituted heteroaryl, or a combination thereof;
each K independently is moiety comprising a kinase inhibitor; and
each — is a covalent bond.

Variable Cy

Variable Cy is a cyanine dye radical or diradical. A cyanine dye is a molecule characterized by a polymethine bridge (i.e., a conjugated polyene diradical) between two nitrogen atoms, having a delocalized charge. In certain embodiments, the polymethine bridge comprises a substituent X, wherein X is a leaving group.

In certain embodiments, Cy comprises a meso-X. In certain embodiments, Cy does not contain a meso-aryl substituent. In certain embodiments, C comprises the following fragment:

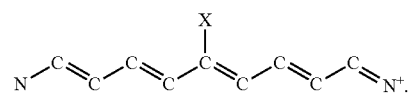

Cyanine dyes have high extinction coefficients (e.g., can be 100,000 Lmol$^{-1}$ cm$^{-1}$ or more). Properties of the chromophore, such as absorbance wavelength, photostability, and fluorescence, may be modulated by varying the substituents. For example, absorbance and fluorescence wavelength can be controlled by a choice of polymethine bridge length: longer cyanine dyes possess higher absorbance and emission wavelengths up to near infrared region.

Cyanine dyes penetrate, and are retained by cells (e.g., cancer cells).

In certain embodiments, Cy comprises a radical:

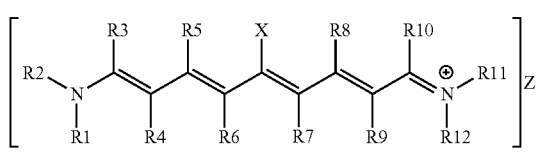

(Cy1)

or a pharmaceutically acceptable salt thereof, wherein:
X is a leaving group;
Z is one or more anions to achieve electrical neutrality;
R1 and R12 independently are optionally substituted aliphatic, optionally substituted heteroaliphatic, optionally substituted aryl, optionally substituted heteroaryl, or a bond to L;
R2 and R11 independently are optionally substituted aliphatic, optionally substituted heteroaliphatic, optionally substituted aryl, or optionally substituted heteroaryl; and
R3, R4, R5, R6, R7, R8, R9, and R10 independently are hydrogen, optionally substituted aliphatic, optionally substituted heteroaliphatic, optionally substituted aryl, or optionally substituted heteroaryl;
wherein any one of R1, R2, R3, R4, R5, R6, R7, R8, R9, R10, R11 and R12 may combine with another of R1, R2, R3, R4, R5, R6, R7, R8, R9, R10, R11 and R12 to form a five- or six-membered ring.

In certain embodiments, Cy comprises a radical:

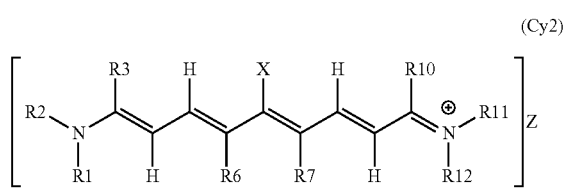

(Cy2)

or a pharmaceutically acceptable salt thereof, wherein:
R2 and R3 may combine to form a five- or six-membered ring;
R10 and R11 may combine to form a five- or six-membered ring; and
R6 and R7 may combine to form a five- or six-membered carbocyclic or heterocyclic ring; wherein said five- or six-membered rings are independently optionally substituted and independently optionally fused to one or more aryl or heteroaryl rings.

In certain embodiments, Cy moieties have improved water-solubility, bioavailability, and/or optical properties as compared to known cyanine dyes.

In certain embodiments Cy is (Cy3):

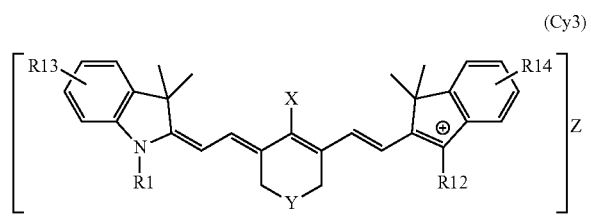

(Cy3)

or a pharmaceutically acceptable salt thereof, wherein:
Y is C(R15)(R16) or N(R17)(R18);
R13 and R14 independently are hydrogen, halogen, cyano, nitro, optionally substituted amino, optionally substituted alkyl, or optionally substituted heteroalkyl;
R15 and R16 independently are hydrogen, alkyl, heteroalkyl, aryl or heteroaryl; and
R17 and R18 independently are alkyl, heteroalkyl, aryl or heteroaryl.

In certain embodiments, X is halogen. In a particular embodiment, X is chlorine.

In certain embodiments, R13 and R14 are hydrogen. In certain embodiments, R13 and R14 are halogen. In particular embodiments wherein R13 and R14 are iodine, such moieties are useful in photodynamic therapy (PDT).

In certain embodiments, Y is C(R15)(R16). In certain embodiments, Y is $CH_2$. In certain embodiments, Y is N(R17)(R18). In certain embodiments, Y is $N(CH_3)_2$.

In certain embodiments, R1 is a bond to L. In certain embodiments, R12 is a bond to L.

In certain embodiments (Cy3) is selected from:

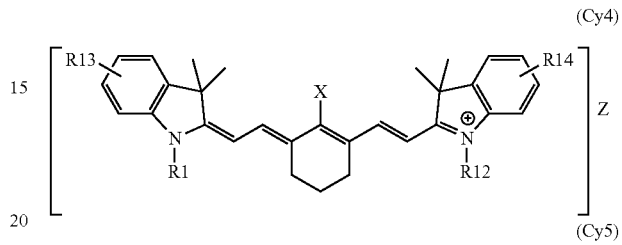

(Cy4)

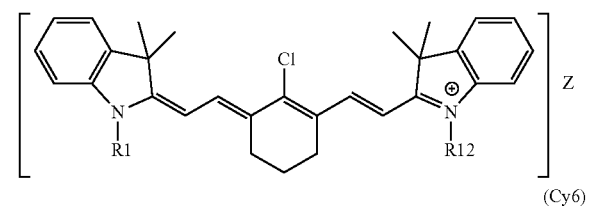

(Cy5)

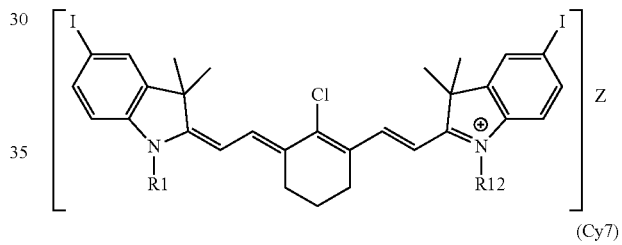

(Cy6)

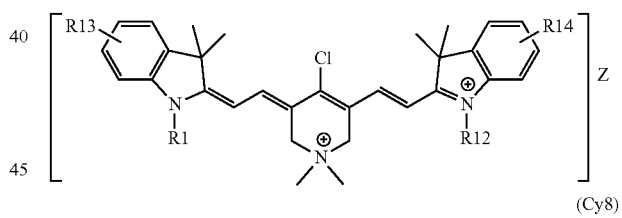

(Cy7)

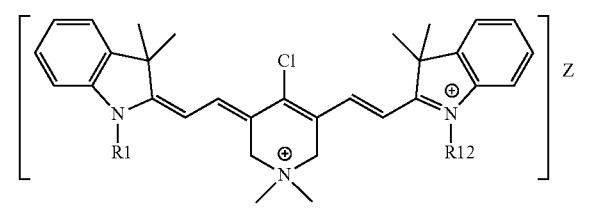

(Cy8)

(Cy9)

or a pharmaceutically acceptable salt thereof.

In certain embodiments, Formula (I) is:

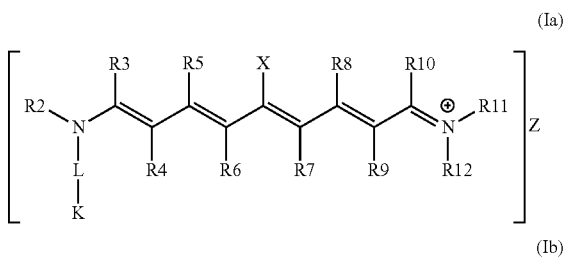
(Ia)

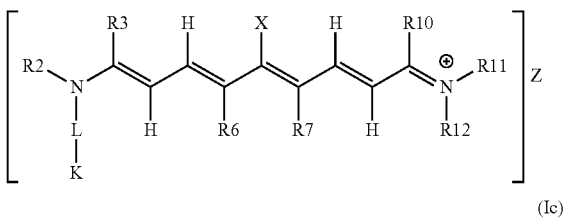
(Ib)

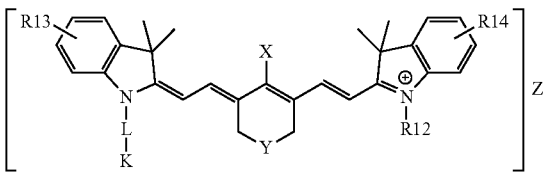
(Ic)

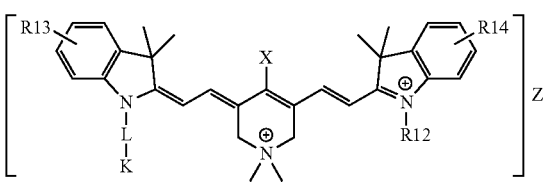
(Id)

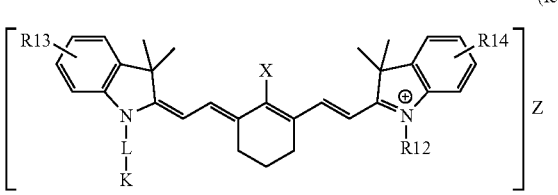
(Ie)

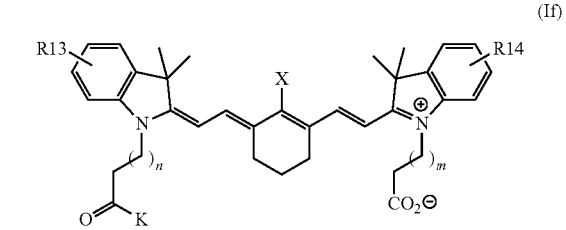
(If)

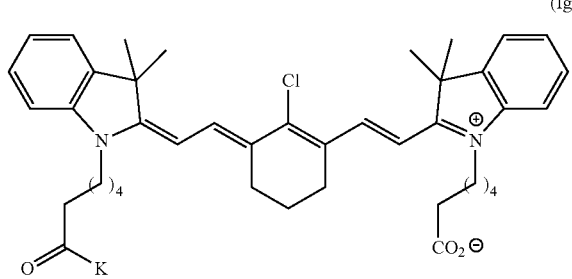
(Ig)

or a pharmaceutically acceptable salt thereof, wherein m and n independently are 2-20.

In certain particular embodiments, m and n independently are 4-6.

In certain embodiments, X is halogen. In a particular embodiment, X is chlorine.

In certain embodiments, R13 and R14 are hydrogen. In certain embodiments, R13 and R14 are halogen.

In certain embodiments, Y is C(R15)(R16). In certain embodiments, Y is $CH_2$. In certain embodiments, Y is N(R17)(R18). In certain embodiments, Y is $N(CH_3)_2$.

In certain embodiments, Formula (II) is:

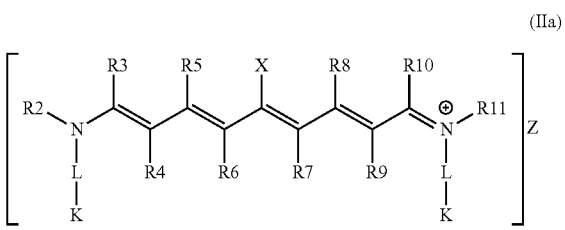
(IIa)

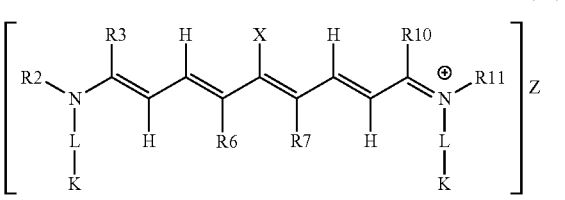
(IIb)

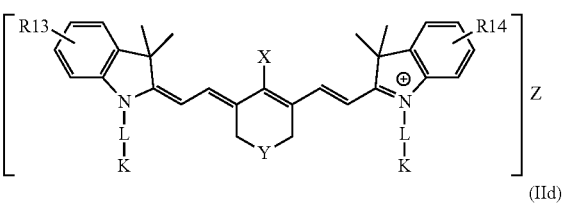
(IIc)

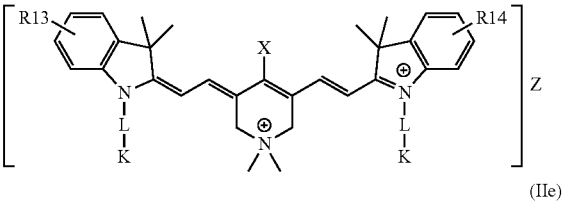
(IId)

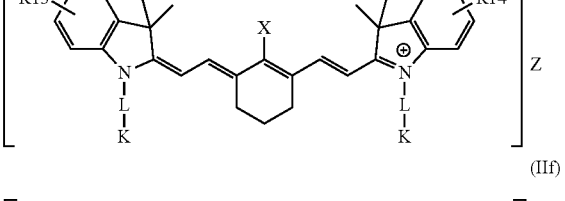
(IIe)

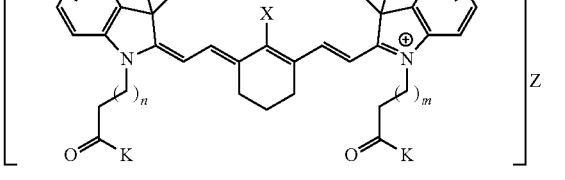
(IIf)

-continued

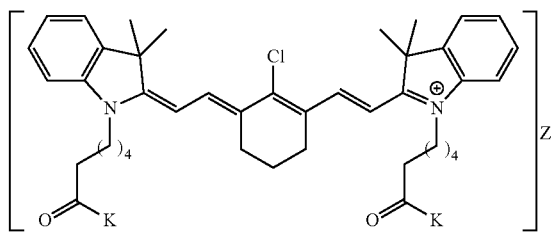

(IIg)

or a pharmaceutically acceptable salt thereof, wherein m and n independently are 2-20.

In certain particular embodiments, m and n independently are 4-6.

In certain embodiments, X is halogen. In a particular embodiment, X is chlorine.

In certain embodiments, R13 and R14 are hydrogen. In certain embodiments, R13 and R14 are halogen. In particular embodiments wherein R13 and R14 are iodine, such conjugates are useful in photodynamic therapy (PDT).

In certain embodiments, Y is C(R15)(R16). In certain embodiments, Y is $CH_2$. In certain embodiments, Y is N(R17)(R18). In certain embodiments, Y is $N(CH_3)_2$.

In certain embodiments of conjugates of Formulae (I) and (II), variable substituents L, K, R1-R18, X, and Z are defined as follows.

Variable X

In certain embodiments, X is a halogen. In certain particular embodiments, X is chlorine, bromine, or iodine. In a particular embodiment, X is chlorine.

In certain embodiments, X is a sulfonate. In certain particular embodiments, X is an alkylsulfonate (e.g., methylsulfonate), haloalkylsulfonate (e.g., trifluoromethylsulfonate), or arylsulfonate (e.g., p-toluenesulfonate or nitrophenylsulfonate).

In certain embodiments, X is a carboxylate. In certain particular embodiments, X is an alkyl carboxylate (e.g., acetate), haloalkylcarboxylate (e.g., trifluoroacetate), or an aryl carboxylate (e.g., benzoate or nitrobenzoate).

Variable Z

Z is one or more anions, which in combination with a specified chemical moiety, results in electrical neutrality. In certain embodiments, Z is not covalently attached to the specified chemical moiety. In certain particular embodiments, Z is a halide (e.g., chlorine, bromine or iodine). In certain particular embodiments, Z is a carboxylate (e.g., acetate or trifluoroacetate)

In other embodiments, Z is covalently attached to the specified chemical moiety. For example, Z may be a carboxylate anion that is comprised by a substituent of the specified chemical moiety (e.g., R12).

Variable R1

R1 is optionally substituted aliphatic, optionally substituted heteroaliphatic, optionally substituted aryl, optionally substituted heteroaryl, or a bond to L. In certain embodiments, R1 is unsubstituted aliphatic (e.g., unsubstituted $C_{1-6}$ akyl). In certain embodiments, R1 is substituted aliphatic (e.g., substituted $C_{1-6}$ akyl). In certain embodiments, R1 is unsubstituted heteroaliphatic (e.g., unsubstituted $C_{1-6}$ heteroakyl). In certain embodiments, R1 is substituted heteroaliphatic (e.g., substituted $C_{1-6}$ heteroakyl). In certain embodiments, R1 is unsubstituted aryl (e.g., $C_{6-10}$ aryl). In certain embodiments, R1 is substituted aryl (e.g., $C_{6-10}$ aryl). In certain embodiments, R1 is unsubstituted heteroaryl (e.g., $C_{3-10}$ heteroaryl). In certain embodiments, R1 is substituted heteroaryl (e.g., $C_{3-10}$ heteroaryl). In certain embodiments, R1 is a bond to L.

Variable R2

R2 is optionally substituted aliphatic, optionally substituted heteroaliphatic, optionally substituted aryl, or optionally substituted heteroaryl. In certain embodiments, R2 is unsubstituted aliphatic (e.g., unsubstituted $C_{1-6}$ akyl). In certain embodiments, R2 is substituted aliphatic (e.g., substituted $C_{1-6}$ akyl). In certain embodiments, R2 is unsubstituted heteroaliphatic (e.g., unsubstituted $C_{1-6}$ heteroakyl). In certain embodiments, R2 is substituted heteroaliphatic (e.g., substituted $C_{1-6}$ heteroakyl). In certain embodiments, R2 is unsubstituted aryl (e.g., $C_{6-10}$ aryl). In certain embodiments, R2 is substituted aryl (e.g., $C_{6-10}$ aryl). In certain embodiments, R2 is unsubstituted heteroaryl (e.g., $C_{3-10}$ heteroaryl). In certain embodiments, R2 is substituted heteroaryl (e.g., $C_{3-10}$ heteroaryl).

Variable R3

R3 is hydrogen, optionally substituted aliphatic, optionally substituted heteroaliphatic, optionally substituted aryl, or optionally substituted heteroaryl. In certain embodiments, R3 is hydrogen. In certain embodiments, R3 is unsubstituted aliphatic (e.g., unsubstituted $C_{1-6}$ akyl). In certain embodiments, R3 is substituted aliphatic (e.g., substituted $C_{1-6}$ akyl). In certain embodiments, R3 is unsubstituted heteroaliphatic (e.g., unsubstituted $C_{1-6}$ heteroakyl). In certain embodiments, R3 is substituted heteroaliphatic (e.g., substituted $C_{1-6}$ heteroakyl). In certain embodiments, R3 is unsubstituted aryl (e.g., $C_{6-10}$ aryl). In certain embodiments, R3 is substituted aryl (e.g., $C_{6-10}$ aryl). In certain embodiments, R3 is unsubstituted heteroaryl (e.g., $C_{3-10}$ heteroaryl). In certain embodiments, R3 is substituted heteroaryl (e.g., $C_{3-10}$ heteroaryl).

Variable R4

R4 is hydrogen, optionally substituted aliphatic, optionally substituted heteroaliphatic, optionally substituted aryl, or optionally substituted heteroaryl. In certain embodiments, R4 is hydrogen. In certain embodiments, R4 is unsubstituted aliphatic (e.g., unsubstituted $C_{1-6}$ akyl). In certain embodiments, R4 is substituted aliphatic (e.g., substituted $C_{1-6}$ akyl). In certain embodiments, R4 is unsubstituted heteroaliphatic (e.g., unsubstituted $C_{1-6}$ heteroakyl). In certain embodiments, R4 is substituted heteroaliphatic (e.g., substituted $C_{1-6}$ heteroakyl). In certain embodiments, R4 is unsubstituted aryl (e.g., $C_{6-10}$ aryl). In certain embodiments, R4 is substituted aryl (e.g., $C_{6-10}$ aryl). In certain embodiments, R4 is unsubstituted heteroaryl (e.g., $C_{3-10}$ heteroaryl). In certain embodiments, R4 is substituted heteroaryl (e.g., $C_{3-10}$ heteroaryl).

Variable R5

R5 is hydrogen, optionally substituted aliphatic, optionally substituted heteroaliphatic, optionally substituted aryl, or optionally substituted heteroaryl. In certain embodiments, R5 is hydrogen. In certain embodiments, R5 is unsubstituted aliphatic (e.g., unsubstituted $C_{1-6}$ akyl). In certain embodiments, R5 is substituted aliphatic (e.g., substituted $C_{1-6}$ akyl). In certain embodiments, R5 is unsubstituted heteroaliphatic (e.g., unsubstituted $C_{1-6}$ heteroakyl). In certain embodiments, R5 is substituted heteroaliphatic (e.g., substituted $C_{1-6}$ heteroakyl). In certain embodiments, R5 is unsubstituted aryl (e.g., $C_{6-10}$ aryl). In certain embodiments, R5 is substituted aryl (e.g., $C_{6-10}$ aryl). In certain embodiments, R5 is unsubstituted heteroaryl (e.g., $C_{3-10}$ heteroaryl). In certain embodiments, R5 is substituted heteroaryl (e.g., $C_{3-10}$ heteroaryl).

Variable R6

R6 is hydrogen, optionally substituted aliphatic, optionally substituted heteroaliphatic, optionally substituted aryl, or optionally substituted heteroaryl. In certain embodiments, R6 is hydrogen. In certain embodiments, R6 is unsubstituted aliphatic (e.g., unsubstituted $C_{1-6}$ akyl). In certain embodiments, R6 is substituted aliphatic (e.g., substituted $C_{1-6}$ akyl). In certain embodiments, R6 is unsubstituted heteroaliphatic (e.g., unsubstituted $C_{1-6}$ heteroakyl). In certain embodiments, R6 is substituted heteroaliphatic (e.g., substituted $C_{1-6}$ heteroakyl). In certain embodiments, R6 is unsubstituted aryl (e.g., $C_{6-10}$ aryl). In certain embodiments, R6 is substituted aryl (e.g., $C_{6-10}$ aryl). In certain embodiments, R6 is unsubstituted heteroaryl (e.g., $C_{3-10}$ heteroaryl). In certain embodiments, R6 is substituted heteroaryl (e.g., $C_{3-10}$ heteroaryl).

Variable R7

R7 is hydrogen, optionally substituted aliphatic, optionally substituted heteroaliphatic, optionally substituted aryl, or optionally substituted heteroaryl. In certain embodiments, R7 is hydrogen. In certain embodiments, R7 is unsubstituted aliphatic (e.g., unsubstituted $C_{1-6}$ akyl). In certain embodiments, R7 is substituted aliphatic (e.g., substituted $C_{1-6}$ akyl). In certain embodiments, R7 is unsubstituted heteroaliphatic (e.g., unsubstituted $C_{1-6}$ heteroakyl). In certain embodiments, R7 is substituted heteroaliphatic (e.g., substituted $C_{1-6}$ heteroakyl). In certain embodiments, R7 is unsubstituted aryl (e.g., $C_{6-10}$ aryl). In certain embodiments, R7 is substituted aryl (e.g., $C_{6-10}$ aryl). In certain embodiments, R7 is unsubstituted heteroaryl (e.g., $C_{3-10}$ heteroaryl). In certain embodiments, R7 is substituted heteroaryl (e.g., $C_{3-10}$ heteroaryl).

Variable R8

R8 is hydrogen, optionally substituted aliphatic, optionally substituted heteroaliphatic, optionally substituted aryl, or optionally substituted heteroaryl. In certain embodiments, R8 is hydrogen. In certain embodiments, R8 is unsubstituted aliphatic (e.g., unsubstituted $C_{1-6}$ akyl). In certain embodiments, R8 is substituted aliphatic (e.g., substituted $C_{1-6}$ akyl). In certain embodiments, R8 is unsubstituted heteroaliphatic (e.g., unsubstituted $C_{1-6}$ heteroakyl). In certain embodiments, R8 is substituted heteroaliphatic (e.g., substituted $C_{1-6}$ heteroakyl). In certain embodiments, R8 is unsubstituted aryl (e.g., $C_{6-10}$ aryl). In certain embodiments, R8 is substituted aryl (e.g., $C_{6-10}$ aryl). In certain embodiments, R8 is unsubstituted heteroaryl (e.g., $C_{3-10}$ heteroaryl). In certain embodiments, R8 is substituted heteroaryl (e.g., $C_{3-10}$ heteroaryl).

Variable R9

R9 is hydrogen, optionally substituted aliphatic, optionally substituted heteroaliphatic, optionally substituted aryl, or optionally substituted heteroaryl. In certain embodiments, R9 is hydrogen. In certain embodiments, R9 is unsubstituted aliphatic (e.g., unsubstituted $C_{1-6}$ akyl). In certain embodiments, R9 is substituted aliphatic (e.g., substituted $C_{1-6}$ akyl). In certain embodiments, R9 is unsubstituted heteroaliphatic (e.g., unsubstituted $C_{1-6}$ heteroakyl). In certain embodiments, R9 is substituted heteroaliphatic (e.g., substituted $C_{1-6}$ heteroakyl). In certain embodiments, R9 is unsubstituted aryl (e.g., $C_{6-10}$ aryl). In certain embodiments, R9 is substituted aryl (e.g., $C_{6-10}$ aryl). In certain embodiments, R9 is unsubstituted heteroaryl (e.g., $C_{3-10}$ heteroaryl). In certain embodiments, R9 is substituted heteroaryl (e.g., $C_{3-10}$ heteroaryl).

Variable R10

R10 is hydrogen, optionally substituted aliphatic, optionally substituted heteroaliphatic, optionally substituted aryl, or optionally substituted heteroaryl. In certain embodiments, R10 is hydrogen. In certain embodiments, R10 is unsubstituted aliphatic (e.g., unsubstituted $C_{1-6}$ akyl). In certain embodiments, R10 is substituted aliphatic (e.g., substituted $C_{1-6}$ akyl). In certain embodiments, R10 is unsubstituted heteroaliphatic (e.g., unsubstituted $C_{1-6}$ heteroakyl). In certain embodiments, R10 is substituted heteroaliphatic (e.g., substituted $C_{1-6}$ heteroakyl). In certain embodiments, R10 is unsubstituted aryl (e.g., $C_{6-10}$ aryl). In certain embodiments, R10 is substituted aryl (e.g., $C_{6-10}$ aryl). In certain embodiments, R10 is unsubstituted heteroaryl (e.g., $C_{3-10}$ heteroaryl). In certain embodiments, R10 is substituted heteroaryl (e.g., $C_{3-10}$ heteroaryl).

Variable R11

R11 is optionally substituted aliphatic, optionally substituted heteroaliphatic, optionally substituted aryl, or optionally substituted heteroaryl. In certain embodiments, R11 is unsubstituted aliphatic (e.g., unsubstituted $C_{1-6}$ akyl). In certain embodiments, R11 is substituted aliphatic (e.g., substituted $C_{1-6}$ akyl). In certain embodiments, R11 is unsubstituted heteroaliphatic (e.g., unsubstituted $C_{1-6}$ heteroakyl). In certain embodiments, R11 is substituted heteroaliphatic (e.g., substituted $C_{1-6}$ heteroakyl). In certain embodiments, R11 is unsubstituted aryl (e.g., $C_{6-10}$ aryl). In certain embodiments, R11 is substituted aryl (e.g., $C_{6-10}$ aryl). In certain embodiments, R11 is unsubstituted heteroaryl (e.g., $C_{3-10}$ heteroaryl). In certain embodiments, R11 is substituted heteroaryl (e.g., $C_{3-10}$ heteroaryl).

Variable R12

R12 is optionally substituted aliphatic, optionally substituted heteroaliphatic, optionally substituted aryl, optionally substituted heteroaryl, or a bond to L. In certain embodiments, R12 is unsubstituted aliphatic (e.g., unsubstituted $C_{1-6}$ akyl). In certain embodiments, R12 is substituted aliphatic (e.g., substituted $C_{1-6}$ akyl). In certain embodiments, R12 is unsubstituted heteroaliphatic (e.g., unsubstituted $C_{1-6}$ heteroakyl). In certain embodiments, R12 is substituted heteroaliphatic (e.g., substituted $C_{1-6}$ heteroakyl). In certain embodiments, R12 is unsubstituted aryl (e.g., $C_{6-10}$ aryl). In certain embodiments, R12 is substituted aryl (e.g., $C_{6-10}$ aryl). In certain embodiments, R12 is unsubstituted heteroaryl (e.g., $C_{3-10}$ heteroaryl). In certain embodiments, R12 is substituted heteroaryl (e.g., $C_{3-10}$ heteroaryl). In certain embodiments, R12 is a bond to L.

Variable R13

R13 is hydrogen, halogen, cyano, nitro, optionally substituted amino, optionally substituted alkyl, or optionally substituted heteroalkyl. In certain embodiments, R13 is hydrogen. In certain embodiments, R13 is halogen (e.g., iodine). In certain embodiments, R13 is cyano. In certain embodiments, R13 is nitro. In certain embodiments, R13 is unsubstituted amino. In certain embodiments, R13 is substituted amino. In certain embodiments, R13 is unsubstituted alkyl. In certain embodiments, R13 is substituted alkyl. In certain embodiments, R13 is unsubstituted heteroalkyl. In certain embodiments, R13 is substituted heteroalkyl.

Variable R14

R14 is hydrogen, halogen, cyano, nitro, optionally substituted amino, optionally substituted alkyl, or optionally substituted heteroalkyl. In certain embodiments, R14 is hydrogen. In certain embodiments, R14 is halogen (e.g., iodine). In certain embodiments, R14 is cyano. In certain embodiments, R14 is nitro. In certain embodiments, R14 is unsubstituted amino. In certain embodiments, R14 is substituted amino. In certain embodiments, R14 is unsubstituted alkyl. In certain embodiments, R13 is substituted alkyl. In certain embodiments, R14 is unsubstituted heteroalkyl. In certain embodiments, R14 is substituted heteroalkyl.

Variable R15

R15 is hydrogen, alkyl, heteroalkyl, aryl or heteroaryl. In certain embodiments, R15 is hydrogen. In certain embodiments, R15 is unsubstituted alkyl. In certain embodiments, R15 is substituted alkyl. In certain embodiments, R15 is unsubstituted heteroalkyl. In certain embodiments, R15 is substituted heteroalkyl. In certain embodiments, R15 is unsubstituted aryl (e.g., $C_{6-10}$ aryl). In certain embodiments, R15 is substituted aryl (e.g., $C_{6-10}$ aryl). In certain embodiments, R15 is unsubstituted heteroaryl (e.g., $C_{3-10}$ heteroaryl). In certain embodiments, R15 is substituted heteroaryl (e.g., $C_{3-10}$ heteroaryl).

Variable R16

R16 is hydrogen, alkyl, heteroalkyl, aryl or heteroaryl. In certain embodiments, R16 is hydrogen. In certain embodiments, R16 is unsubstituted alkyl. In certain embodiments, R16 is substituted alkyl. In certain embodiments, R16 is unsubstituted heteroalkyl. In certain embodiments, R16 is substituted heteroalkyl. In certain embodiments, R16 is unsubstituted aryl (e.g., $C_{6-10}$ aryl). In certain embodiments, R16 is substituted aryl (e.g., $C_{6-10}$ aryl). In certain embodiments, R16 is unsubstituted heteroaryl (e.g., $C_{3-10}$ heteroaryl). In certain embodiments, R16 is substituted heteroaryl (e.g., $C_{3-10}$ heteroaryl).

Variable R17

R17 is alkyl, heteroalkyl, aryl or heteroaryl. In certain embodiments, R17 is unsubstituted alkyl. In certain embodiments, R17 is substituted alkyl. In certain embodiments, R17 is unsubstituted heteroalkyl. In certain embodiments, R17 is substituted heteroalkyl. In certain embodiments, R17 is unsubstituted aryl (e.g., $C_{6-10}$ aryl). In certain embodiments, R17 is substituted aryl (e.g., $C_{6-10}$ aryl). In certain embodiments, R17 is unsubstituted heteroaryl (e.g., $C_{3-10}$ heteroaryl). In certain embodiments, R17 is substituted heteroaryl (e.g., $C_{3-10}$ heteroaryl).

Variable R18

R18 is alkyl, heteroalkyl, aryl or heteroaryl. In certain embodiments, R18 is unsubstituted alkyl. In certain embodiments, R18 is substituted alkyl. In certain embodiments, R18 is unsubstituted heteroalkyl. In certain embodiments, R18 is substituted heteroalkyl. In certain embodiments, R18 is unsubstituted aryl (e.g., $C_{6-10}$ aryl). In certain embodiments, R18 is substituted aryl (e.g., $C_{6-10}$ aryl). In certain embodiments, R18 is unsubstituted heteroaryl (e.g., $C_{3-10}$ heteroaryl). In certain embodiments, R18 is substituted heteroaryl (e.g., $C_{3-10}$ heteroaryl).

Variable L

L is a divalent linker. In certain embodiments, L is selected from optionally substituted aliphatic, optionally substituted heteroaliphatic, optionally substituted aryl, optionally substituted heteroaryl, or a combination thereof. In certain embodiments, L is unsubstituted aliphatic (e.g., unsubstituted $C_{1-6}$ akyl). In certain embodiments, L is substituted aliphatic (e.g., substituted $C_{1-6}$ akyl). In certain embodiments, L is unsubstituted heteroaliphatic (e.g., unsubstituted $C_{1-6}$ heteroakyl). In certain embodiments, L is substituted heteroaliphatic (e.g., substituted $C_{1-6}$ heteroakyl). In certain embodiments, L is unsubstituted aryl (e.g., $C_{6-10}$ aryl). In certain embodiments, L is substituted aryl (e.g., $C_{6-10}$ aryl). In certain embodiments, L is unsubstituted heteroaryl (e.g., $C_{3-10}$ heteroaryl). In certain embodiments, L is substituted heteroaryl (e.g., $C_{3-10}$ heteroaryl). In certain embodiments, L is a combination of one or more of optionally substituted aliphatic, optionally substituted heteroaliphatic, optionally substituted aryl, and optionally substituted heteroaryl.

In certain particular embodiments, L is an alkyl or heteroalkyl chain further comprising a moiety selected from ester, amide, oxime, succinimide, and hydroxysuccinimide ester.

Variable K

K is a moiety comprising a kinase inhibitor. In certain embodiments, K is a kinase inhibitor. In certain embodiments, K further comprises a chemical functional group having the purpose of conjugating K to the linker (L).

Any kinase inhibitor known in the art or developed in the future may be used in conjugates according to the present disclosure. In certain embodiments, the kinase inhibitor is a receptor tyrosine kinase (RTK) inhibitor, fibroblast growth factor receptor (FGFR) inhibitor (e.g., BGJ398), epidermal growth factor receptor (EGFR) inhibitor (e.g., erlotinib (Tarceva), AZD8931, or WZ4002), mitogen-activated protein kinase (MEK) inhibitor (e.g., trametinib), phosphatidylinositol-4,5-bisphosphate 3-kinase (PI3K) inhibitor (e.g., BKM120 (buparlisib) or BEZ235 (dactolisib)), receptor tyrosine-protein kinase erbB-2 (HER-2) inhibitor (e.g., lapatinib), mammalian target of rapamycin (mTOR) inhibitor (e.g., Torin2), or anaplastic lymphoma kinase (ALK) inhibitor (e.g., crizotinib). In certain embodiments, the kinase inhibitor is a platelet-derived growth factor receptor (PDGFR) inhibitor (e.g., imatinib). In certain embodiments the kinase inhibitor is a or B-Raf enzyme inhibitor or MEK inhibitor (e.g., vemurafenib).

In certain embodiments, the kinase inhibitor is an inhibitor of AAK1, ABL, ACK, ACTR2, ACTR2B, AKT1, AKT2, AKT3, AMPKal, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLK1, CLIKIL, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRKIA, DYRKIB, DYRK2, DYRK3, DYRK4, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps, Erk3ps2, Erk3ps3, Erk3ps4, Erk4, Erk5, Erk7, FAK, FER, FERps, FES, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRaa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgKO50ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, ZC4/NRK, or a combination thereof.

In certain embodiments, the kinase inhibitor is selected from adavosertib, afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, su6656, vandetanib, and vemurafenib. In certain embodiments, K is a radical having a structure corresponding to a kinase inhibitor identified above.

In certain particular embodiments, K is selected from:

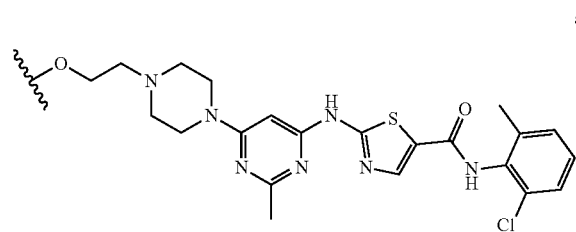

a

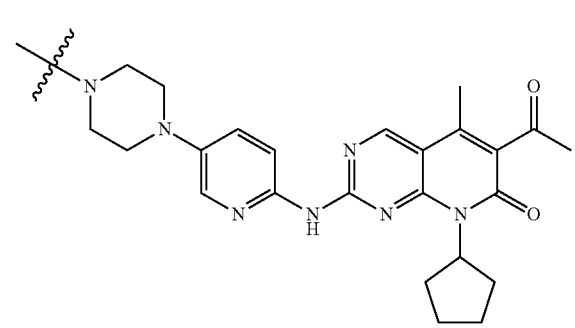

b

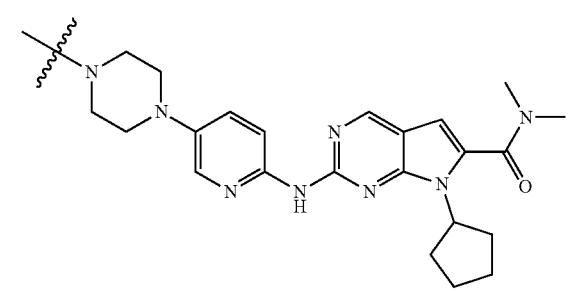

c

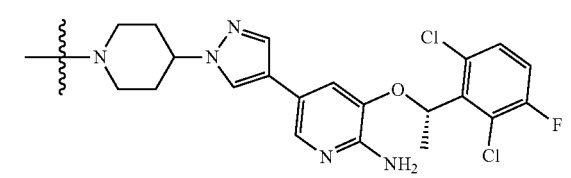

d

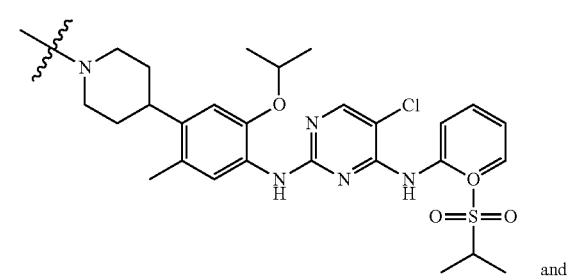

and e

-continued f

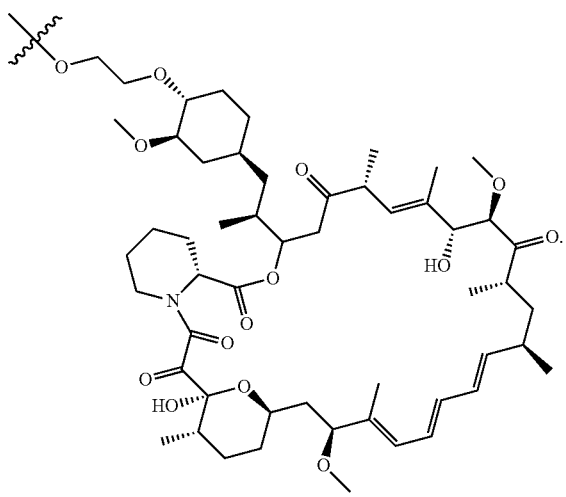

In another aspect, provided herein is method of inhibiting the proliferation of a cancer cell, comprising contacting the cell with a conjugate as described herein.

In another aspect, provided herein is a method of treating cancer in a subject in need thereof, comprising administering to the subject a conjugate as described herein.

In another aspect, provided herein is a compound of Formula (III):

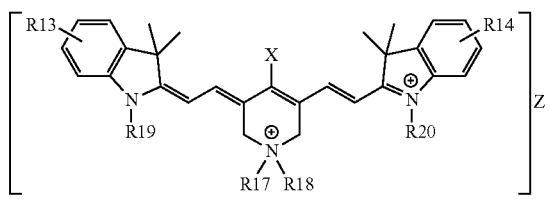

(III)

or a pharmaceutically acceptable salt thereof, wherein:

X is a leaving group;

Z is one or more anions to achieve electrical neutrality;

R13 and R14 independently are hydrogen, halogen, cyano, nitro, optionally substituted amino, optionally substituted alkyl, or optionally substituted heteroalkyl;

R17 and R18 independently are alkyl, heteroalkyl, aryl or heteroaryl; and

R19 and R20 independently are hydrogen, optionally substituted aliphatic, optionally substituted heteroaliphatic, or a nitrogen protecting group.

In certain embodiments, X is a halogen. In certain particular embodiments, X is chlorine, bromine, or iodine. In a particular embodiment, X is chlorine. In certain embodiments, X is a sulfonate. In certain particular embodiments, X is an alkylsulfonate (e.g., methylsulfonate), haloalkylsulfonate (e.g., trifluoromethylsulfonate), or arylsulfonate (e.g., p-toluenesulfonate or nitrophenylsulfonate). In certain embodiments, X is a carboxylate. In certain particular embodiments, X is an alkyl carboxylate (e.g., acetate), haloalkylcarboxylate (e.g., trifluoroacetate), or an aryl carboxylate (e.g., benzoate or nitrobenzoate).

In certain embodiments, Z is not covalently attached to the dye (e.g., is not comprised by R13, R14, R17, R18, R19 or R20). In certain embodiments, Z is covalently attached to the dye. In certain particular embodiments, Z is a halide (e.g., chlorine, bromine or iodine). In certain particular embodiments, Z is a carboxylate (e.g., acetate or trifluoroacetate).

In certain embodiments, R13 is hydrogen. In certain embodiments, R13 is halogen. In certain embodiments, R13 is cyano. In certain embodiments, R13 is nitro. In certain embodiments, R13 is unsubstituted amino. In certain embodiments, R13 is substituted amino. In certain embodiments, R13 is unsubstituted alkyl. In certain embodiments, R13 is substituted alkyl. In certain embodiments, R13 is unsubstituted heteroalkyl. In certain embodiments, R13 is substituted heteroalkyl.

In certain embodiments, R14 is hydrogen. In certain embodiments, R14 is halogen. In certain embodiments, R14 is cyano. In certain embodiments, R14 is nitro. In certain embodiments, R14 is unsubstituted amino. In certain embodiments, R14 is substituted amino. In certain embodiments, R14 is unsubstituted alkyl. In certain embodiments, R13 is substituted alkyl. In certain embodiments, R14 is unsubstituted heteroalkyl. In certain embodiments, R14 is substituted heteroalkyl.

In certain particular embodiments, R13 and R14 are hydrogen. In other embodiments, R13 and R14 are halogen (e.g., iodine).

In certain embodiments, R17 is substituted alkyl. In certain embodiments, R17 is unsubstituted heteroalkyl. In certain embodiments, R17 is substituted heteroalkyl. In certain embodiments, R17 is unsubstituted aryl (e.g., $C_{6-10}$ aryl). In certain embodiments, R17 is substituted aryl (e.g., $C_{6-10}$ aryl). In certain embodiments, R17 is unsubstituted heteroaryl (e.g., $C_{3-10}$ heteroaryl). In certain embodiments, R17 is substituted heteroaryl (e.g., $C_{3-10}$ heteroaryl).

In certain embodiments, R18 is substituted alkyl. In certain embodiments, R18 is unsubstituted heteroalkyl. In certain embodiments, R18 is substituted heteroalkyl. In certain embodiments, R18 is unsubstituted aryl (e.g., $C_{6-10}$ aryl). In certain embodiments, R18 is substituted aryl (e.g., $C_{6-10}$ aryl). In certain embodiments, R18 is unsubstituted heteroaryl (e.g., $C_{3-10}$ heteroaryl). In certain embodiments, R18 is substituted heteroaryl (e.g., $C_{3-10}$ heteroaryl).

In certain embodiments, R17 and R18 are alkyl. In certain particular embodiments, R17 and R18 are methyl.

In certain embodiments, R19 is hydrogen. In certain embodiments, R19 is unsubstituted aliphatic (e.g., unsubstituted $C_{1-6}$ akyl). In certain embodiments, R19 is substituted aliphatic (e.g., substituted $C_{1-6}$ akyl). In certain embodiments, R19 is unsubstituted heteroaliphatic (e.g., unsubstituted $C_{1-6}$ heteroakyl). In certain embodiments, R19 is substituted heteroaliphatic (e.g., substituted $C_{1-6}$ heteroakyl). In certain embodiments, R19 is a nitrogen protecting group.

In certain embodiments, R20 is hydrogen. In certain embodiments, R20 is unsubstituted aliphatic (e.g., unsubstituted $C_{1-6}$ akyl). In certain embodiments, R20 is substituted aliphatic (e.g., substituted $C_{1-6}$ akyl). In certain embodiments, R20 is unsubstituted heteroaliphatic (e.g., unsubstituted $C_{1-6}$ heteroakyl). In certain embodiments, R20 is substituted heteroaliphatic (e.g., substituted $C_{1-6}$ heteroakyl). In certain embodiments, R20 is a nitrogen protecting group.

In certain embodiments, R19 and R20 are are alkyl substituted with —$CO_2H$ or —$SO_3H$.

In certain embodiments, compounds of Formula (III) have improved water-solubility, bioavailability, and/or optical properties as compared to known cyanine dyes.

In certain embodiments, the compound of Formula (III) is selected from:

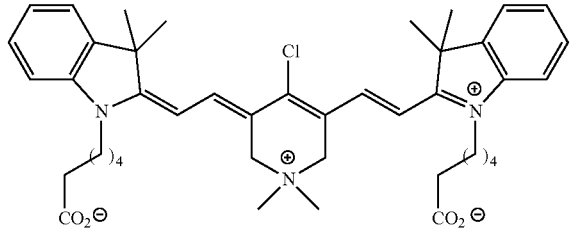

1-NMe₂

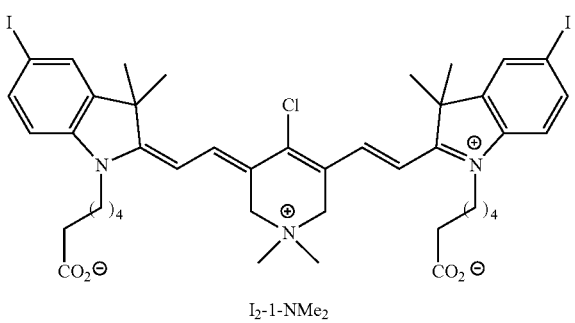

I₂-1-NMe₂

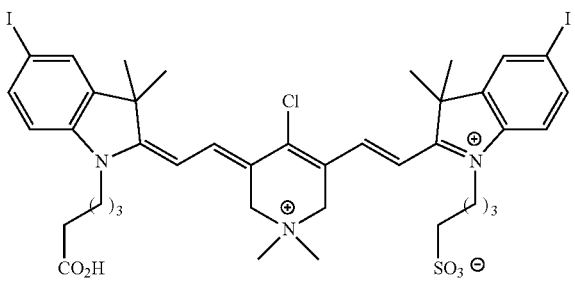

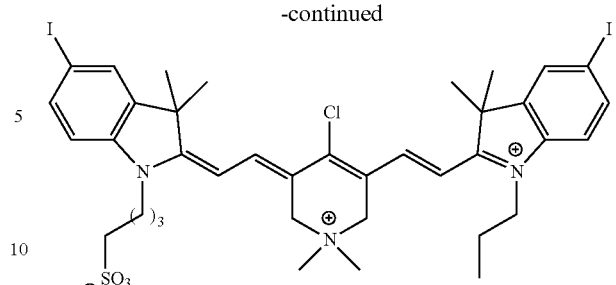

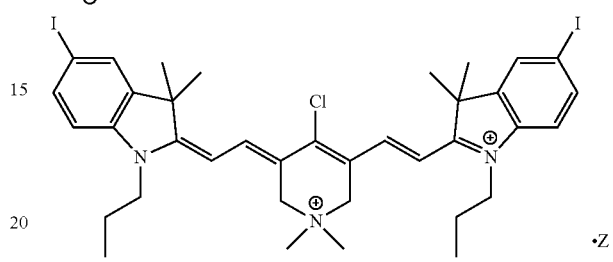

·Z and pharmaceutically acceptable salts thereof.

Methods and Uses

Cancer cells treated with dye compounds containing the moiety Cy are chemically changed insofar as biomolecules (e.g., proteins such as albumin) within the cells becomes covalently labeled with the dye (e.g., by displacing the leaving group X). The labeled biomolecules (e.g., proteins such as albumin) can be observed as distinct fluorescent bands when the cells are lysed and the lysate is separated by gel electrophoresis, and then visualized with near-IR fluorescence. Similar dyes, but which do not have the leaving group X, do not afford the same fluorescently labeled biomolecules under the same conditions.

Tissue culture experiments (Example 12, and FIGS. 4A, 4B, 6A, 6b, 6C, 7 and 8) have demonstrated that the conjugates described herein are more cytotoxic to cancer cells (representing various tumor types) than a mixture of the kinase inhibitor and the dye at equivalent concentrations.

In certain embodiments (e.g., wherein R13 and R14 are iodine), conjugates described herein are useful in photodynamic therapy (PDT). In PDT, dyes (sensitizers) are excited electronically by ultraviolet or visible radiation, and in their excited triplet states interact with endogenous oxygen to produce singlet oxygen. Singlet oxygen is extremely reactive, and is capable of killing cells. The half-life of singlet oxygen in tissue is extremely short, so the cell killing effect is tightly localized to the tissue area that contains the sensitizer, oxygen, and which is illuminated with light at a wavelength the sensitizer can absorb. Applications of PDT include cancer therapy, eradication of pathogens, and treatment of acne.

With regard to cancer therapy, tumors are usually obscured by a patient's healthy tissue and/or bone. One of the main factor limiting clinical development of sensitizers for PDT is the difficulty of getting light to tumors obscured by other tissues. For PDT, tissues are optimally permeable to light in the range 750-800 nm. If the wavelength is too long then photons do not contain sufficient energy to generate singlet oxygen. There are very few sensitizers for PDT that can efficiently capture light in the 750-800 nm range; all the FDA approved dyes for PDT are porphyrins that absorb at significantly shorter wavelengths. Many cyanine-7 (Cy-7) dyes absorb in the 750-800 nm range. However, cyanine dyes that do not contain "heavy atoms" (eg iodine and bromine) have poor efficiencies for conversion of light into singlet oxygen.

Accordingly, in one aspect, provided herein is a method of inhibiting the proliferation of a cancer cell, the method comprising contacting the cell with a conjugate as described herein (e.g., a conjugate of Formula (I), (Ia), (Ib), (Ic), (Id), (Ie), (If), (Ig), (II), (IIa), (IIb), (IIc), (IId), (IIe), (IIf), (IIg), or pharmaceutically acceptable salts thereof).

In certain embodiments, said inhibiting the proliferation of a cancer cell results in the death of the cancer cell (e.g., via apoptosis).

In certain embodiments, the cell is in vitro. In certain embodiments, the cell is in vivo.

In another aspect, the present disclosure provides a method of treating a proliferative disease in a subject in need thereof, the method comprising administering to the subject an effective amount (e.g., therapeutically effective amount) of a conjugate as described herein. In a particular embodiment, the proliferative disease is cancer.

In yet another aspect, the present disclosure provides a method of treating cancer in a subject in need thereof, the method comprising administering to the subject a conjugate as described herein.

In certain embodiments, the above methods further comprise irradiating the conjugate. In certain particular embodiments, said irradiation results in fluorescence of the cyanine dye moiety, wherein the fluorescence emission is at least 700 nm.

In certain particular embodiments of the above methods, the subject is human.

Pharmaceutical Compositions and Kits

One aspect of the present disclosure relates to pharmaceutical compositions that comprise a conjugate as described herein, and optionally a pharmaceutically acceptable excipient. The pharmaceutical compositions described herein may be useful in treating and/or preventing in a subject in need thereof proliferative diseases, such as cancer. The pharmaceutical compositions described herein may further be useful in inhibiting the proliferation of a cell, and/or reducing, delaying, and/or preventing the resistance of a cell to a kinase inhibitor.

Also encompassed by the disclosure are kits (e.g., pharmaceutical packs). The kits provided may comprise a conjugate described herein, or a pharmaceutical composition described herein. The kits may comprise a conjugate in a first container. The kits may comprise a pharmaceutical composition in a first container. In some embodiments, the kits further include a third container comprising a pharmaceutical excipient for dilution or suspension of the conjugate and/or pharmaceutical composition. Each of the first container, second container, and third container may independently be a vial, ampule, bottle, syringe, and/or dispenser package, or other suitable container. In certain embodiments, the kits are useful for treating a proliferative disease (e.g., cancer) in a subject in need thereof. In certain embodiments, the kits are useful for preventing a proliferative disease (e.g., cancer) in a subject in need thereof. In certain embodiments, the kits are useful for reducing, delaying, and/or preventing in a subject in need thereof the resistance of a proliferative disease to a kinase inhibitor. In certain embodiments, the kits are useful in inhibiting the proliferation of a cell. In certain embodiments, the kits are useful in reducing, delaying, and/or preventing the resistance of a cell to a kinase inhibitor. In certain embodiments, a kit described herein further includes instructions for using the conjugate included in the kit, or for using the pharmaceutical composition included in the kit. A kit described herein may also include information as required by a regulatory agency such as the U.S. Food and Drug Administration (FDA). In certain embodiments, the information included in the kits is prescribing information. A kit described herein may include one or more additional pharmaceutical agents described herein as a separate composition.

REFERENCES

1. L. W. K. Chung, R. Wang, H. E. Zhau, L. Strekowski, M. Henary, G. Patonay, J. J. Krutak, X. Yang, and G. Zhu, (Emory University, USA). Cyanine-containing compounds for cancer imaging and treatment sumission 1 Jul. 2015, 2015, patent US 20150183736A1.
2. L. W. K. Chung, R. Wang, H. E. Zhau, L. Strekowski, M. Henary, G. Patonay, J. J. Krutak, X. Yang, and G. Zhu, (Emory University, USA). Cyanine-containing compounds for cancer imaging and treatment sumission 3 Dec. 2017, 2017, patent US20170354747A1.
3. L. W. K. Chung, R. Wang, H. E. Zhau, L. Strekowski, M. Henary, G. Patonay, J. J. Krutak, X. Yang, and G. Zhu, (Emory University, USA). Cyanine-containing compounds for cancer imaging and treatment sumission 2 Nov. 2015, 2015, patent US20150335765A1.
4. Surface charge-mediated rapid hepatobiliary excretion of mesoporous silica nanoparticles, J. S. Souris, C.-H. Lee, S.-H. Cheng, C.-T. Chen, C.-S. Yang, J.-a. A. Ho, C.-Y. Mou, and L.-W. Lo, Biomaterials, 2010, 31, 5564-74.
5. Near IR Heptamethine Cyanine Dye-Mediated Cancer Imaging, X. Yang, C. Shi, R. Tong, W. Qian, H. E. Zhau, R. Wang, G. Zhu, J. Cheng, V. W. Yang, T. Cheng, M. Henary, L. Strekowski, and L. W. K. Chung, Clin. Cancer Res., 2010, 16, 2833-44.
6. Small-molecule kinase inhibitors: an analysis of FDA-approved drugs, P. Wu, T. E. Nielsen, and M. H. Clausen, Drug Discov Today, 2016, 21, 5-10.
7. FDA-approved small-molecule kinase inhibitors, P. Wu, T. E. Nielsen, and M. H. Clausen, Trends Pharmacol. Sci., 2015, 36, 422-39.
8. Targeting cancer with kinase inhibitors, S. Gross, R. Rahal, N. Stransky, C. Lengauer, and P. Hoeflich Klaus, J Clin Invest, 2015, 125, 1780-9.

Heptamenine Cyanine Dye QCy

As compared to MHI-148, structure QCy differs in isoelectric substitution of a methylene carbon atom with a dimethyl quaternary ammonium nitrogen.

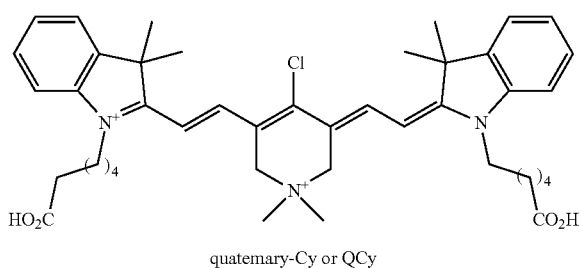

quaternary-Cy or QCy

-continued

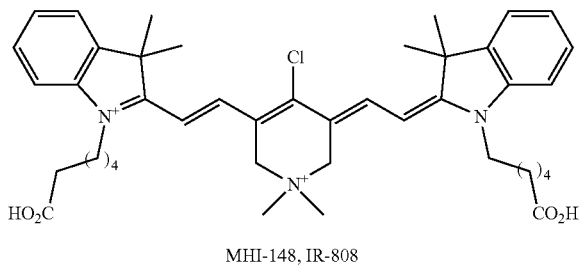

MHI-148, IR-808

That simple modification changes several fundamental properties of the dye in a significant way. Relative to MHI-148, QCy has one greater positive charge at all ionization states since the quaternary ammonium is cationic at all physiological pH values. QCy is more water soluble than MHI-148, but its solubility characteristics are more complex and interesting that anticipated. Data presented below show that QCy is, in fact, also less prone to aggregation in aqueous media than MHI-148. Intriguingly, testing of some known unknowns for QCy also revealed potentially useful photophysical and physiological characteristics that could not have been foreseen prior to experimentation.

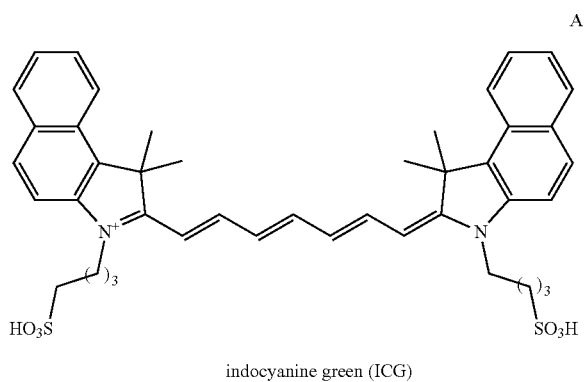

indocyanine green (ICG)

Figure 36A:
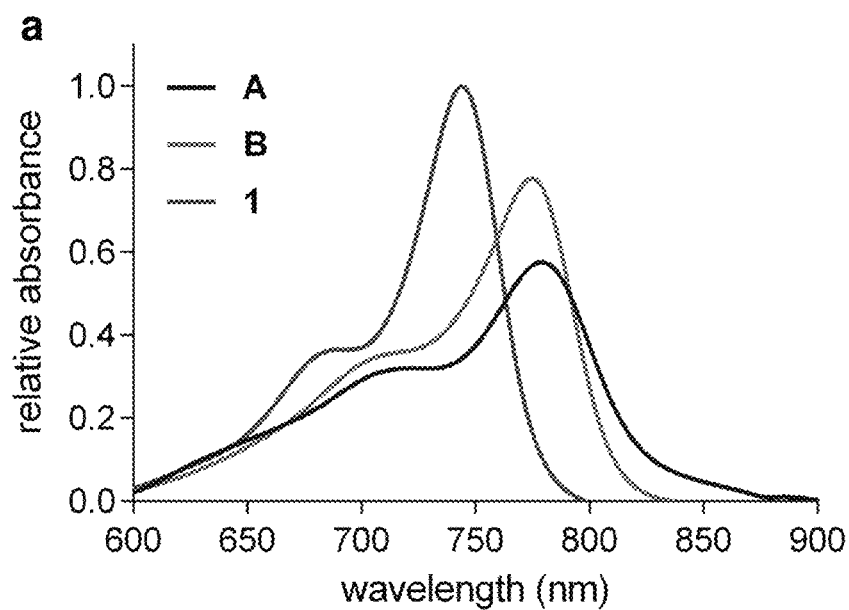
FIGS. 36A and 36B show relative absorbance (a) and fluorescence (b) of 5 μM (A) ICG, (B) MHI-148, and (1) QCy in 10 mM pH 7.4 phosphate buffer saline (PBS).
Figure 36B:
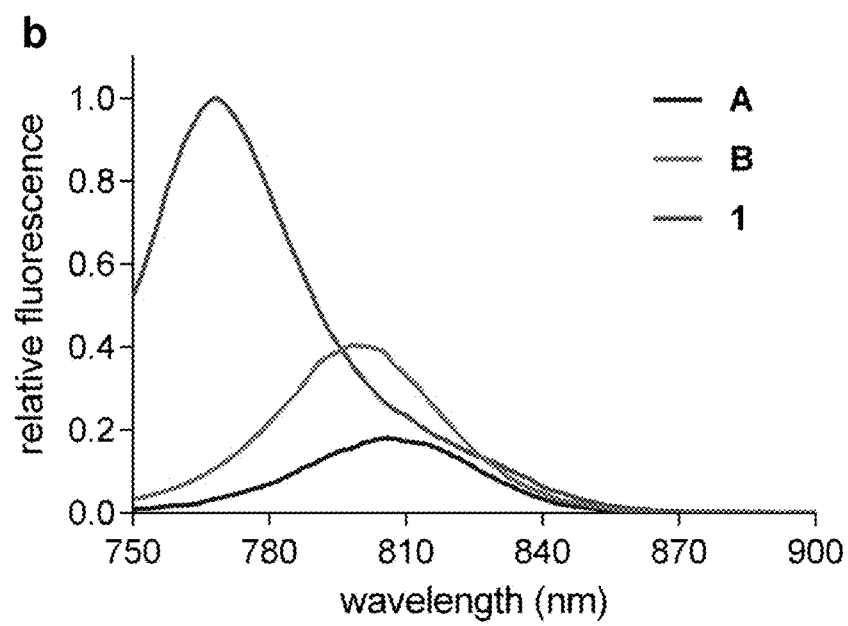

FIG. 36A-B shows the absorbance (a) and fluorescence (b) of equimolar solutions of fluors ICG, MHI-148, and QCy. Qualitatively, these data show that QCy has a greater absorbance than ICG or MHI-148, and its fluorescence brightness was markedly higher than the other two fluors. Fluorescence maxima for these three compounds shift to longer wavelengths in the order QCy<MHI-148<ICG, i.e., ICG has the most red-shifted absorbance maximum.

These qualitative observations made above are supported by quantitative measurements of select photophysical characteristics of these fluors (Table 1). They have approximately the same Stokes' shifts (23-28 nm), but the extinction coefficients and fluorescence quantum yields are different, and both parameters follow the order QCy>MHI-148>ICG. More specifically, the absorbance of ICG is only about 60% of that of QCy, and the fluorescence quantum yield for QCy is about three times greater; data for B are intermediate.

The quantum yield of all three dyes ICG, MHI-148, and QCy is not even close to 1%. A common misconception when evaluating quantum yields is to compare near-IR fluors with dyes excited at lower wavelengths. Lower quantum yields are expected in the near-IR region because bond stretches and deformations tend to be favored relative to electronic transitions for long wavelength incident light. Consequently, modifications to near-IR dyes that result in quantum yield increases from, for instance, 1 to 3% should be viewed as a 300% improvement, and not in the context of P values for dyes that are excited at much shorter wavelengths. Table 1 indicates the brightness of QCy is over five-fold greater than ICG.

TABLE 1

Comparative photophysical properties of ICG, MHI-148 and QCy in 10 mM PBS buffer pH 7.4

| compound | $\lambda_{abs}$ (nm) | $\lambda_{em}$ (nm) | $\Delta\lambda^a$ | $\varepsilon_{max}$ (cm$^{-1}$M$^{-1}$) | $\Phi^b$ | brightness ($\varepsilon_{max} \times \Phi$) | relative brightness |
|---|---|---|---|---|---|---|---|
| ICG | 779 | 807 | 28 | 111060 | 0.017 | 1941 | 1.00 |
| MHI-148 | 775 | 799 | 24 | 149940 | 0.025 | 3689 | 1.90 |
| QCy | 745 | 768 | 23 | 192460 | 0.051 | 9901 | 5.10 |

[a]Stokes' shifts of A, B and 1.
[b]Fluorescence quantum yield were performed using A ($\Phi$ = 0.13 in DMSO) as a standard.

Figure 37A:
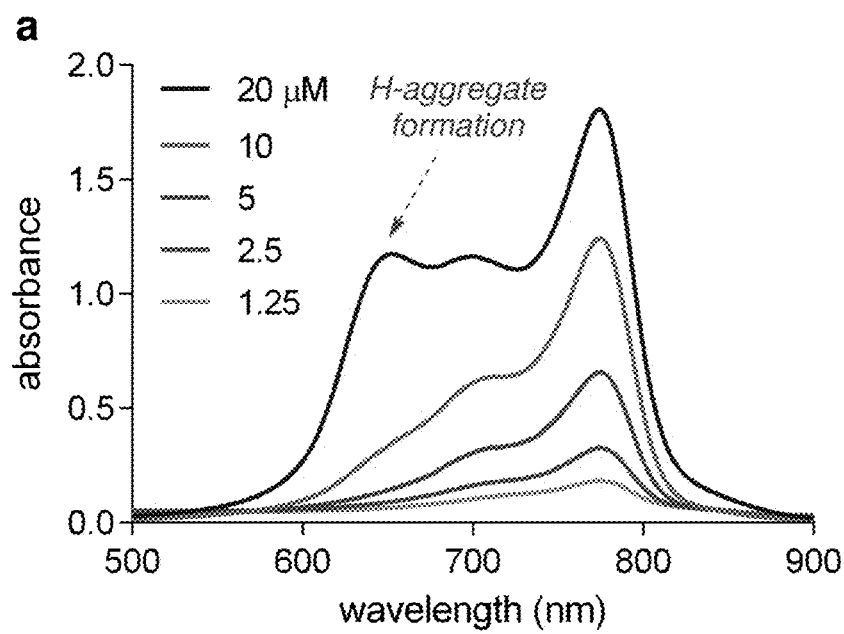
FIGS. 37A and 37B show concentration dependence of absorbance spectra in the range 1.25-20 μM in 10 mM pH 7.4 PBS buffer a, (B) MHI-148 and b, (1) QCy.
Figure 37B:
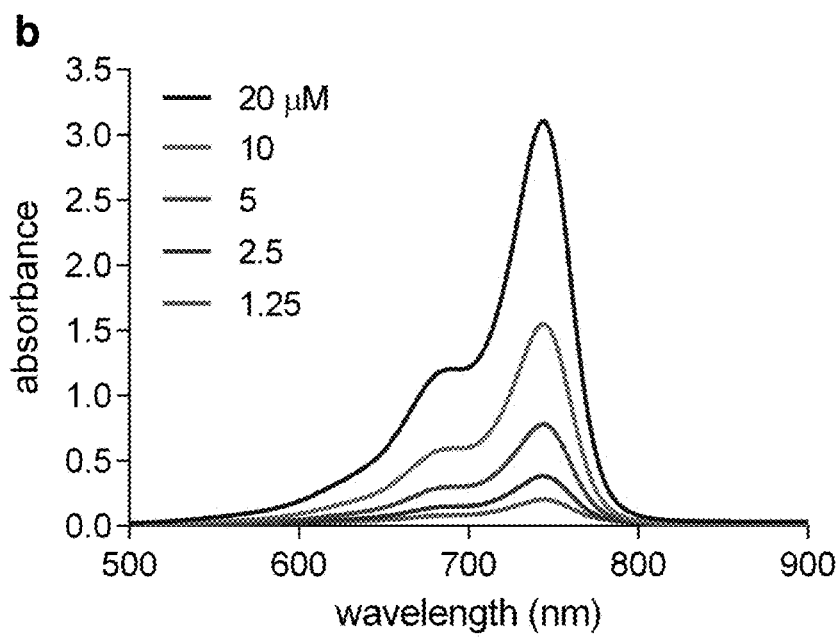

A blue-shifted shoulder is apparent for all three dyes in their absorbance spectra shown in FIG. 36B. Shoulders of that kind and indicative of H-aggregates, ie associative oligomers in which the transition moments of the monomers are not well aligned leading to bathochromic (blue) shifts. Concentration dependences of absorbance spectra of QCy and MHI-148 (structurally the closest) were determined to explore H-aggregation further. It emerged (FIG. 37) that QCy is considerably less aggregated than MHI-148; cf the shoulder for QCy is less pronounced and blue-shifted than MHI-148 at all concentrations.

Figure 38:
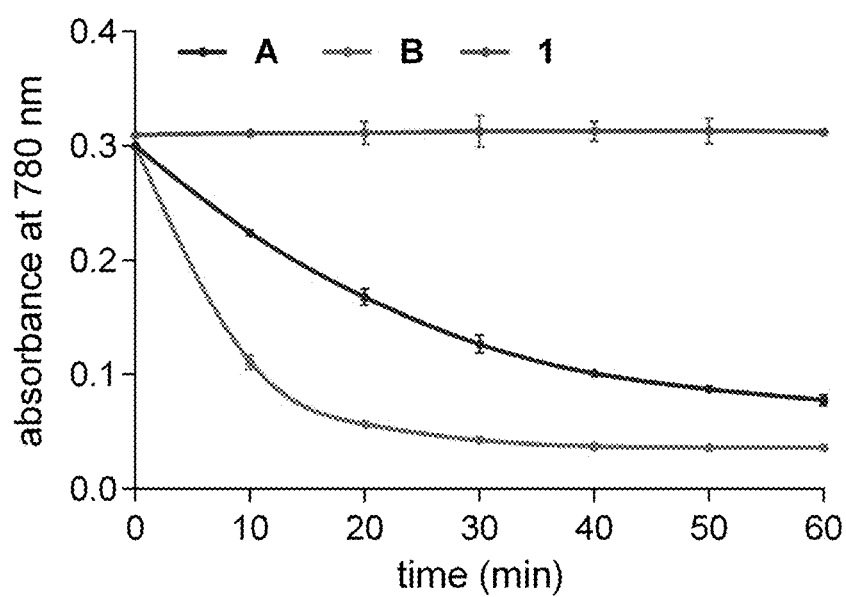
FIG. 38 shows photostabilities of (A) ICG, (B) MHI-148, and (1) QCy (in the approximate range 5-30 μM, dilutions chosen such that each solution had the same absolute absorbance at 780 nm) in 10 mM pH 7.4 PBS buffer at 780 nm (Thor Lab, LED780E). Compound 1 was the most photostable whereas B was the least stable and decomposed (t½<10 min).

Solutions of fluors ICG, MHI-148, and QCy in PBS buffer open to the air were illuminated at 780 nm with an LED. Initially, equimolar concentrations (20 μM) were used; QCy was reproducibly and more robust than the other two, but the difference was more than anticipated so the experimental design was suspected. Hypothesizing that the difference observed could be because QCy simply absorbs less quanta at 780 nm (recall, its absorbance maxima is blue-shifted relative to ICG and MHI-148, Table 1), the experiment was repeated using solutions diluted to have the same absorbance at 780 nm. These experiments (FIG. 38) gave essentially the same data, except that ICG and MHI-148 decomposed at different rates, but still QCy proved markedly more stable. Under these conditions QCy shows almost no decomposition after 1 h continuous illumination.

Figure 39:
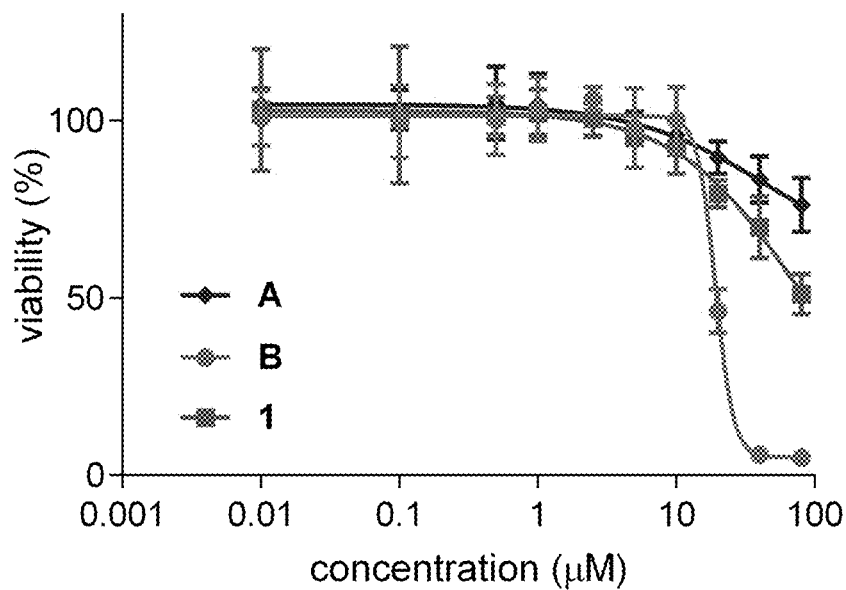
FIG. 39 shows cytotoxicity of compound (A) ICG, (B) MHI-148, and (1) QCy on U87-MG cells after incubating with the test compounds for 72 h in the dark, before an AlamarBlue test for cell viability. Cyanine B was toxic at (IC50 value=19.1±1.01 μM) but compound A and 1 were not very toxic until 80 μM.

Cytotoxicity of QCy was studied using U87-MG cells (a glioblastoma multiforme line). FIG. 39 illustrates that both ICG and QCy were significantly less cytotoxic than MHI-148 (IC$_{50}$ value=19.1±1.01 μM). Values for the IC$_{50}$ of ICG (not significantly cytotoxic up to 80 μM) and QCy (IC$_{50}$>80 μM but could not be measured since this fluor is not soluble at higher concentrations. The lower cytotoxicity of QCy is an advantage in clinical imaging.

Confocal imaging experiments were performed with ICG, MHI-148, and QCy to check for colocalization with the four tracking probes found to be most pertinent: i.e., for localization in mitochondria, lysosomes, the endoplasmic recticulum (ER), and golgi. Compound QCy initially accumulated in the golgi (after 30 min incubation) but after an extended period (24 h) it was found primarily in the lysosome and ER. Similar experiments were performed for ICG and MHI-148; that data is summarized in Table 2.

TABLE 2

Organelle localization of the fluors in U87-MG glioblastoma cells at relatively short and long time intervals after incubation with the cells at 37° C. in DMEM/F12 supplemented by 10% FBS pH 7.4.

| fluor | localization after time (h) | |
|---|---|---|
| | 0.5 | 24 |
| ICG | golgi and ER | golgi and lysosome |
| MHI-148 | mitochondria | mitochondria and lysosome |
| QCy | golgi | lysosome and ER |

Mechanisms of Uptake of Cyanine Dyes

Indocyanine green (ICG, A), a heptamethine cyanine or "Cy-7" dye, is the only near-IR FDA-approved optical marker for clinical use.[1,2] ICG is used in surgical procedures because of its favorable safety profile,[3-5] and because it is fluorescent with an absorbance maximum around 750 nm. Below 750 nm, excitation of dyes obscured by more than a few millimeters of tissue becomes impractical with even the highest laser powers acceptable in surgical settings. To calibrate, penetration of light wavelength 800 nm is twice that of light 630 nm.[6]

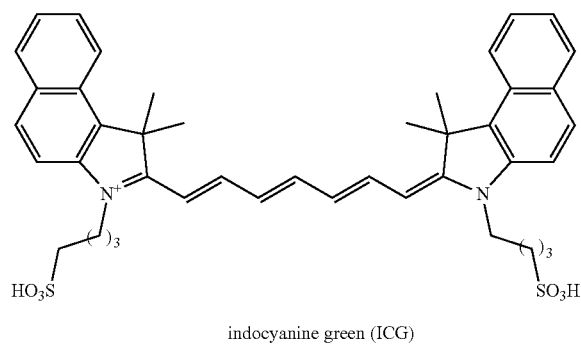

indocyanine green (ICG)

A

Fluor A can be used in surgery, but it is not disposed to especially accumulate in cancer tissue. In fact, ICG collects in the liver and gastrointestinal tract, and tends to mostly wash out of the body within a few hours.[7] However, at least in animal models, other heptamethine cyanine dyes like 1-Cl and B-D do accumulate in solid tumors (eg prostate,[8] gastric,[9] kidney,[10] hepatocytes,[11,12] kidney,[10] lung cancer,[13] and glioblastoma[14]) but not in normal cells and tissue.[5-19] Moreover, fluors B-D tend to persist in those tumors; they can still be observed there after 1-2 days.

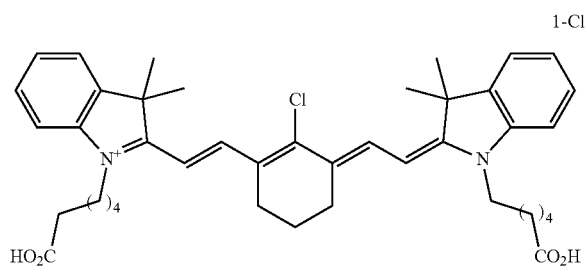

MHI-148, IR-808

1-Cl

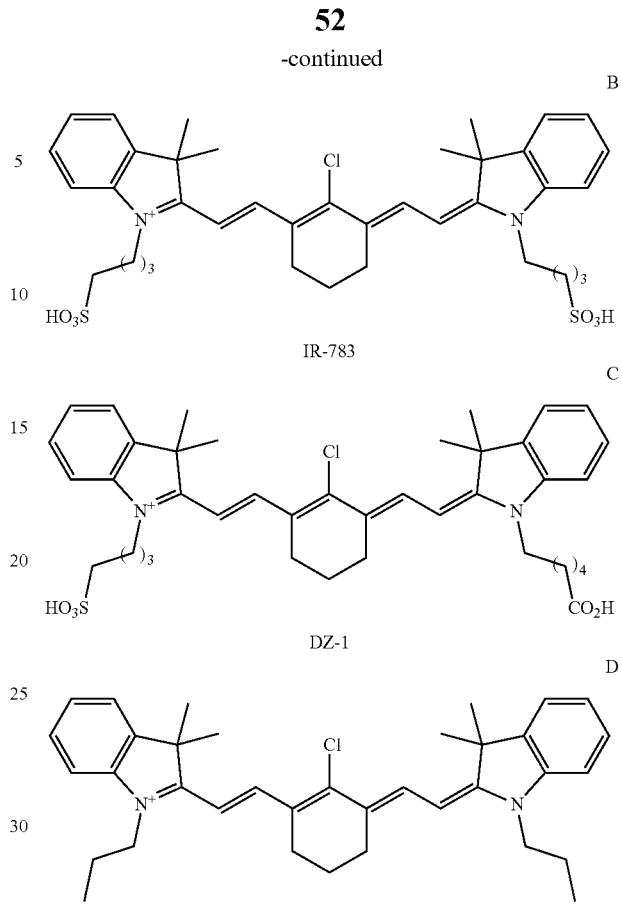

IR-783

B

DZ-1

C

IR-780

D

Many reports (for example[8,10,11,13-16,19,20]) explain the "tumor-seeking" characteristics of fluors 1-Cl and B-D in terms of uptake via the Organic Anion Transporter Proteins (OATPs).[21,22] Hypoxia (common in compressed solid tumors) triggers activation of HIF1 □, and promotes OATPs overexpression in cancer tissue relative to levels found in normal cells.[9,20] The natural role of OATPs is to mediate influx organic anions and some neutral materials that are important to cells (eg bile salts, steroids, bilirubin, and thyroid hormones). This diversity of substrates means OATPs are not particularly selective and, coincidentally, these receptors also import some drug structures and fluors 1-Cl, B-D. To balance this ion influx, OATP receptors efflux intracellular bicarbonate, glutathione, and glutathione adducts. Consequently, OATP receptors can promote influx of fluors 1-Cl, B-D into cells, without pumping the same ones out.

A chance discovery led the assumption that import via the OATP receptors predominantly accounts for the tumor-seeking characteristics of fluors 1-Cl, B-D to be questioned. In the event, data presented in this paper indicates that OATP receptors are a mechanism of import in ex vivo cellular experiments, but an alternative mechanism accounts for the persistent fluorescence of tumors in animal experiments featuring fluors of this category.

The following is a typical literature procedure for treatment of cancer cells with fluor 1-Cl. The cells (in the present case a leukemia line, K562) are suspended in RPMI-1640 with 10% FBS medium added, then seeded to 24-well plates. Various concentrations of 1-Cl in the same medium are added to the cells to give final fluor concentrations of 0-30

μM. After 20 h incubation at 37° C., the cells are collected, and washed twice with ice-cold PBS buffer.

In a particular experiment, RIPA lysis buffer containing of 1% of a pan protease inhibitor was added to the cells after the procedure outlined above. The cell samples were gently shaken on ice for 30 min, and the lysates were centrifuged to remove cell debris. Supernatants were collected and the protein concentrations were determined using a colorimetric protein assay kit. Equal total protein amounts were electrophoresed under reducing conditions on 15% SDS-PAGE. The gel was washed with de-ionized water, then analyzed with an imager designed to detect the near IR fluorescence (>800 nm); this gave a conspicuous fluorescent band at over 50 KDa. The selectivity with which this band formed was surprising.

Figure 40A:
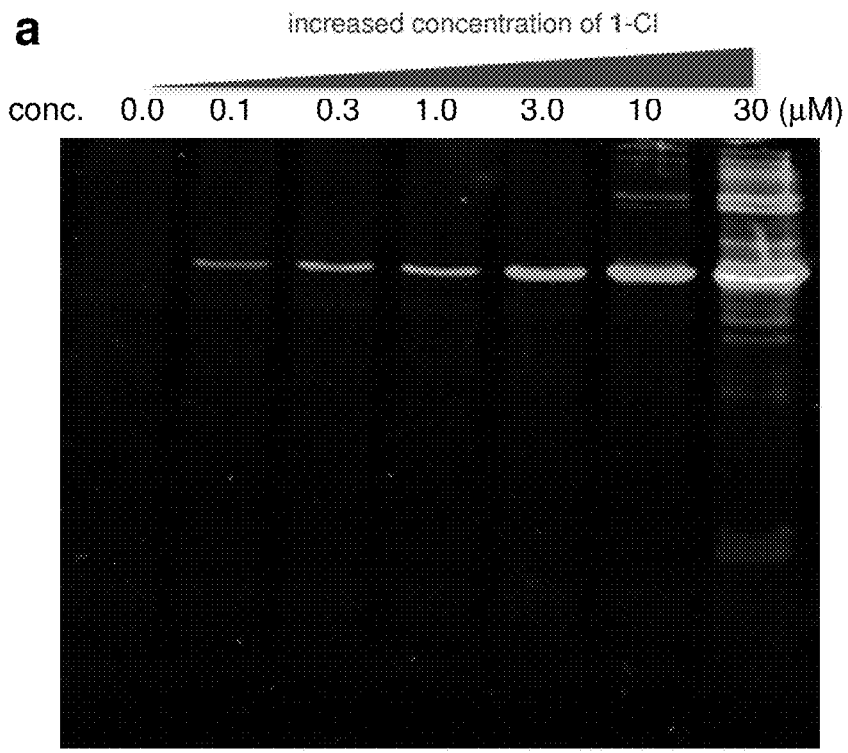
FIG. 40A shows NIR-fluorescent gel image (>800 nm) K562 cell lysate prior treated with different concentrations of 1-Cl for 20 h in RPMI-1640 media containing 10% FBS.
Figure 40B:
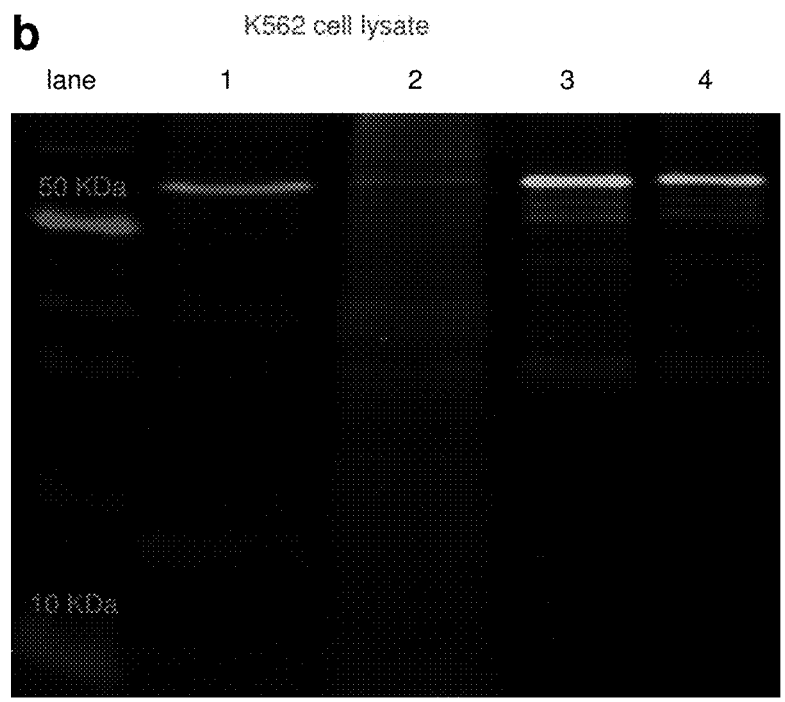
FIG. 40B shows Lane 1, K562 cell lysates treated with 10 μM of 1-Cl as in FIG. 40A. Lane 2, K562 cell lysates treated with 10 μM of 1-Cl as in FIG. 40A except serum-free RPMI-1640 media was used. Lane 3, 10 μM of 1-Cl incubated with RPMI-1640 media containing 10% FBS for 20 h as in FIG. 40A but without cells. Lane 4, 10 μM of 1-Cl as in FIG. 40A, except no cells were used and bovine serum albumin 10 μM BSA was added in their place. Staining the gel with Coomassie Blue showed an equal amount of protein was loaded into each well.

After a few false starts, it was hypothesized that the pronounced fluorescent band in the gel shown in FIG. 40A was derived from bovine serum albumin (BSA) in the FBS medium. Consistent with this assertion, FIG. 40B shows the band from the lysate (lane 1) was not formed when FBS was excluded from the culture medium (lane 2), but it was formed when FBS was present without cells, or when only BSA was added (ie no cells and no FBS; lanes 3 and 4, respectively). Albumin concentrations in FBS vary between 20-36 mg/mL;[23-25] assuming a conservative mid-range figure of 25 mg/mL BSA in FBS, this corresponds to 38 μM. Thus cellular experiments involving 10 μM 1-Cl would have almost a four-fold excess of BSA (38 μM) to react with.

Figure 40C:
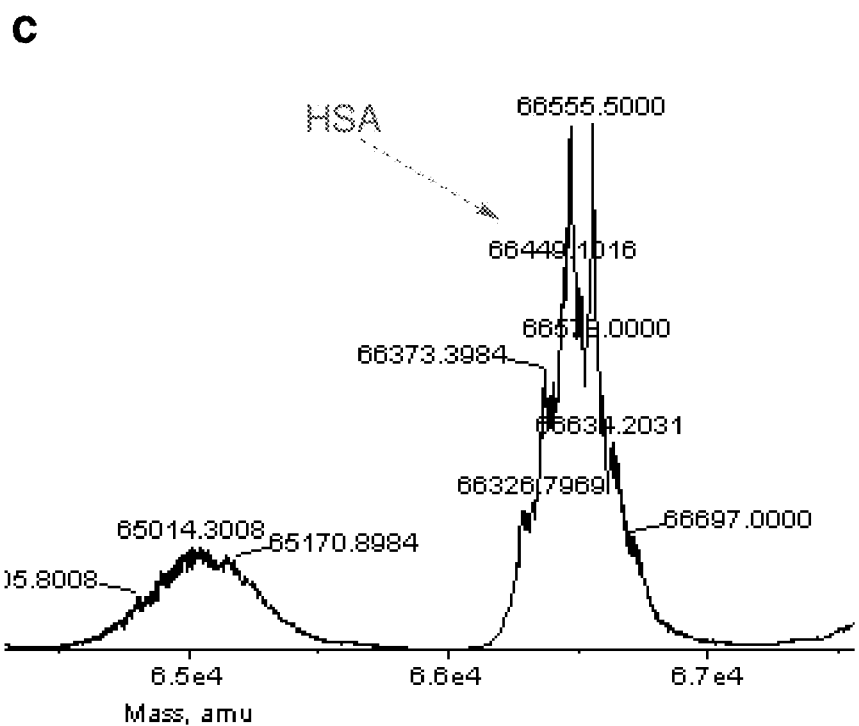
Figure 40D:
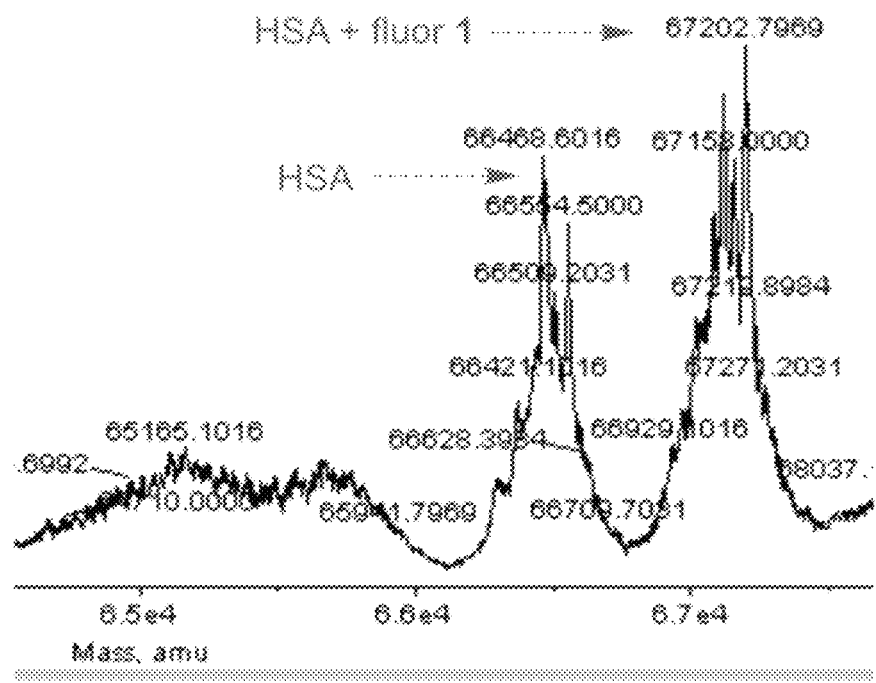
FIG. 40D, ESI MS of 1-Cl covalently bound to HSA formed by reacting the two components in a 2.5:1 ratio (1 M HEPES buffer).

In a control experiment, human serum albumin (HSA) was reacted with 2.5 equivalents of 1-Cl at 37° C. in 1 M HEPES buffer. This 1-Cl:albumin molar ratio was selected because it is approximately that used in cell culture experiments to probe uptake of this dye. FIG. 40C shows the ESI mass spectrum of HSA, and FIG. 40D shows that for a product formed when HSA combined with 1-Cl; the molecular masses formed correspond to a 1:1 covalent adduct between 1-Cl (after loss of $C_1$) and HSA. This is consistent with the fact that HSA has one free Cys residue (and 34, oxidized, ie disulfide-linked, Cys residues); see Discussion.

Figure 41A:
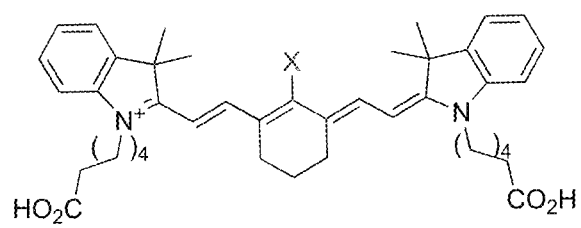
FIG. 41A shows structures of 1-Cl and meso-blocked derivatives.

At this stage it was hypothesized that the 1:1 covalent adduct is formed by displacement of the meso-$C_1$ from 1 by a nucleophile on HSA, and that nucleophile was probably the free Cys thiol. Three derivatives of 1 that had meso-functionalities that cannot readily be leaving groups were made and reacted with HSA to test a meso-leaving group was required for covalent binding. It emerged (FIG. 41A) that ICG (A) 1-H, 1-Me, and 1-Ph do not react with HSA at 37° C. in aqueous buffer, under the conditions that 1-Cl does combine with HSA (FIG. 41B); in fact, nearly all the 1-Cl is consumed after 72 h.

At this stage it seemed probable that 1-Cl reacts with a free thiol on albumin. To exclude the possibility that other nucleophilic amino acid side-chains might be involved (eg Lys, Tyr, Ser) experiments were performed using HSA that was first treated with 6-maleimide-hexanoic acid to selectively blocks free thiols.[26,27] Unexpectedly, this experiment still gave a fluorescent band, but it was concluded that there was some 1-Cl non-covalently bound to albumin, and this became covalently bound after the protein had been reduced for loading onto the gel. To test this assertion the experimental design was modified in the following way. HSA was first completely reduced with tris(2-carboxyethyl)phosphine (TCEP) to break all its disulfide bonds, then the product was thiol-blocked using 6-maleimide-hexanoic acid (15 μM, 1 μg in the protocol outlined in FIG. 41D), and finally this sample was treated with 1-Cl. This approach is imperfect because it tests the interaction of 1-Cl with reduced albumin, but it is sufficient to prove that 0- and N-based nucleophilic side-chains (specifically those not those derived from cysteine) of the reduced protein did not combine with 1-Cl. Thus, binding of free Cys to 1-Cl is implicated in the covalent binding step.

Non-covalent interactions of the dyes 1 with HSA were also explored. Thus, 10 μM solutions of ICG, 1-Cl, 1-H, 1-Me and 1-Ph were mixed with varied concentrations of HSA and the interaction was followed by UV spectroscopy. Absorbance saturation was observed for 1-Cl at a 1:1 ratio with HSA, but for the other compounds 1, none of which have a leaving group at the meso-position, saturation was achieved at around 1.5 equivalents of HSA.

Uptake of Fluor 1-Cl and 1-HSA into Cells

Figure 41B:
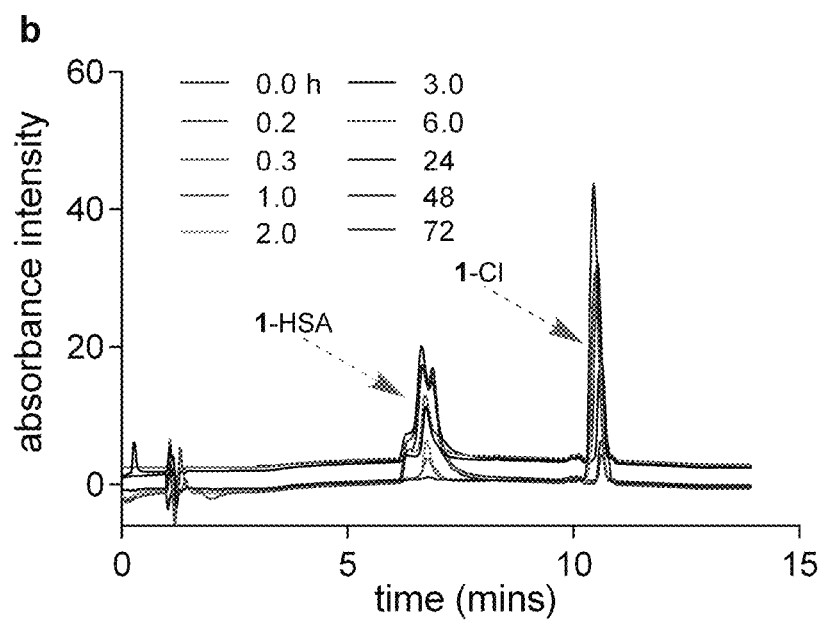
Figure 41C:
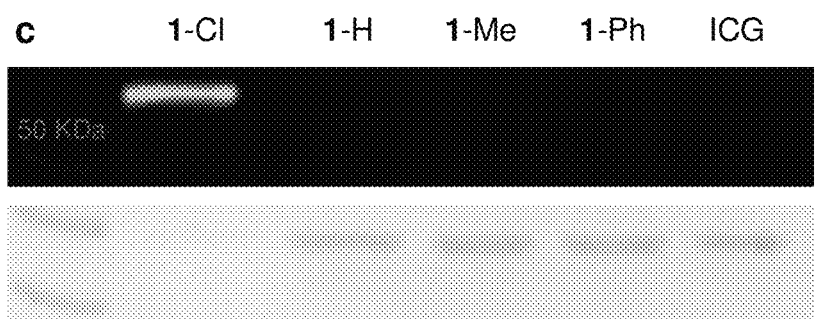
FIG. 41C HSA (1 μM, 1 μg) incubated with cyanines 1 (10 μM) for 3 h in 50 mM pH 7.4 HEPES buffer; and, FIG. 41D HSA (15 μM, 1 jag) and "thiol-blocked HSA" (see text) treated with 1-Cl (15 μM) for the incubation times indicated.
Figure 41D:
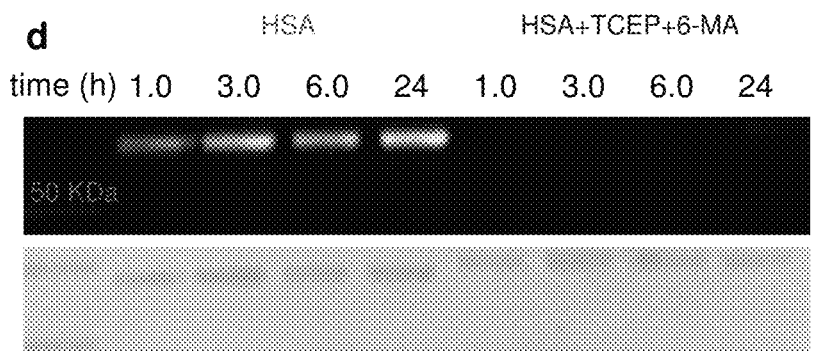

FIG. 41B indicates that albumin and 1-Cl at approximately the ratio typically used in cell culture experiments (2.5:1.0, see above) react over time periods that are similar to the span of a typical cell culture experiment. Consequently, it was tested first where the fluorescent signal localizes in cells if albumin is excluded from the media, then determined if 1-HSA is imported and, if so, where it localizes.

Figure 42:
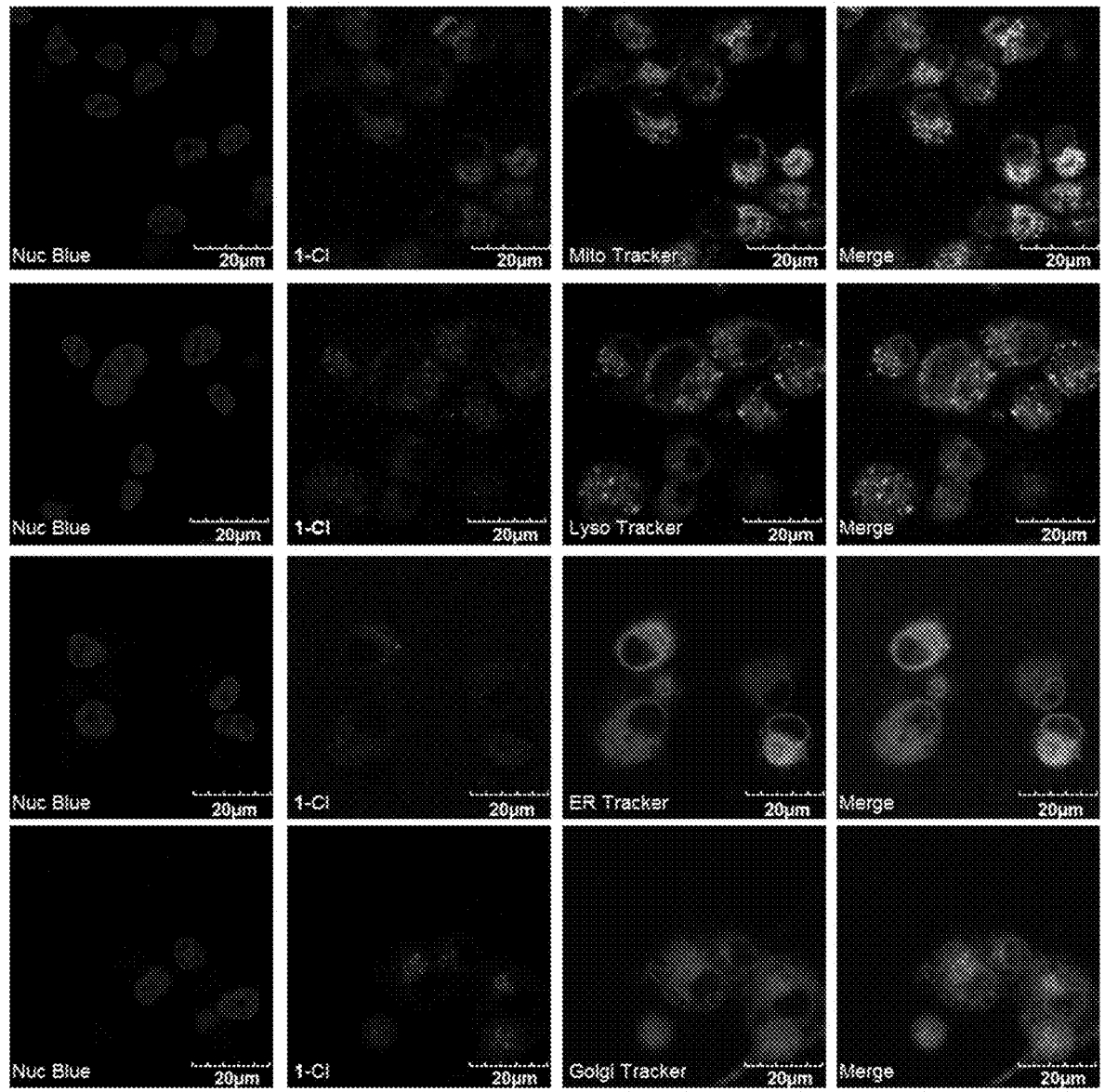
FIG. 42 shows uptake of 1-Cl (20 μM) into U87-MG cells incubated in serum free media for 30 mins. Colocalization with trackers for mitochondria, lysosome, ER and Golgi are featured. Images were taken using Zeiss confocal microscope at 60×/1.2 water immerse objective after 30 mins of incubation. Most colocalization is seen with the mitochondria.

FIG. 42 shows confocal images for uptake of 1-Cl into a human glioblastoma cell line (U87-MG) cultured in a medium not containing albumin. Under these conditions the dye was imported into the cells at the time of the experiment (30 min incubation), and it localized in the mitochondria.

Figure 43:
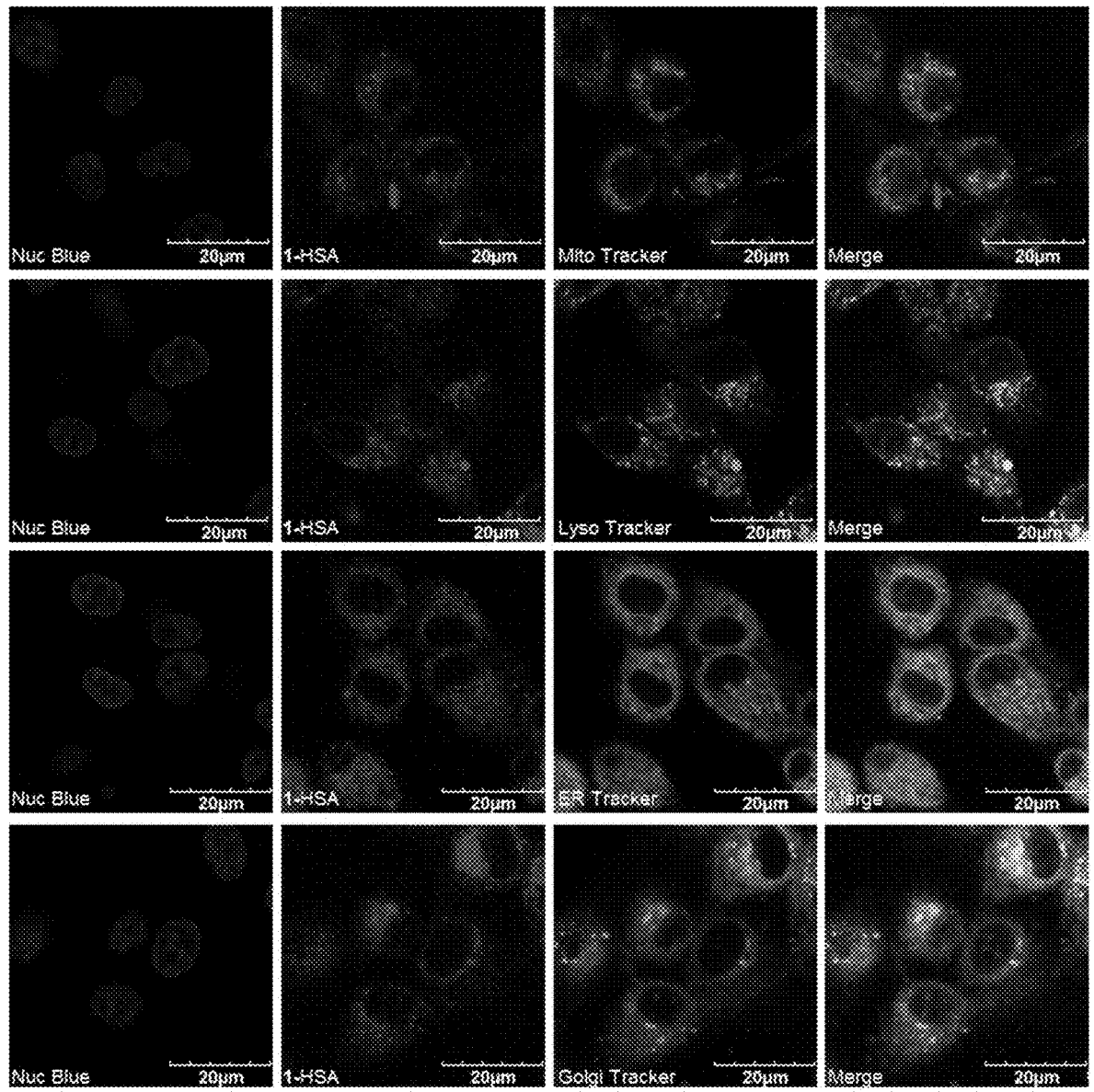
FIG. 43 shows uptake of 1-HSA (20 μM) into U87-MG cells incubated in serum free media. Colocalization with trackers for mitochondria, lysosome, ER and Golgi are featured. Images were taken using Zeiss confocal microscope at 60×/1.2 water immerse objective after 30 mins of incubation. Most colocalization was seen with lysosome and Golgi.

FIG. 43 are data from a set of experiments nearly identical to those in FIG. 42, except featuring preformed 1-HSA (ie not 1-Cl), also in media not otherwise containing albumin. At 30 min of incubation, it was clear that 1-HSA was also imported into the cells, but this adduct preferentially localizes in the lysosome and Golgi, ie different organelles to 1-Cl.

Data in FIG. 42 should be compared with literature reports describing import of 1-Cl but in media containing albumin into various cells. For instance, the following cell lines have been tested, and localization was observed in the mitochondria: human cervical cancer cell line (HeLa) and Lewis lung carcinoma (LLC), rat transformed mesenchymal stem cells (rTDMCs).[19] Uptake of 1-Cl was also investigated but in media containing albumin into U87 glioblastoma cells and found fluorescence was observed mostly in the mitochondria.

The evidence for OATP receptor mediated uptake of 1-Cl in tissue culture is based on the same experimental format. Briefly, cells are suspended in media (containing BSA) at 37° C., 1-Cl is added in the same medium, and after 20 h at 37° C. the cells are collected, and washed twice with ice-cold PBS buffer. Microscopy is then used to qualitatively monitor the uptake. This protocol is performed side-by-side with two similar experiments but where the media contains the pan-OATP inhibitor BSP (bromosulfophthalein),[28] or in which the cells were treated with an agent to induce hypoxia (DMOG, dimethyloxalylglycine[29,30]). Under these conditions, BSP suppresses the fluorescence observed in the cells (presumably by inhibiting OATP-mediated uptake), whereas under hypoxic conditions for which OATPs are overexpressed, the fluorescence uptake was increased. Next it was explored how 1-HSA would behave under these conditions because the data above indicates that at least partial conversion of 1-Cl to 1-HSA occurs in these types of cellular experiments featuring albumin in the media. These experiments would reveal if 1-HSA was imported into the cells and, if so, how its uptake responds to the pan-OATP inhibitor, BSP.

Figure 44:
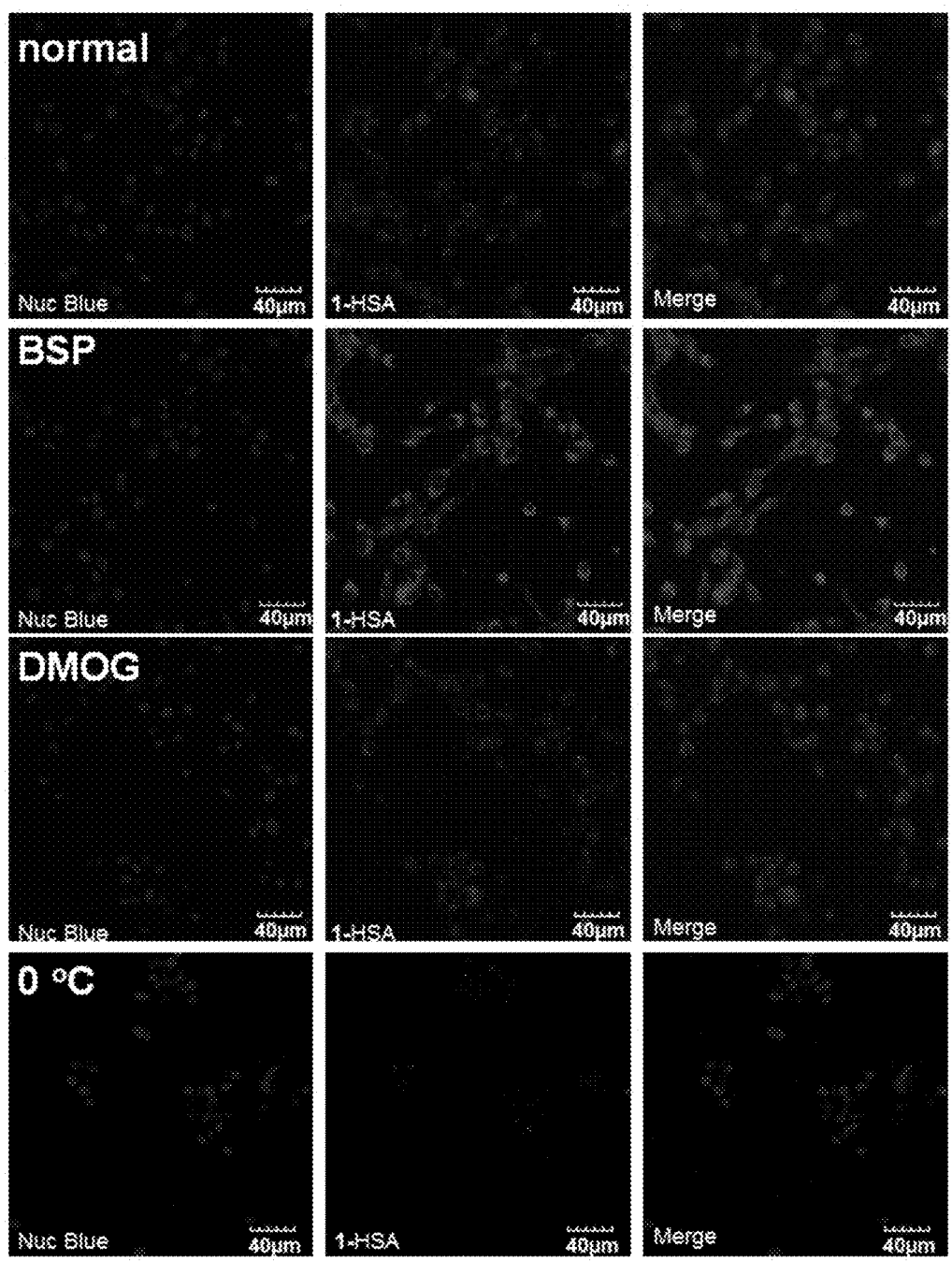
FIG. 44 shows experiments to test uptake of 1-HSA (20 μM) into U87-MG cells (grown in DMEM media supplemented with 10% FBS, ie containing approximately 0.038 mM BSA).

Data in FIG. 44 shows that 1-HSA is imported into the glioblastoma cells (first row). Import of 1-HSA is conspicuously increased when the cells are pretreated with pan-OATP inhibitor, BSP. Hypoxic and normoxic cells import about the same amount of fluorescence from 1-HSA (rows 3 and 1), but cooling the cells to retard active transport mechanisms also diminishes uptake of fluorescence from 1-HSA. Collectively these data shows uptake of 1-HSA is enhanced by active transport mechanisms, but not via the OATP receptors. Data from similar experiments show 1-HSA uptake was: (i) not inhibited by an inhibitor of clathrin mediated endocytosis (PitStop2); but it was by, (ii) a micopinocytosis inhibitor (amiloride): and by, (iii) an inhibitor of lipid raft endocytosis (M3CD).

Discussion

Figure 45:
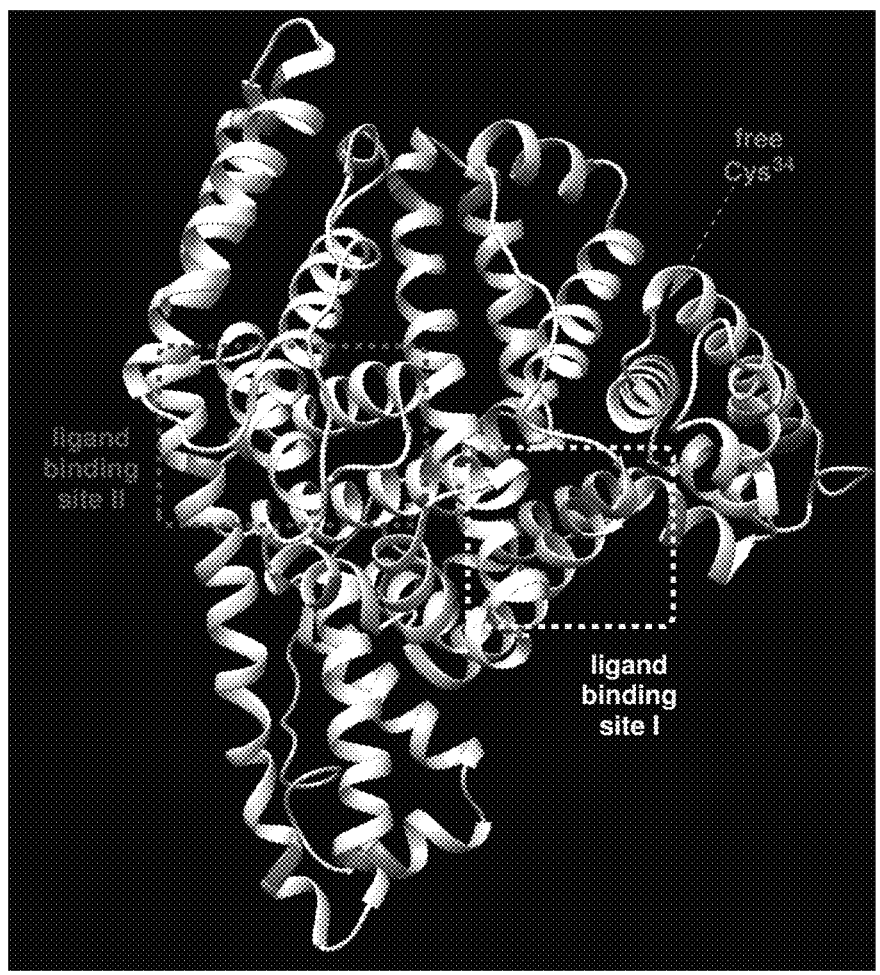
FIG. 45 shows HSA structure from PDB 1AO6.

Albumin (FIG. 45; from PDB 1AO6) has 14 disulfide bonds and one unique, free cysteine residue, Cys34. It is present in high concentrations in the blood where is acts as a carrier for small molecules, many of which non-covalently bind one of the two binding sides indicated. Consequently, electrophilic small molecules might react with Cys34 directly, or possibly associate with one of the binding sites then be relayed to that free thiol. Albumin is known to be imported into cells via several mechanisms[31] and particularly into cancer cells[32,33] though this does not include OATP receptor-mediated pathways.

Both non-covalent and covalent binding to albumin have dramatic effects on the pharmacokinetics of small molecules.[34,35] Some small molecule drugs associate with albumin;[36] this can be problematic if they are not released, but in other situations it is an advantage due to the prolonged half-life of the compound in the blood. Small molecules also have been covalently bound to albumin via Cys34 to improve their pharmacokinetics.[31] This is frequently achieved by attaching a maleimide functionality to the small molecule and either reacting it with HSA[37,38] or simply allowing the drug to combine with HSA in situ in a novel prodrug approach.[39-43] Albumin itself has been estimated to have a turn-over rate of over 20 days in humans,[44] so it seems likely that most covalent small molecule-to-albumin adducts would be long-lived in vivo.

Albumin is the most abundant protein in the blood, being present at around 35-50 g/L or 0.53-0.73 mM (human and mouse). It is estimated that 1-Cl injected into a 25 g mouse at 10 mg/Kg (a typical dose in an in vivo experiment featuring this dye), then the initial concentration in the blood also would be in the same range, ~0.53 mM. After the injection, clearance mechanisms would rapidly decrease the amount of free 1-Cl in the blood; consequently, excess albumin is always present. The present data indicates that 1-Cl would be converted to 1-HSA (and presumably to lesser amounts of adducts with other serum proteins like LDL) reasonably quickly.

There does not appear to be published in vivo work on the lifetime of 1-Cl in the blood, but a very careful study of the derivative D has reported the half-life of this compound in mice to be 36 min. Formation of covalent adducts to albumin and other serum proteins with free thiols[45] must account, at least in part, for the rapidly decreasing 1-Cl concentration in the blood in that study. Assuming the same half-life for 1-Cl, and considering that the blood circulates in about one minute, it is reasonable to conclude some 1-Cl does enter cancer cells in vivo shortly after administration iv. However, once inside the cells then 1-Cl encounters high concentrations of other nucleophilic thiols, notably, glutathione. In work performed in parallel to this, it has also been proved that 1-Cl has a similar reactivity towards Cys as to albumin, so it seems likely that this chloride would be short lived inside cells. However, the fluorescence observed inside tumors in vivo persists for days.[10,15,49]

Conclusions from Reactions of 1-Cl with Albumin

The observations outlined above explains why heptamethine cyanine dyes tend to be much longer lived in tumors than Cy-7 derivatives without a meso-chloride, eg ICG.[47] Thus, the weight of the evidence points to short term accumulation of 1-Cl in cancer tissue in vivo, then relatively rapid transformation of this fluor into covalent adducts with biomolecules possessing free thiols. Albumin adducts would be particularly favored, because of the abundance of this protein in the blood. This would then account for persistent fluorescence from cancer tissue in vivo after injection of 1-Cl.

Increased uptake of 1-HSA by the pan-OATP inhibitor BSP (FIG. 44) was surprising, but, in retrospect, perhaps it should not have been. BSP is a venerable old small molecule that rose to fame as a probe for testing liver function; it binds albumin[48] as well as inhibiting OATP receptors.[49] In fact, molecules like this tend to bind lots of proteins non-selectively, so much that they are described by some as a PAIN (Pan Assay INterference compound).[50]

BSP is an inexpensive and convenient probe for testing inhibition of OATP receptors, and in many cases it may be the only logistically feasible option to do so. However, BSP has limitations associated with its interactions with other receptors on cells, and proteins in tissue culture media, and data from cell uptake experiments using this probe should not be over interpreted.

Small molecules attached to albumin in covalent adducts can be fluorescein derivatives as in the conjugate manufactured by Orpegen Pharma (Heidelberg, Germany) for intraoperative fluorescence staining of brain tumors during surgery.[51,52] Related to this, the prospect of conjugating near-IR dyes to albumin for optical imaging has been described in a patent application,[53] but without the realization that 1-Cl could be so combined simply via direct displacement of the meso-Cl via Cys34 in that protein. Moreover, there is growing interest in drugs conjugated to 1-Cl[46,54,55] (like D).[56,57] It is reasonable to assume that these too would combine with albumin in situ when injected into the blood; this might be advantageous insofar as it would generate theranostics for optical imaging and therapy with largely predictable, and extended, blood plasma life-times in vivo.

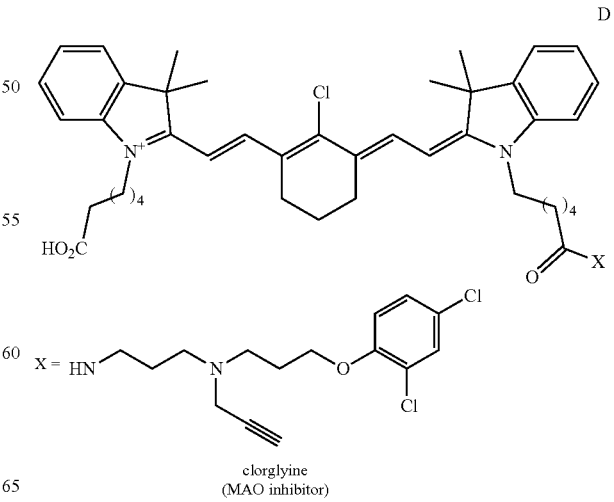

Data presented here also explains some observations in the literature, and some misconceptions to be avoided. For instance, a recent paper noted exceptionally different photophysical properties of a dye related to 1-Cl in the presence and absence of albumin;[58] it may be that a covalent adduct is implicated. With regards to pitfalls, there are two quite different ways to go about making drug-adducts with the core of cyanine 1. When peripheral carboxylic acids are used to make amides or esters, eg D, then these will accumulate in tumors and persist there for a long time as albumin and similar adducts. However, conjugation of drugs to 1-Cl via displacement of the meso-chloride[59] is likely to give products that persist for much shorter times in tumor tissue.

REFERENCES (1) Gibbs, S. L. Quant *Imaging Med Surg* 2012, 2, 177-187.
(2) Nagaya, T.; Nakamura Yu, A.; Choyke Peter, L.; Kobayashi, H. *Front Oncol* 2017, 7, 314.
(3) Frangioni, J. V. *Curr. Opin. Chem. Biol.* 2003, 7, 626-634.
(4) Gioux, S.; Choi, H. S.; Frangioni, J. V. *Mol. Imaging* 2010, 9, 237-255.
(5) Vahrmeijer, A. L.; Hutteman, M.; van der Vorst, J. R.; van de Velde, C. J. H.; Frangioni, J. V. *Nat. Rev. Clin. Oncol.* 2013, 10, 507-518.
(6) Ethirajan, M.; Chen, Y.; Joshi, P.; Pandey, R. K. *Chem. Soc. Rev.* 2011, 40, 340-362.
(7) Choi, H.-S.; Nasr, K.; Alyabyev, S.; Feith, D.; Lee, J.-H.; Kim, S.-H.; Ashitate, Y.; Hyun, H.; Patonay, G.; Strekowski, L.; Henary, M.; Frangioni, J. V. *Angew. Chem., Int. Ed.* 2011, 50, 6258-6263.
(8) Yuan, J.; Yi, X.; Yan, F.; Wang, F.; Qin, W.; Wu, G.; Yang, X.; Shao, C.; Chung, L. W. K. *Mol. Med. Rep.* 2015, 11, 821-828.
(9) Zhao, N.; Zhang, C.; Zhao, Y.; Bai, B.; An, J.; Zhang, H.; Shi, C.; Wu Jason, B. *Oncotarget* 2016, 7, 57277-57289.
(10) Yang, X.; Shao, C.; Wang, R.; Chu, C.-Y.; Hu, P.; Master, V.; Osunkoya, A. O.; Kim, H. L.; Zhau, H. E.; Chung, L. W. K. *J. Urol.* 2013, 189, 702-710.
(11) An, J.; Zhao, N.; Zhang, C.; Zhao, Y.; Tan, D.; Zhao, Y.; Bai, B.; Zhang, H.; Shi, C.; An, J.; Wu Boyang, J. *Oncotarget* 2017, 8, 56880-56892.
(12) Zhang, C.; Zhao, Y.; Zhang, H.; Chen, X.; Zhao, N.; Tan, D.; Zhang, H.; Shi, C. *Int. J. Mol. Sci.* 2017, 18.
(13) Luo, S.; Tan, X.; Qi, Q.; Guo, Q.; Ran, X.; Zhang, L.; Zhang, E.; Liang, Y.; Weng, L.; Zheng, H.; Cheng, T.; Su, Y.; Shi, C. *Biomaterials* 2013, 34, 2244-2251.
(14) Wu, J. B.; Shi, C.; Chu, G. C.-Y.; Xu, Q.; Zhang, Y.; Li, Q.; Yu, J. S.; Zhau, H. E.; Chung, L. W. K. *Biomaterials* 2015, 67, 1-10.
(15) Yang, X.; Shi, C.; Tong, R.; Qian, W.; Zhau, H. E.; Wang, R.; Zhu, G.; Cheng, J.; Yang, V. W.; Cheng, T.; Henary, M.; Strekowski, L.; Chung, L. W. K. *Clin. Cancer Res.* 2010, 16, 2833-2844.
(16) Zhang, C.; Liu, T.; Su, Y.; Luo, S.; Zhu, Y.; Tan, X.; Fan, S.; Zhang, L.; Zhou, Y.; Cheng, T.; Shi, C. *Biomaterials* 2010, 31, 6612-6617.
(17) Luo, S.; Yang, X.; Shi, C. *Curr. Med. Chem.* 2016, 23, 483-497.
(18) Gao, M.; Yu, F.; Lv, C.; Choo, J.; Chen, L. *Chem. Soc. Rev.* 2017, 46, 2237-2271.
(19) Tan, X.; Luo, S.; Wang, D.; Su, Y.; Cheng, T.; Shi, C. *Biomaterials* 2012, 33, 2230-2239.
(20) Wu, J. B.; Shao, C.; Li, X.; Shi, C.; Li, Q.; Hu, P.; Chen, Y.-T.; Dou, X.; Sahu, D.; Li, W.; Harada, H.; Zhang, Y.; Wang, R.; Zhau, H. E.; Chung, L. W. K. *Biomaterials* 2014, 35, 8175-8185.
(21) Thakkar, N.; Lockhart, A. C.; Lee, W. *AAPS Journal* 2015, 17, 535-545.
(22) Kotsampasakou, E.; Ecker, G. F. In Transporters as Drug Targets; Sitte, H. H., Ecker, G. F., Mannhold, R., Buschmann, H., Clausen, R. P., Eds.; Wiley-VCH Verlag GmbH & Co. KGaA: 2017, p 271-324.
(23) Okamura, K.; Dummer, P.; Kopp, J.; Qiu, L.; Levi, M.; Faubel, S.; Blaine, *J. PLoS One* 2013, 8, e54817.
(24) Peters, J. T. All About Albumin: Biochemistry, Genetics, and Medical Applications, 1995.
(25) Gonyar, L. A.; Gray, M. C.; Christianson, G. J.; Mehrad, B.; Hewlett, E. L. *Infect. Immun.* 2017, 85, e00198/00191-e00198/00119.
(26) Spicer, C. D.; Davis, B. G. *Nat. Commun.* 2014, 5, 4740.
(27) Kim, Y.; Ho, S. O.; Gassman, N. R.; Korlann, Y.; Landorf, E. V.; Collart, F. R.; Weiss, S. *Bioconjugate Chem.* 2008, 19, 786-791.
(28) Kullak-Ublick, G.-A.; Hagenbuch, B.; Stieger, B.; Wolkoff, A. W.; Meier, P. *J. Hepatology* (St. Louis) 1994, 20, 411-416.
(29) Milkiewicz, M.; Pugh, C. W.; Egginton, S. *J. Physiol.* (Oxford, U. K.) 2004, 560, 21-26.
(30) Jaakkola, P.; Mole, D. R.; Tian, Y.-M.; Wilson, M. I.; Gielbert, J.; Gaskell, S. J.; von Kriegsheim, A.; Hebestreit, H. F.; Mukherji, M.; Schofield, C. J.; Maxwell, P. H.; Pugh, C. W.; Ratcliffe, P. J. *Science* (Washington, D.C., U. S.) 2001, 292, 468-472.
(31) Liu, Z.; Chen, X. *Chem. Soc. Rev.* 2016, 45, 1432-1456.
(32) Frei, E. Diabetol. *Metab. Syndr.* 2011, 3, 11.
(33) Stehle, G.; Sinn, H.; Wunder, A.; Schrenk, H. H.; Schutt, S.; Maier-Borst, W.; Heene, D. L. *Anti-Cancer Drugs* 1997, 8, 677-685.
(34) Elsadek, B.; Kratz, F. *J. Controlled Release* 2012, 157, 4-28.
(35) Larsen Maja, T.; Kuhlmann, M.; Hvam Michael, L.; Howard Kenneth, A. *Mol Cell Ther* 2016, 4, 3.
(36) Yang, F.; Zhang, Y.; Liang, H. *Int. J. Mol. Sci.* 2014, 15, 3580-3595.
(37) Stoddart, C. A.; Bales, C. A.; Bare, J. C.; Chkhenkeli, G.; Galkina, S. A.; Kinkade, A. N.; Moreno, M. E.; Rivera, J. M.; Ronquillo, R. E.; Sloan, B.; Black, P. L. *PLoS One* 2007, 2, e655.
(38) Stoddart, C. A.; Nault, G.; Galkina, S. A.; Thibaudeau, K.; Bakis, P.; Bousquet-Gagnon, N.; Robitaille, M.; Bellomo, M.; Paradis, V.; Liscourt, P.; Lobach, A.; Rivard, M.-E.; Ptak, R. G.; Mankowski, M. K.; Bridon, D.; Quraishi, O. *J. Biol. Chem.* 2008, 283, 34045-34052.
(39) Kratz, F.; Mueller-Driver, R.; Hofmann, I.; Drevs, J.; Unger, C. *J. Med. Chem.* 2000, 43, 1253-1256.
(40) Graeser, R.; Esser, N.; Unger, H.; Fichtner, I.; Zhu, A.; Unger, C.; Kratz, F. *Invest. New Drugs* 2010, 28, 14-19.
(41) Kratz, F.; Warnecke, A.; Scheuermann, K.; Stockmar, C.; Schwab, J.; Lazar, P.; Drueckes, P.; Esser, N.; Drevs, J.; Rognan, D.; Bissantz, C.; Hinderling, C.; Folkers, G.; Fichtner, I.; Unger, C. *J. Med. Chem.* 2002, 45, 5523-5533.
(42) Baggio, L. L.; Huang, Q.; Cao, X.; Drucker, D. J. *Gastroenterology* 2008, 134, 1137-1147.
(43) Kim, J.-G.; Baggio, L. L.; Bridon, D. P.; Castaigne, J.-P.; Robitaille, M. F.; Jette, L.; Benquet, C.; Drucker, D. J. *Diabetes* 2003, 52, 751-759.

(44) Levitt, D. G.; Levitt, M. D. *Int. J. Gen. Med.* 2016, 9, 229-255.
(45) Kratz, F.; Beyer, U. *Drug Delivery* 1998, 5, 281-299.
(46) Guan, Y.; Zhang, Y.; Xiao, L.; Li, J.; Wang, J.-p.; Chordia, M. D.; Liu, Z.-Q.; Chung, L. W. K.; Yue, W.; Pan, D. *Mol. Pharmaceutics* 2017, 14, 1-13.
(47) Shi, C.; Wu Jason, B.; Pan, D. *J Biomed Opt* 2016, 21, 50901.
(48) Rosenthal, S. M.; White, E. C. *JAMA, J. Am. Med. Assoc.* 1925, 84, 1112-1114.
(49) Jacquemin, E.; Hagenbuch, B.; Stieger, B.; Wolkoff, A. W.; Meier, P. *J. Proc. Natl. Acad. Sci. U.S.A* 1994, 91, 133-137.
(50) Baell, J. B.; Holloway, G. A. *J. Med. Chem.* 2010, 53, 2719-2740.
(51) Ding, R.; Frei, E.; Fardanesh, M.; Schrenk, H.-H.; Kremer, P.; Haefeli, W. E. *J. Clin. Pharmacol.* 2011, 51, 672-678.
(52) Kremer, P.; Fardanesh, M.; Ding, R.; Pritsch, M.; Zoubaa, S.; Frei, E. *Neurosurgery* 2009, 64, 53-61.
(53) Frangioni, J. V.; Onishi, S. 20041117, 2005.
(54) Lv, Q.; Yang, X.; Wang, M.; Yang, J.; Qin, Z.; Kan, Q.; Zhang, H.; Wang, Y.; Wang, D.; He, Z. *J. Controlled Release* 2018, 279, 234-242.
(55) Zhang, E.; Luo, S.; Tan, X.; Shi, C. *Biomaterials* 2014, 35, 771-778.
(56) Wu, J. B.; Lin, T.-P.; Gallagher, J. D.; Kushal, S.; Chung, L. W. K.; Zhau, H. E.; Olenyuk, B. Z.; Shih, J. C. *J. Am. Chem. Soc.* 2015, 137, 2366-2374.
(57) Kushal, S.; Wang, W.; Vaikari, V. P.; Kota, R.; Chen, K.; Yeh, T.-S.; Jhaveri, N.; Groshen, S. L.; Olenyuk, B. Z.; Chen, T. C.; M., H. F.; Shih, J. C. *Oncotarget* 2016, 7, 13842-13853.
(58) Li, B.; Lu, L.; Zhao, M.; Lei, Z.; Zhang, F. *Angew. Chem., Int. Ed.* 2018, 57, 7483-7487.
(59) De los Reyes-Berbel, E.; Salto-Gonzalez, R.; Ortega-Munoz, M.; Reche-Perez, F. J.; Jodar-Reyes, A. B.; Hernandez-Mateo, F.; Giron-Gonzalez, M. D.; Santoyo-Gonzalez, F. *Bioconjugate Chem.* 2018, 29, 2561-2575.

Biomolecule Conjugates

In one aspect, provided herein is a conjugate of Formula (IV):

A-Cy-L-K  (IV)

or a pharmaceutically acceptable salt thereof, wherein:
A is a biomolecule;
Cy is a cyanine dye;
L is a linker selected from optionally substituted aliphatic, optionally substituted heteroaliphatic, optionally substituted aryl, optionally substituted heteroaryl, or a combination thereof;
K is moiety comprising a kinase inhibitor; and
each — is a covalent bond.

In certain embodiments, Formula (IV) is selected from:

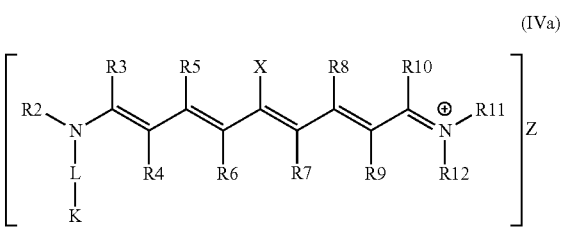
(IVa)

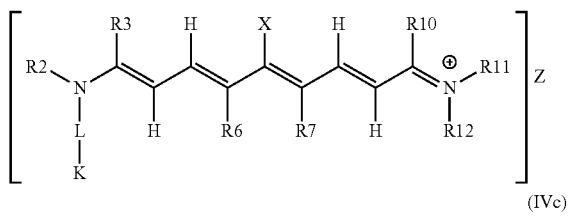
(IVb)

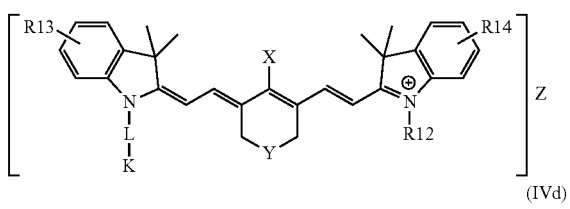
(IVc)

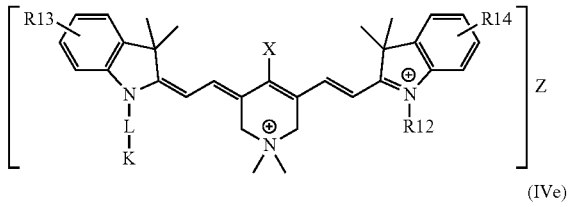
(IVd)

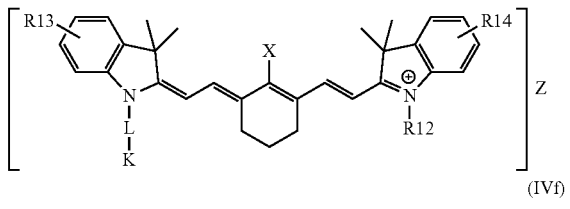
(IVe)

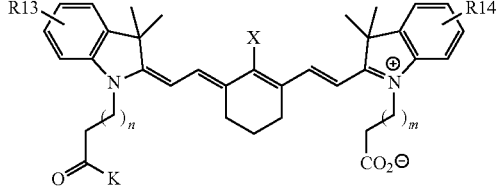
(IVf)

or a pharmaceutically acceptable salt thereof, wherein X is albumin, and wherein R2-R14, L, K, and Z are as defined herein.

In another aspect, provided herein is a conjugate of Formula (V):

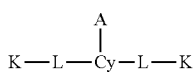
(V)

or a pharmaceutically acceptable salt thereof, wherein:
A is albumin (e.g., human albumin, or animal albumin);
Cy is a cyanine dye;
each L independently is a linker selected from optionally substituted aliphatic, optionally substituted heteroaliphatic, optionally substituted aryl, optionally substituted heteroaryl, or a combination thereof;
each K independently is moiety comprising a kinase inhibitor; and
each — is a covalent bond.

In certain embodiments, Formula (V) is selected from:

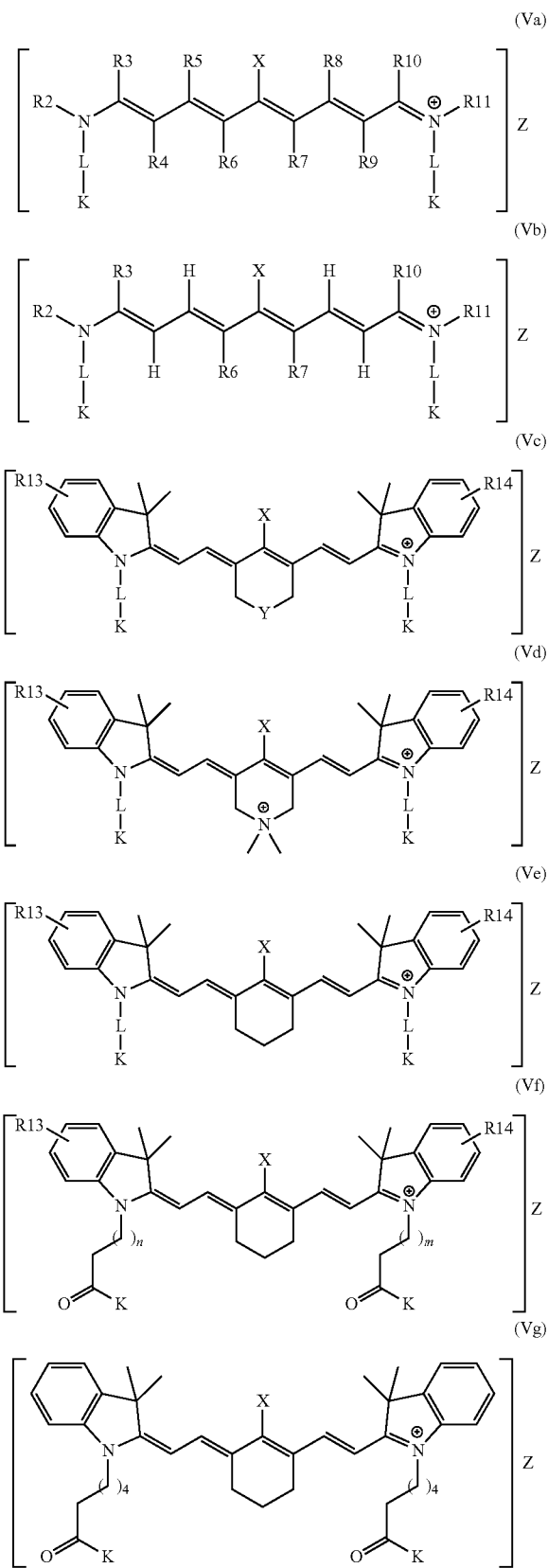

or a pharmaceutically acceptable salt thereof, wherein X is albumin, and wherein R2-R12, L, K, and Z are as defined herein.

In another aspect, provided herein is a compound of Formula (VI):

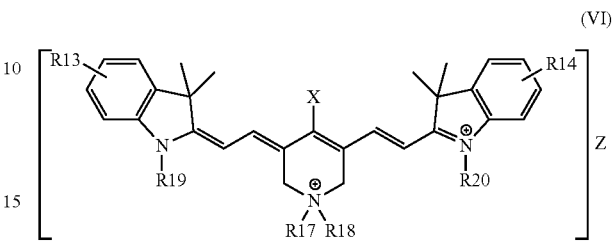

or a pharmaceutically acceptable salt thereof, wherein:
X is albumin (e.g., human albumin, or animal albumin);
Z is one or more anions to achieve electrical neutrality;
R13 and R14 independently are hydrogen or halogen;
R17 and R18 independently are alkyl, heteroalkyl, aryl or heteroaryl; and
R19 and R20 independently are hydrogen, optionally substituted aliphatic, optionally substituted heteroaliphatic, or a nitrogen protecting group.

In certain embodiments of Formulae (V) and (VI), the biomolecule is a protein, e.g., a kinase, or albumin. In a particular embodiment, the protein is a kinase. In a particular embodiment, the protein is albumin (e.g., human albumin or animal albumin).

Conjugates of Formulae (V) and (VI) are useful for applications such as imaging, and the treatment of diseases such as cancer.

EXAMPLES

In order that the invention described herein may be more fully understood, the following examples are set forth. It should be understood that these examples are for illustrative purposes only and are not to be construed as limiting this invention in any manner.

Example 1. Precursor for Synthesis of Compound 1

Synthesis of Vilsmeir Haack Reagent 5.

DMF (65 mL, 0.85 mol) was cooled in a 500 mL round bottom flask by placing it on ice bath. Dropwise, $POCl_3$ (55 mL, 0.6 mol) was added and the mixture was stirred for 30 min. Cyclohexanone (27.5 mL, 0.265 mol) was added and the solution was refluxed at 100° C. for 1 h. Subsequently, the heating was stopped and the reaction was cooled down by placing on ice bath. While the mixture was cooling, aniline/EtOH {1:1(v/v), 90 mL} was added, then the mixture was stirred for 1 h. The product was crystallized from cold $H_2O$:conc. HCl (10:1, 110 mL). The product formed as purple crystals; these were washed with diethyl ether, then isolated by filtration (45.78 g, 86%).

Synthesis of Alkylated Indole 6.

In 500 mL round bottom flask, 2,3,3-trimethylindolenine (20 g, 1.26 mol) and 6-bromohexanoic acid (73 g, 2.5 mol) were added in 200 mL of acetonitrile. The mixture was refluxed for 12 h. Subsequently, the mixture was cooled to room temperature and acetonitrile was removed by rotavap. Subsequently, the flask was placed and in ice bath, the solid residue was dissolved in 100 mL dichloromethane, then 300 mL diethyl ether was added to precipitate the product. That product was collected by filtration and washed with diethyl ether to afford pink crystals (31.10 g, 90%).
Synthesis of 1.

Vilsmeir Haack Reagent 5 (1.27 g, 3.64 mmol), 6 (2.00 g, 7.28 mmol) and NaOAc (597 mg, 7.28 mmol) were dissolved in 100 mL of absolute ethanol in 250 mL round bottom flask. The mixture was heated at reflux for 6 h. The solvent was removed the crude was purified by normal phase flash chromatography with MeOH:DCM (1:25 v/v) to obtain the product 1 as a green solid (0.98 g, 48%). A summary is shown in FIG. 1.

Example 2. Synthesis Scheme for Compound 1a

Figure 2:
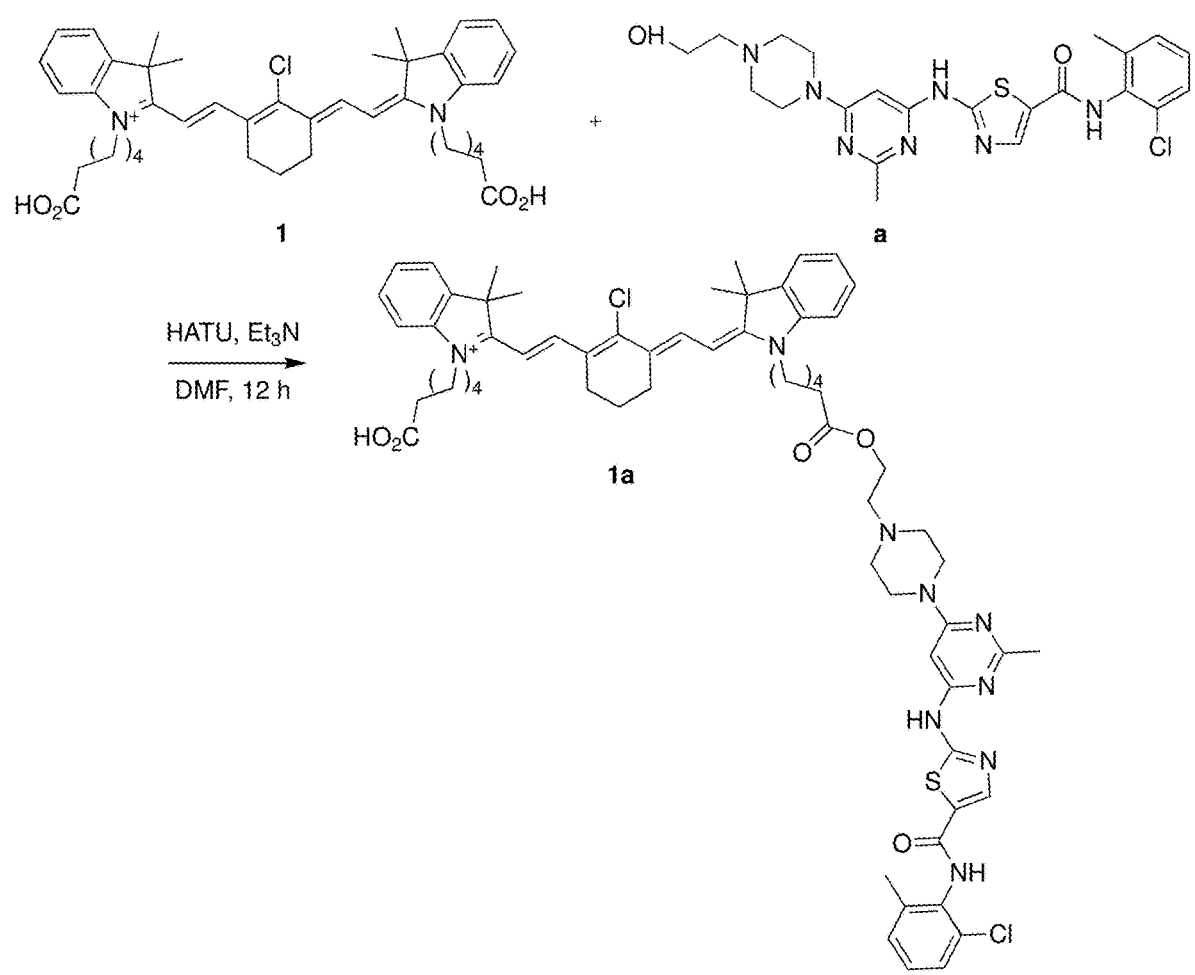

Cyanine dye 1 (200.0 mg, 0.29 mmol), triethylamine (48.50 uL, 0.34 mmol) and HATU (110.2 mg, 0.29 mmol) were added in 2 mL DMF and stirred for 15 mins followed by a (141.52 mg, 0.29 mmol) was added afterwards and stirred for 12 h under argon balloon. Solvent was removed and the crude was purified by reverse phase column on prep-HPLC {50% MeCN/50% $H_2O$-90% MeCN/10% $H_2O$ (containing 0.1% TFA) in 20 mins} to get the desired product as amorphous green solid (32 mg, 9.6%). A summary is shown in FIG. 2.

$^1$H NMR (400 MHz, MeOD) δ 8.46 (dd, J=13.9, 9.9 Hz, 2H), 8.17-8.15 (m, 1H), 7.54 (d, J=7.6 Hz, 2H), 7.45 (dd, J=13.6, 7.5 Hz, 2H), 7.29 (dt, J=14.8, 7.0 Hz, 6H), 6.30 (t, J=13.8 Hz, 2H), 6.16 (s, 1H), 5.50 (s, 3H), 4.51-4.43 (m, 2H), 4.20 (dd, J=12.0, 7.1 Hz, 4H), 3.98 (s, 3H), 3.53-3.40 (m, 5H), 3.37 (s, 1H), 2.74 (d, J=5.9 Hz, 4H), 2.48 (dd, J=16.6, 9.2 Hz, 6H), 2.37-2.28 (m, 6H), 2.01-1.94 (m, 2H), 1.89 (s, 4H), 1.75 (d, J=2.1 Hz, 12H), 1.69 (dd, J=14.3, 6.9 Hz, 5H), 1.53 (q, J=14.7 Hz, 5H).

$^{13}$C NMR (101 MHz, MeOD) δ 175.83, 172.91, 172.56, 162.37, 149.80, 143.83, 142.27, 142.10, 141.30, 141.15, 128.76, 128.56, 126.93, 126.66, 126.46, 125.40, 125.05, 122.15, 111.04, 110.70, 100.53, 83.20, 57.76, 55.32, 53.37, 51.60, 49.39, 49.17, 48.30, 41.02, 33.19, 32.97, 26.96, 26.89, 26.71, 25.99, 25.95, 24.22, 24.04, 20.72, 17.30.

HRMS: calculated 1152.5062; found 1152.5067.

Example 3. Synthesis Scheme for Compound 1b

Compound 1b is made analogously to compound 1a.

$^1$H NMR (400 MHz, MeOD) δ 8.97 (d, J=4.4 Hz, 1H), 8.47 (d, J=14.2 Hz, 1H), 8.37 (s, 1H), 7.94 (d, J=8.2 Hz, 2H), 7.72 (d, J=10.0 Hz, 1H), 7.55 (d, J=7.2 Hz, 1H), 7.50 (d, J=7.5 Hz, 1H), 7.47 (s, 1H), 7.46-7.45 (m, 1H), 7.44 (s, 1H), 7.41 (s, 1H), 7.38 (d, J=7.5 Hz, 2H), 7.34-7.23 (m, 3H), 6.34 (d, J=14.1 Hz, 1H), 6.20 (d, J=14.1 Hz, 1H), 6.03-5.88 (m, 1H), 4.25 (t, J=6.9 Hz, 2H), 4.15 (t, J=7.3 Hz, 2H), 3.80-3.68 (m, 4H), 3.25 (dd, J=8.6, 5.0 Hz, 4H), 2.72 (dt, J=11.8, 6.1 Hz, 4H), 2.54-2.43 (m, 5H), 2.39 (d, J=3.2 Hz, 3H), 2.33 (dd, J=15.8, 8.5 Hz, 4H), 2.08 (s, 2H), 2.01-1.81 (m, 8H), 1.77 (s, 6H), 1.73 (s, 1H), 1.72 (s, 6H), 1.69 (d, J=7.3 Hz, 2H), 1.56-1.45 (m, 4H), 1.31 (s, 1H).

$^{13}$C NMR (101 MHz, MeOD) δ 202.73, 175.82, 173.27, 172.73, 172.47, 161.22, 157.37, 156.11, 155.59, 149.73, 144.19, 144.00, 143.34, 143.19, 142.20, 142.03, 141.79, 141.30, 141.13, 131.92, 128.53, 128.44, 126.48, 126.43, 125.27, 125.14, 122.17, 122.09, 115.85, 111.05, 110.74, 109.31, 101.13, 100.75, 54.07, 49.36, 49.23, 48.31, 48.24, 48.09, 48.02, 44.98, 43.69, 40.97, 33.17, 31.76, 30.07, 27.68, 26.97, 26.93, 26.58, 25.94, 25.32, 24.68, 24.20, 20.71, 12.72.

Example 4. Synthesis Scheme for Compound 1c

Compound 1c is made analogously to compound 1a.

$^1$H NMR (400 MHz, MeOD) δ 8.95 (s, 1H), 8.49 (s, 1H), 8.46 (d, J=4.6 Hz, 1H), 8.43 (s, 1H), 8.40 (d, J=4.8 Hz, 1H), 8.07 (d, J=2.9 Hz, 1H), 8.05 (d, J=2.9 Hz, 1H), 7.87 (d, J=2.8 Hz, 1H), 7.53 (dd, J=13.3, 7.2 Hz, 2H), 7.48-7.42 (m, 2H), 7.42-7.36 (m, 3H), 6.80 (s, 1H), 6.34 (d, J=14.1 Hz, 1H), 6.24 (d, J=14.1 Hz, 1H), 4.24 (t, J=7.0 Hz, 2H), 4.13 (t, J=7.3 Hz, 2H), 3.78-3.70 (m, 3H), 3.26-3.12 (m, 9H), 2.74 (dd, J=12.0, 6.0 Hz, 3H), 2.50 (t, J=7.2 Hz, 4H), 2.34 (t, J=7.2 Hz, 2H), 2.14-2.04 (m, 4H), 2.00 (s, 2H), 1.92 (d, J=7.6 Hz, 2H), 1.85 (s, 2H), 1.77 (s, 5H), 1.75 (s, 2H), 1.73 (s, 6H), 1.69 (dd, J=12.4, 7.8 Hz, 3H), 1.56-1.47 (m, 4H).

$^{13}$C NMR (101 MHz, MeOD) δ 175.74, 173.16, 172.81, 172.41, 163.54, 152.17, 151.74, 149.74, 147.05, 144.29, 144.03, 142.35, 142.24, 142.09, 141.29, 141.16, 136.16, 134.28, 128.52, 126.50, 125.24, 125.17, 122.40, 122.16, 122.09, 115.22, 114.99, 111.01, 110.83, 100.94, 100.74, 58.20, 49.33, 49.24, 44.92, 43.73, 43.64, 40.95, 38.24, 33.97, 33.17, 31.85, 30.08, 26.94, 26.91, 26.60, 26.03, 25.93, 24.64, 24.20, 24.17, 20.72.

HRMS: calculated 1099.6047; found 1099.6035.

Example 5. Synthesis Scheme for Compound 1d

Compound 1d is made analogously to compound 1a.

$^1$H NMR (400 MHz, MeOD) δ 8.46 (dd, J=14.1, 5.0 Hz, 2H), 7.93 (s, 1H), 7.66-7.59 (m, 2H), 7.54 (dd, J=7.6, 2.3 Hz, 2H), 7.52-7.46 (m, 2H), 7.46-7.41 (m, 2H), 7.37 (d, J=7.5 Hz, 1H), 7.35-7.32 (m, 1H), 7.32-7.26 (m, 2H), 7.16 (d, J=1.2 Hz, 1H), 6.38-6.26 (m, 3H), 4.64 (d, J=14.5 Hz, 1H), 4.51-4.39 (m, 1H), 4.28-4.15 (m, 4H), 4.10 (d, J=13.7 Hz, 1H), 2.79 (dd, J=26.1, 8.7 Hz, 5H), 2.50 (t, J=7.3 Hz, 2H), 2.34 (t, J=7.2 Hz, 2H), 2.13 (d, J=13.9 Hz, 3H), 2.01-1.79 (m, 13H), 1.76 (s, 7H), 1.74 (s, 6H), 1.69 (dd, J=14.1, 6.6 Hz, 2H), 1.55 (dt, J=15.2, 7.6 Hz, 4H).

$^{13}$C NMR (101 MHz, MeOD) δ 175.74, 172.94, 172.27, 146.88, 144.14, 142.26, 142.19, 141.73, 141.22, 135.61, 135.18, 129.02, 128.52, 126.58, 125.20, 125.08, 122.14, 121.52, 121.24, 118.41, 118.29, 117.49, 117.26, 116.78, 110.89, 100.95, 74.34, 58.89, 49.29, 44.22, 43.76, 40.35, 33.17, 32.44, 32.20, 31.69, 26.92, 26.68, 26.16, 25.95, 24.74, 24.23, 20.73, 17.55.

HRMS: calculated 1114.4690; found 1114.4678.

Example 6. Synthesis Scheme for Compound 1e

Compound 1e is made analogously to compound 1a.

$^1$H NMR (400 MHz, MeOD) δ 8.48 (s, 1H), 8.45 (d, J=4.7 Hz, 1H), 8.42 (s, 1H), 8.40 (s, 1H), 8.14 (s, 1H), 7.95 (dd, J=8.0, 1.5 Hz, 1H), 7.70-7.64 (m, 2H), 7.53 (dd, J=10.5, 7.3 Hz, 2H), 7.49-7.41 (m, 2H), 7.41 (s, 1H), 7.38 (s, 1H), 7.36 (s, 1H), 7.35-7.26 (m, 3H), 6.81 (s, 1H), 6.33-6.22 (m, 2H), 4.70 (s, 1H), 4.57 (dt, J=12.3, 6.1 Hz, 1H), 4.23 (t, J=7.2 Hz, 2H), 4.17 (t, J=7.4 Hz, 2H), 4.10 (d, J=13.8 Hz, 1H), 3.20 (s, 1H), 3.00 (s, 1H), 2.81-2.64 (m, 5H), 2.49 (td, J=7.2, 3.0 Hz, 2H), 2.32 (t, J=7.3 Hz, 2H), 2.17 (d, J=10.0 Hz, 3H), 1.94 (td, J=13.3, 5.9 Hz, 4H), 1.90-1.78 (m, 5H), 1.76 (s, 6H), 1.73 (s, 6H), 1.71-1.66 (m, 2H), 1.56 (ddd, J=23.4, 17.2, 10.7 Hz, 6H), 1.28 (dd, J=12.8, 6.5 Hz, 14H).

$^{13}$C NMR (101 MHz, MeOD) δ 175.70, 173.02, 172.18, 156.06, 149.73, 146.41, 144.25, 143.99, 142.27, 142.13, 141.22, 138.85, 134.65, 131.06, 128.52, 127.25, 126.58, 125.24, 125.16, 124.48, 124.11, 123.08, 122.11, 111.65, 110.91, 105.19, 101.00, 100.89, 71.62, 55.48, 49.28, 46.37, 43.72, 42.37, 38.11, 33.16, 32.93, 32.30, 32.16, 29.33, 26.92, 26.81, 26.65, 26.13, 25.95, 24.82, 24.21, 21.03, 20.74, 17.67, 14.08.

Example 7. Synthesis Scheme for Compound 2a

Compound 2a is made analogously to compound 2b (see below).

Example 8. Synthesis Scheme for Compound 2b

Figure 3:
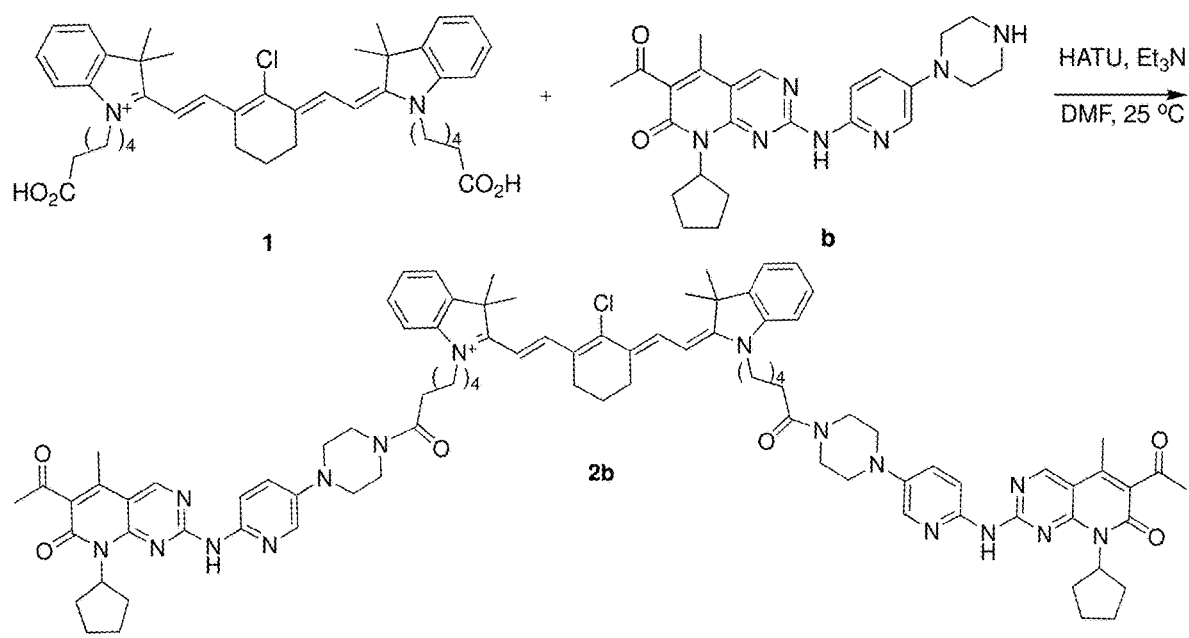
FIG. 3 shows the synthesis scheme for 2b.

Cyanine dye 1 (200.0 mg, 0.29 mmol), triethylamine (48.50 uL, 0.34 mmol) and HATU (110.2 mg, 0.29 mmol) were added in 2 mL DMF and stirred for 15 mins followed by b (130.5 mg, 0.58 mmol) and stirred for 12 h under argon balloon. Solvent was removed and the crude was purified by reverse phase column on prep-HPLC {50% MeCN/50% $H_2O$-90% MeCN/10% $H_2O$ (containing 0.1% TFA) in 20 mins} to get the desired product as amorphous green solid (143.4 mg, 32%). A summary of the scheme is shown in FIG. 3.

$^1$H NMR (400 MHz, MeOD) δ 9.00 (s, 2H), 8.40 (d, J=14.1 Hz, 2H), 8.03 (dd, J=9.5, 2.7 Hz, 2H), 7.92 (d, J=2.8 Hz, 2H), 7.67 (d, J=9.5 Hz, 2H), 7.52 (d, J=7.4 Hz, 2H), 7.40 (t, J=7.6 Hz, 2H), 7.33-7.25 (m, 3H), 6.26 (d, J=14.1 Hz, 2H), 6.04-5.92 (m, 2H), 4.19 (t, J=7.0 Hz, 3H), 3.81-3.68 (m, 7H), 3.30-3.20 (m, 7H), 2.71 (t, J=5.9 Hz, 3H), 2.51 (s, 6H), 2.49 (d, J=7.1 Hz, 2H), 2.40 (s, 5H), 2.32 (dd, J=11.6, 7.9 Hz, 4H), 2.09 (s, 4H), 2.00-1.82 (m, 9H), 1.77 (s, 1H), 1.74 (s, 12H), 1.69 (dd, J=13.3, 6.9 Hz, 5H), 1.53-1.44 (m, 4H).

$^{13}$C NMR (101 MHz, MeOD) δ 202.51, 173.03, 172.40, 161.15, 157.16, 155.82, 155.66, 149.65, 144.03, 143.12, 143.01, 142.08, 141.62, 141.22, 132.27, 128.46, 126.38, 125.22, 122.13, 116.00, 110.92, 109.65, 100.98, 54.11, 49.31, 44.88, 43.71, 40.90, 31.81, 30.03, 27.67, 26.97, 26.86, 25.98, 25.93, 25.31, 24.62, 20.73, 12.73.

HRMS: calculated 1541.8164; found 1541.8180.

Example 9. Synthesis Scheme for Compound 2c

Compound 2c is made analogously to compound 2b.

Example 10. Synthesis Scheme for Compound 2d

Compound 2d is made analogously to compound 2b.

Example 11. Synthesis Scheme for Compound 2e

Compound 2e is made analogously to compound 2b.

Example 12. Illustrative Procedure for Cytotoxicity of 1a on HEPG2 Cells

Approximately 5000 HEPG2 cells/well were seeded on 96 well plate containing 10% fetal bovine serum. Cells were allowed to adhere overnight before test compounds were added. Stock solutions of 1a (0.02 M in DMSO) were diluted with protein-free medium (PFHM-II) to make desired final concentrations varying from 0.01 to 80 μM. The cells were incubated with the desired concentration for 48 h. The cell viabilities were calculated using MTT assay. Briefly, 20 μL of 3-(4,5-dimethylthiazol-2-yl)-2,5-diphenyltetrazolium bromide MTT (5 mg/mL, in Hank's balanced salt solution) were added and the cells were incubated for an additional 3.5 h. The medium was then removed, and 100 mL of DMSO was added to dissolve the formazan crystal formed. The optical density of each well (at 570 nm) was measured with a BioTek Synergy 4 Microplate Reader. The viability of each cell line in response to the treatment with tested compounds was calculated as: % dead cells=100−(OD treated/OD control)×100.

Dasatinib (Kinase Inhibitor "a" and "b") Conjugates

Figure 4A:
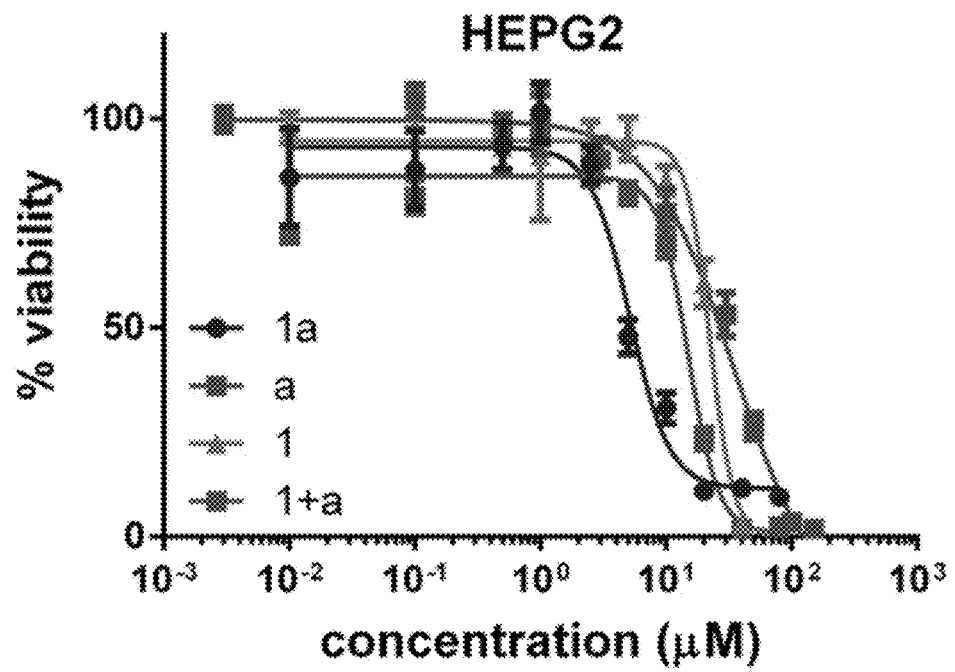
Figure 4B:
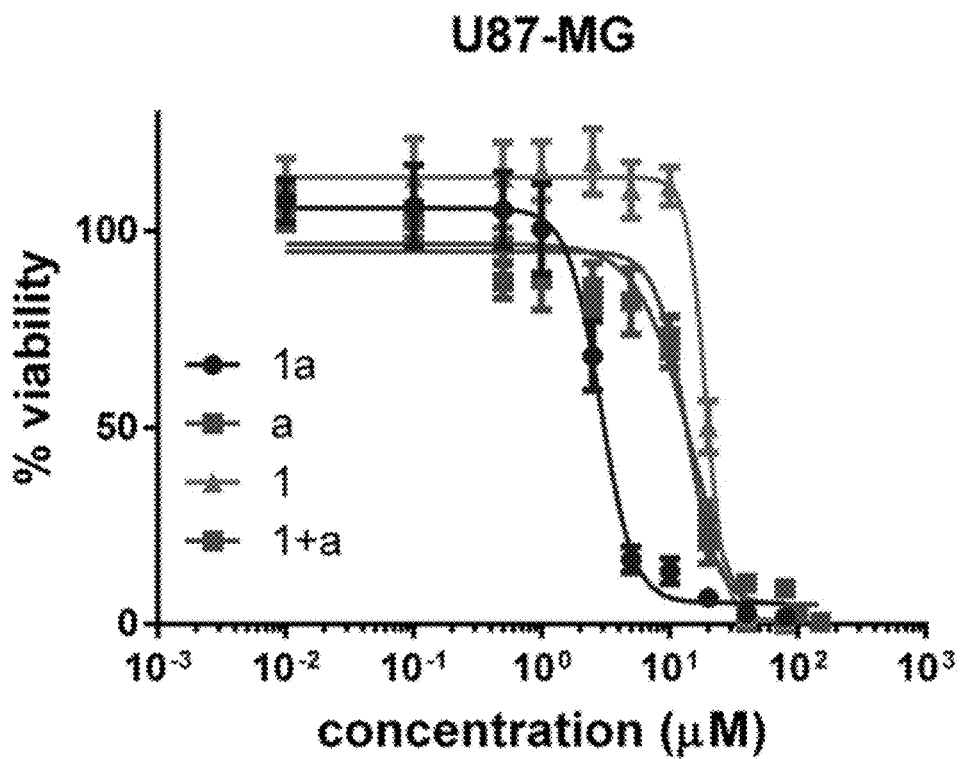

FIGS. 4A and 4B show that the conjugate 1a is significantly more toxic than the parent dye, the parent kinase inhibitor, or a mixture of the dye and kinase inhibitor on HEPG2 liver cancer cells (FIG. 4A) and (FIG. 4B) U87MG glioblastoma cells.

Figure 5A:
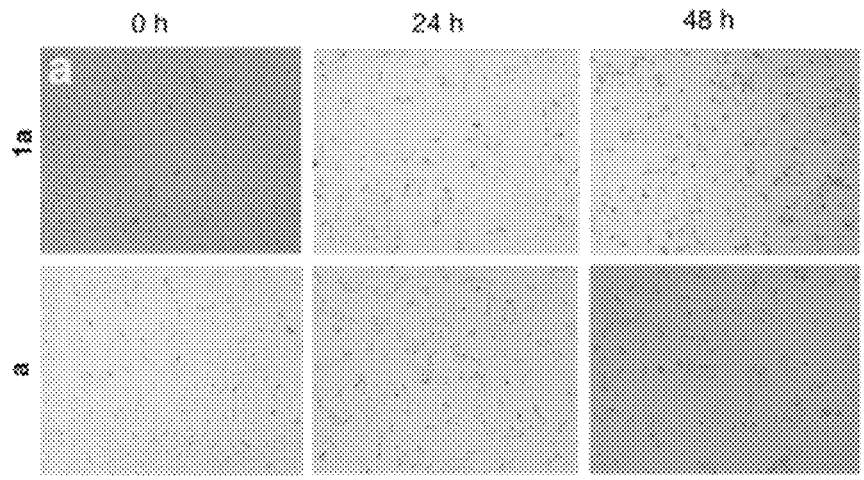
FIGS. 5A and 5B shows 1a in HEPG2 cells.

FIG. 5A visualizes some of the data from FIGS. 4A and 4B (that on HEPG2 cells). Compound 1a has a much stronger influence on the cell morphology after 24 and 48 h when compared the parent kinase inhibitor dasatinib a.

Figure 5B:
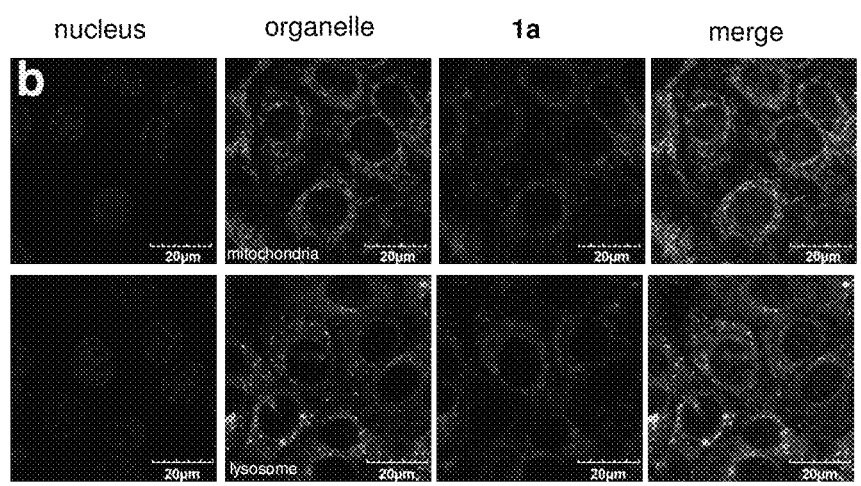

Localization of compounds in mitochondria tends to give more pronounced cytotoxicity effects than accumulation in most organelles. FIG. 5B shows 1a localizes preferentially in mitochondria, though some colocalized with a dye that tracks lysosomes.

Figure 6A:
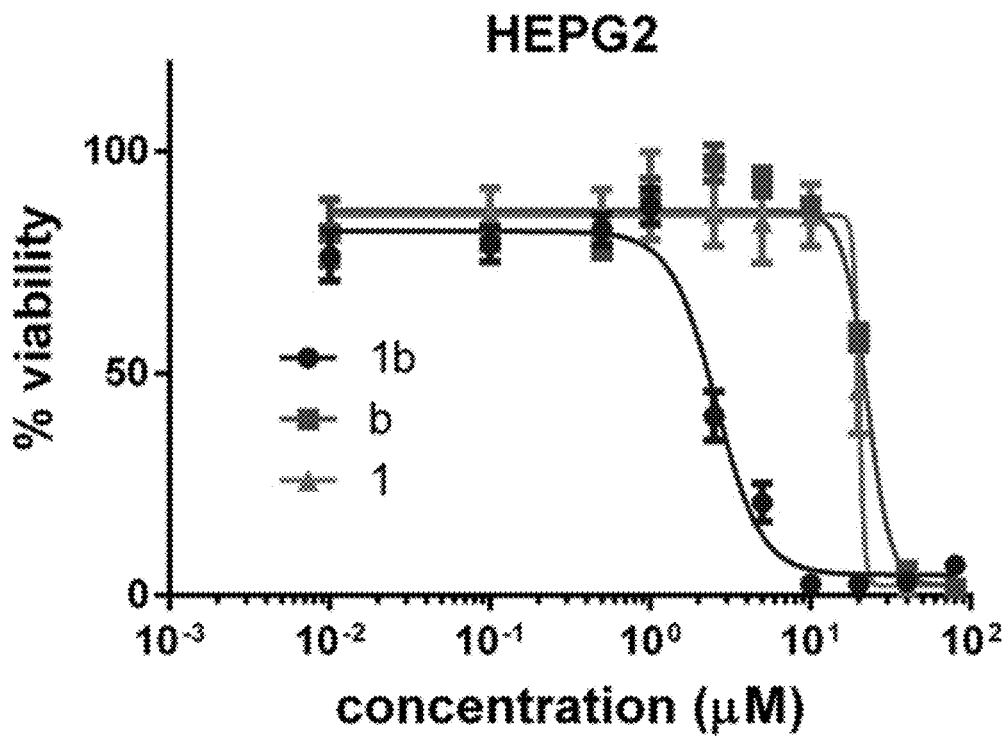
FIGS. 6A to 6C shows cell viability assay of 1b on HEPG2 cells (liver cancer) (FIG. 6A); U87-MG cells (glioblastoma cancer) (FIG. 6B) and K562 (leukemia) (FIG. 6C). 1b was more found to be toxic than individual 1, b or a combination of 1+b.
Figure 6B:
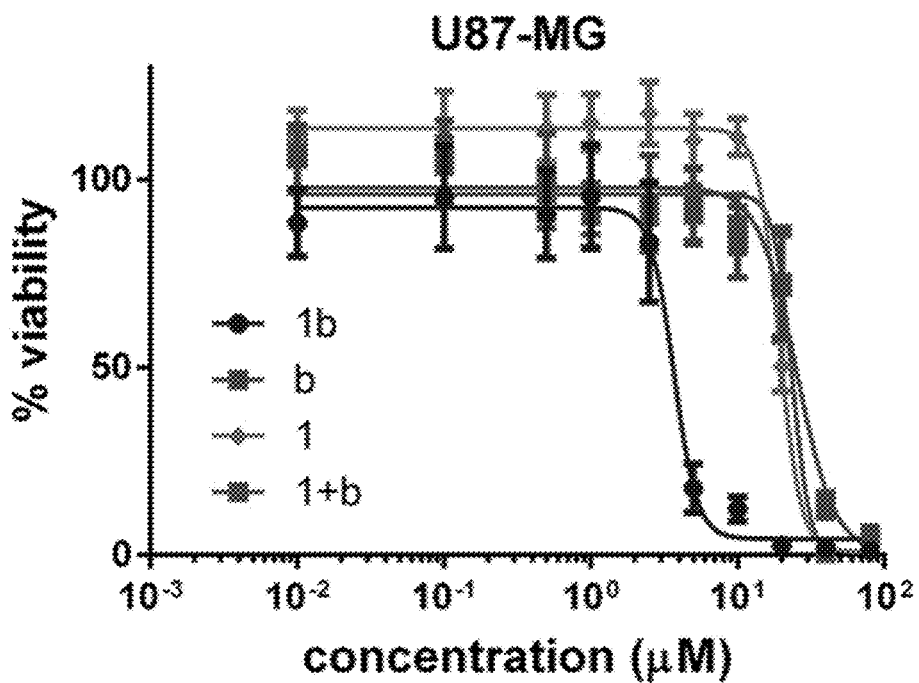
Figure 6C:
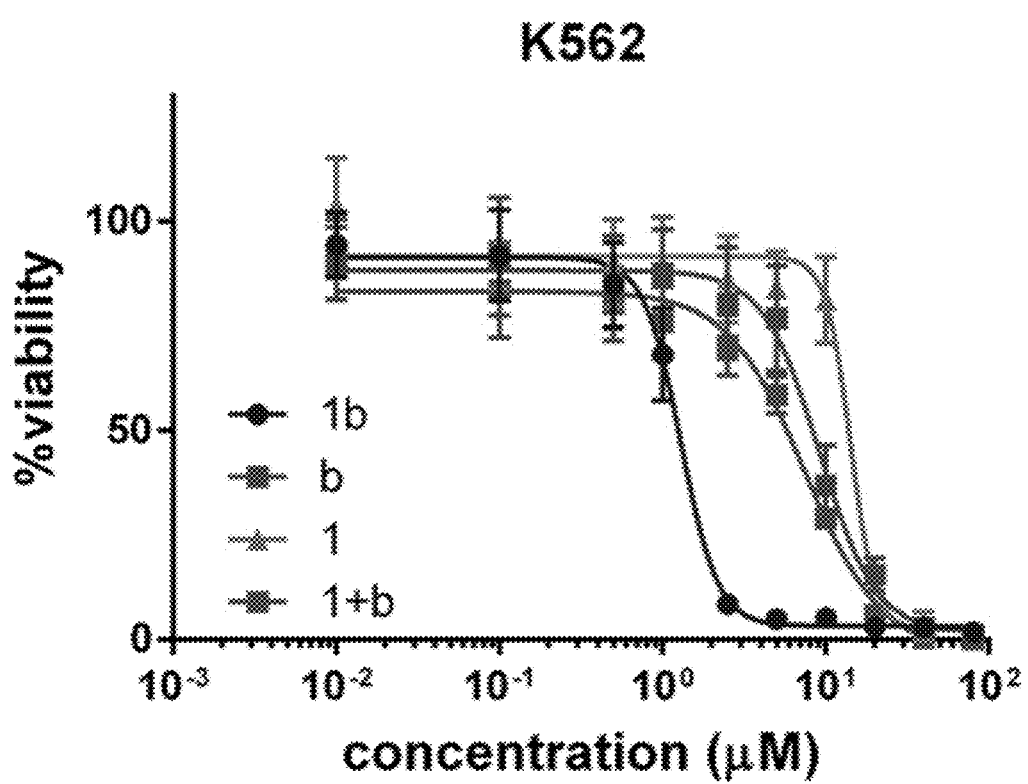

FIGS. 6A to 6C show that the conjugate 1b is significantly more toxic than the parent dye, the parent kinase inhibitor, or a mixture of the dye and kinase inhibitor on HEPG2 liver cancer cells (FIG. 6A), U87MG glioblastoma cells (FIG. 6B) and K562 leukemia cells (FIG. 6C).

Ribociclib (Kinase Inhibitor "c") Conjugates

Figure 7:
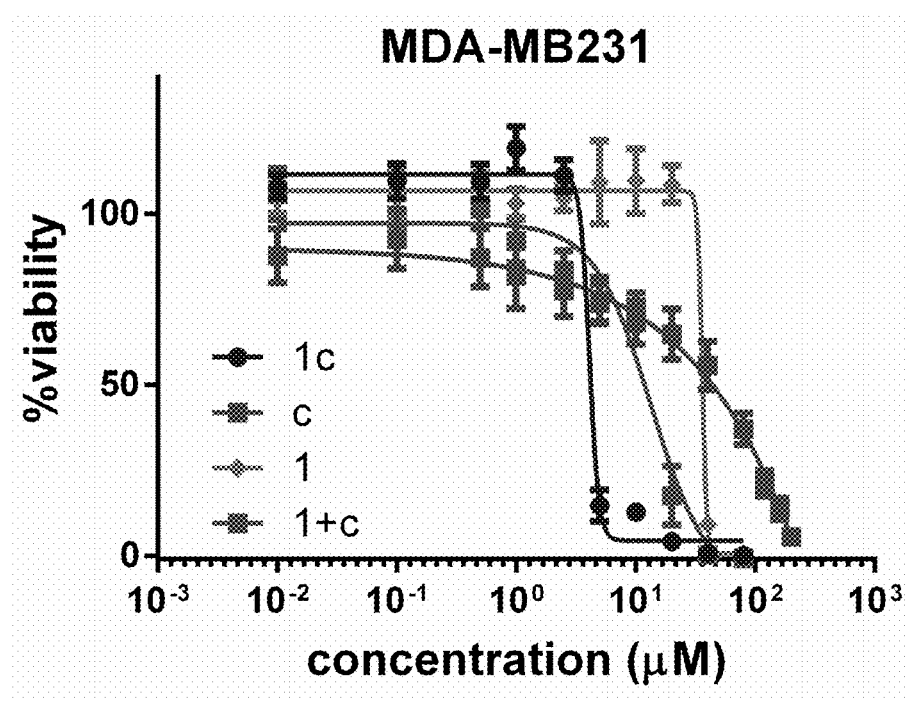
FIG. 7 shows cell viability assay of 1c on MBA-MB-231 (breast cancer cells). 1c was more found to be toxic than individual 1, c or a combination of 1+c.

FIG. 7 shows that the conjugate 1c is significantly more toxic than the parent dye, the parent kinase inhibitor, or a mixture of the dye and kinase inhibitor on MDA-MB-231 "triple negative" breast cancer cells.

Crizotinib (Kinase Inhibitor "d") Conjugates

Figure 8:
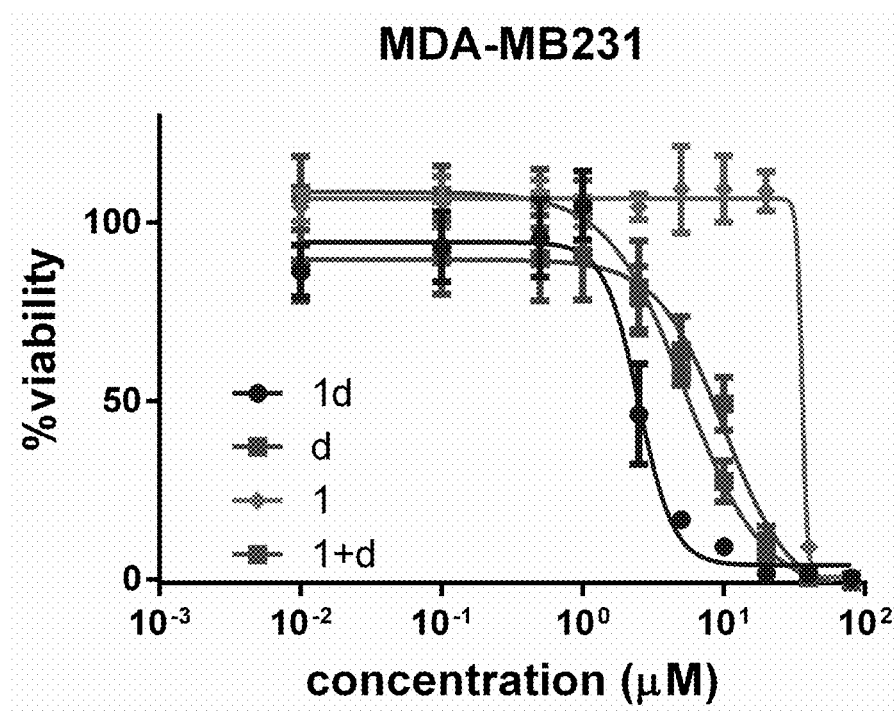
FIG. 8 shows cell viability assay of 1d on MDA-MB-231 (breast cancer cells). 1d was more found to be toxic than individual 1, d or a combination of 1+d.

FIG. 8 shows that the conjugate 1d is significantly more toxic than the parent dye, the parent kinase inhibitor, or a mixture of the dye and kinase inhibitor on MDA-MB-231 "triple negative" breast cancer cells.

Example 13. Novel Dye with Ammonium Functionality

Synthesis of 1,1-dimethyl-4-oxopiperidin-1-ium iodide 8

1-Methyl-4-piperidone (20 g, 0.18 mol) was dissolved in acetone (300 mL) and cooled to 0° C. Methyl iodide (22.0 mL, 0.35 mol) was slowly added into the solution over 10 min. The mixture solution was stirred from 0° C. to 25° C. for 4 h during which time a white precipitate was formed. The product was filtered and washed with cold acetone. The white solid was collected and dried in vacuum (43.0 g, yield: 94%) and used next step without purification.

Synthesis of 4-chloro-3-(hydroxymethylene)-1,1-dimethyl-5-((E)-(phenylimino)methyl)-1,2,3,6-tetrahydropyridin-1-ium chloride 7

A solution of DMF (18.0 mL, 0.23 mol) in dichloromethane (18.0 mL) was cooled to 0° C. A solution of $POCl_3$ (11.5 mL, 0.12 mol) in dichloromethane (12 mL) was added dropwise then the solution was stirred at 0° C. for 30 min. Compound 7 (10 g, 0.04 mol) was added, then the solution and refluxed for 3 h. The dichloromethane was removed. The aniline (5.5 mL, 0.06 mol) in ethanol (5.5 mL) was added dropwise at 0° C. and further stirred for 60 min. The solution was poured into cold conc. $HCl:H_2O$ (15:85 v/v) and allowed to stand overnight. The product was filtered and washed three times with cold methanol. The brown solid was collected and dried in vacuum (2.4 g, yield: 20%) and used next step without purification.

Synthesis of 1-NMe$_2$

Figures 9, 10, 11:
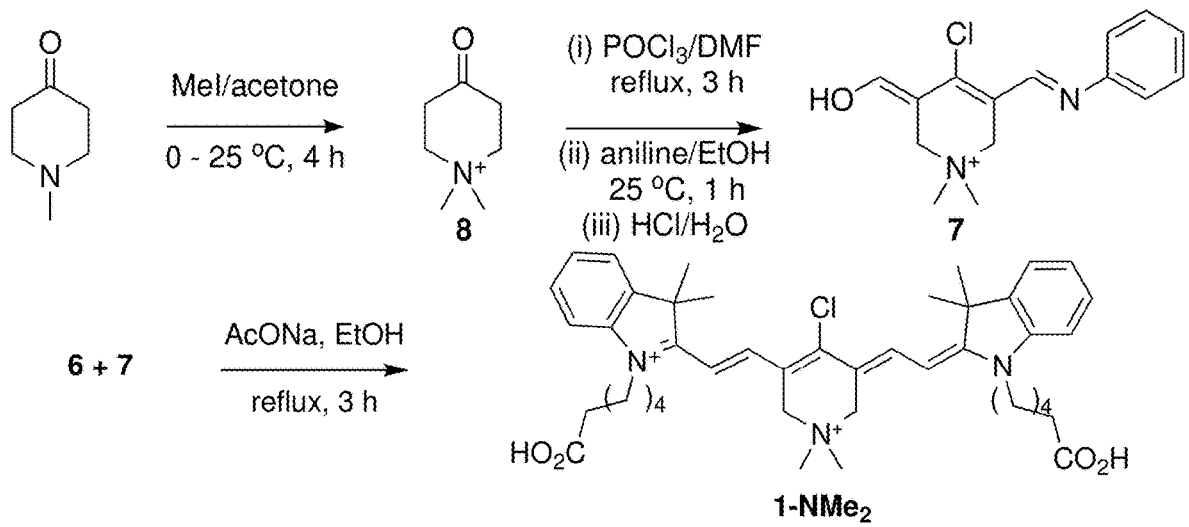
FIG. 9 shows the synthesis scheme of 1-NMe$_2$.
FIG. 10 shows photophysical properties of 1-NMe$_2$ compared to 1-CH$_2$ and ICG. 1-NMe$_2$ has ~3× the extinction coefficient in water than 1-CH$_2$.
FIG. 11 shows photophysical properties of 1-NMe$_2$ compared to 1-CH$_2$. 1-NMe$_2$ has 2× the quantum yield and brightness in phosphate buffer saline (PBS, pH 7.4).

Compound 6 (3.0 g, 8.5 mmol) and sodium acetate (700 mg, 8.5 mmol) were dissolved in ethanol (50 mL) and stirred at 25° C. for 20-30 min. Compound 7 (1.2 g, 3.8 mmol) was added and refluxed for 4-6 h. Solvent was removed. The reverse phrase column was performed followed by purification by reverse phrase prep HPLC with system of acetonitrile and water containing 0.1% TFA to get the pure compound (500 mg, yield: 14%). A summary of the scheme is shown in FIG. 9.

1H of 1-NMe$_2$ $^1$H NMR (400 MHz, MeOD) δ 8.47 (d, J=14.8 Hz, 2H), 7.62 (d, J=7.4 Hz, 2H), 7.47-7.454 (m, 4H), 7.39-7.43 (m, 2H), 6.33 (d, J=14.8 Hz, 2H), 4.72 (s, 4H), 4.31 (t, J=7.5 Hz, 4H), 3.4 (s, 6H), 2.36 (t, J=7.2 Hz, 4H), 1.88-1.99 (m, 4H). 1.79 (s, 12H), 1.66-1.85 (m, 4H), 1.51-1.63 (m, 4H)

13C of 1-NMe$_2$ $^{13}$C NMR (100 MHz, MeOD) δ 175.8, 175.5, 143.9, 143.8, 141.7 (2C), 128.8, 126.4, 122.3, 112.3, 111.9, 100.7, 60.7, 51.6, 50.0, 44.2, 33.2, 26.9, 26.7, 25.8, 24.1

HRMS (ESI positive) calc. for $C_{43}H_{56}ClN_3O_4^{2+}$, [M$^{2+}$] Calculated: 356.6974, found: 356.6965.

Spectroscopic Properties of 1-NMe$_2$

FIG. 10 shows that ICG, compound 1-CH$_2$, and 1-NMe$_2$ have similar extinction coefficients in methanol and Stokes' shifts, but 1-NMe$_2$ absorbs and fluorescence maximally at slightly (~30 nm) shorter wavelengths. However, in PBS buffer and in water 1-NMe$_2$ has a stronger extinction coefficient than 1-CH$_2$.

FIG. 11 shows that 1-NMe$_2$ is a brighter dye than 1-CH$_2$ in PBS buffer.

Figure 12:
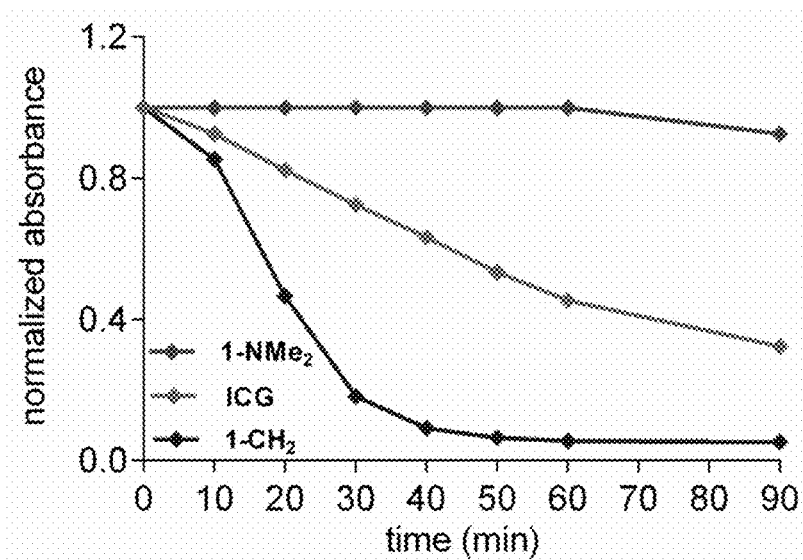
FIG. 12 shows photostablity of 1-NMe$_2$ as compared to 1-CH$_2$ and ICG in PBS (pH 7.4) under LED irradiation at 780 nm. 1-NMe$_2$ is more stable than 1-CH$_2$.

FIG. 12 shows 1-NMe$_2$ is significantly more photostable than 1-CH$_2$ or ICG. Enhanced photostability of this dye may be significant for many applications, particularly including super resolution microscopy via methods like STEM, PALM, and STORM.

Figure 13:
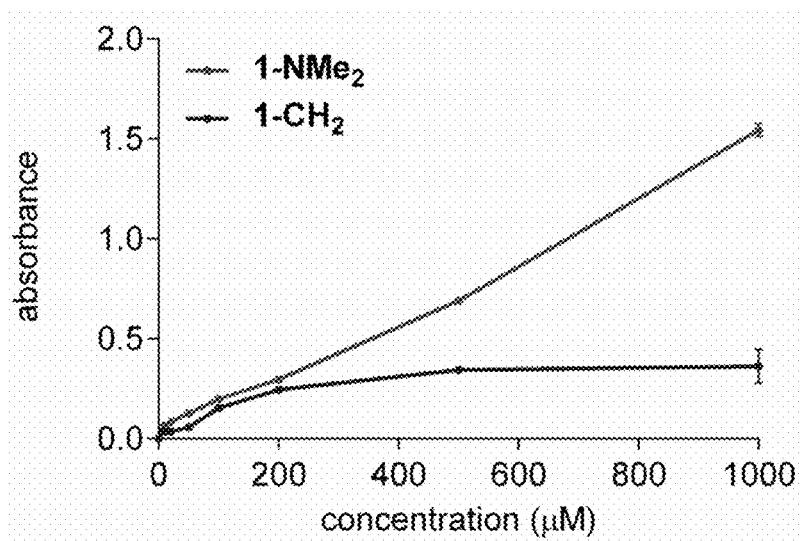
FIG. 13 shows solubility of 1-NMe$_2$ as compared to 1-CH$_2$ in water. 1-NMe$_2$ is water soluble up until 1000 μM whereas 1-CH$_2$ precipitates at 100 μM.

FIG. 13 shows 1-NMe$_2$ is significantly more soluble in water than 1-CH$_2$.

Example 14. Iodinated Analogs Designed to be PDT Active (Photocytotoxic)

Synthesis of I2-1-NMe$_2$

Figure 14:
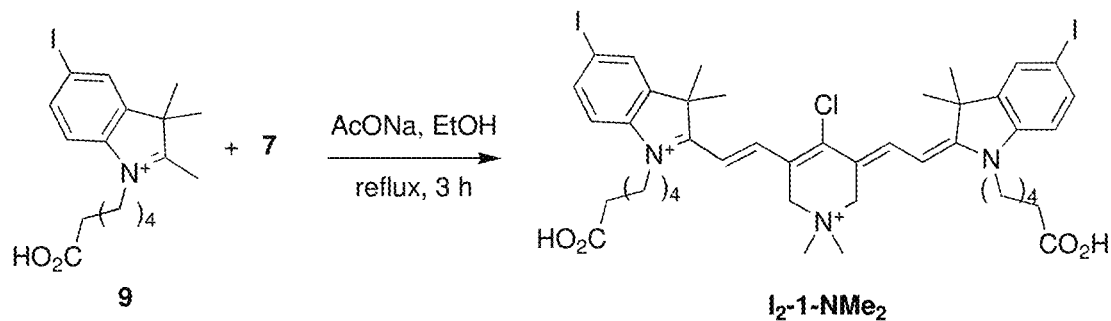
FIG. 14 shows the synthesis of I$_2$-1-NMe$_2$.

Compound 9 (300 mg, 0.78 mmol) and sodium acetate (63 mg, 0.77 mmol) were dissolved in ethanol (10 mL) and stirred at 25° C. for 20-30 min. Compound 7 (100 mg, 0.32 mmol) was added and refluxed for 3 h. Solvent was removed. The crude product was purified by reverse phrase prep HPLC with system of acetonitrile and water containing 0.1% TFA to get the product (50 mg, yield: 14%). The synthesis scheme is shown in FIG. 14.

1H of I2-1-NMe$_2$ $^1$H NMR (400 MHz, MeOD) δ 8.45 (d, J=14.8 Hz, 2H), 7.99 (s, 2H), 7.86 (d, J=8.4 Hz, 2H), 7.29 (d, J=8.4 Hz, 2H), 6.32 (d, J=14.8 Hz, 2H), 4.72 (s, 4H), 4.29 (t, J=7.4 Hz, 4H), 3.42 (s, 6H), 2.36 (t, J=7.2 Hz, 4H), 1.82-1.93 (m, 4H). 1.78 (s, 12H), 1.65-1.75 (m, 4H), 1.51-1.57 (m, 4H).

13C of I2-1-NMe$_2$ $^{13}$C NMR (100 MHz, MeOD) δ 175.9, 174.8, 144.3, 144.0 (2C), 141.6, 137.9, 131.6, 113.8, 113.3, 101.1, 89.9, 60.6, 51.6, 50.0, 44.4, 33.2, 26.8, 26.6, 25.7, 24.1.

New PDT Cyanine Dyes

Figure 15:
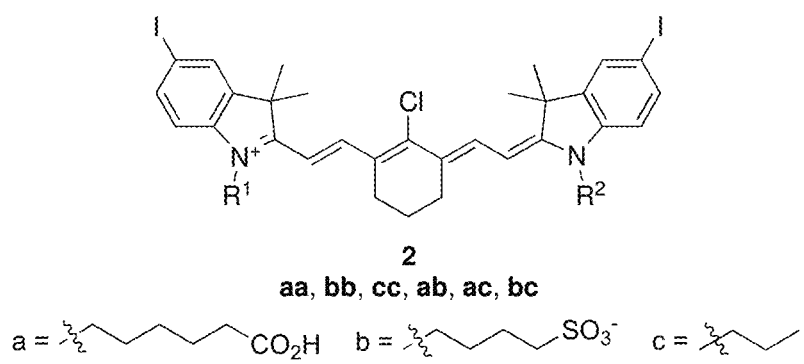
FIG. 15 shows new PDT cyanine dyes.
Figure 16:
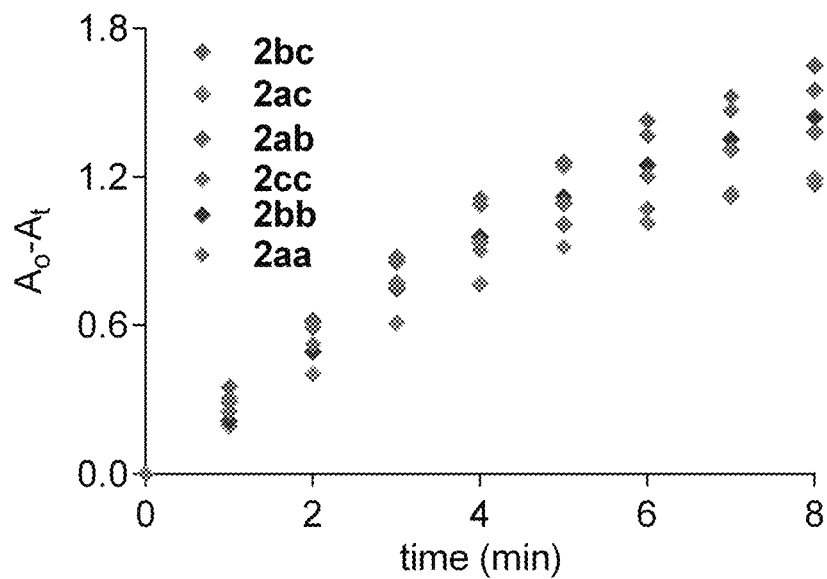
FIG. 16 shows Singlet Oxygen ($^1$O$_2$) generation assay. Plots of change in absorbance of DPBF at 418 nm overtime of compound 2 series was determined.
Figure 17A:
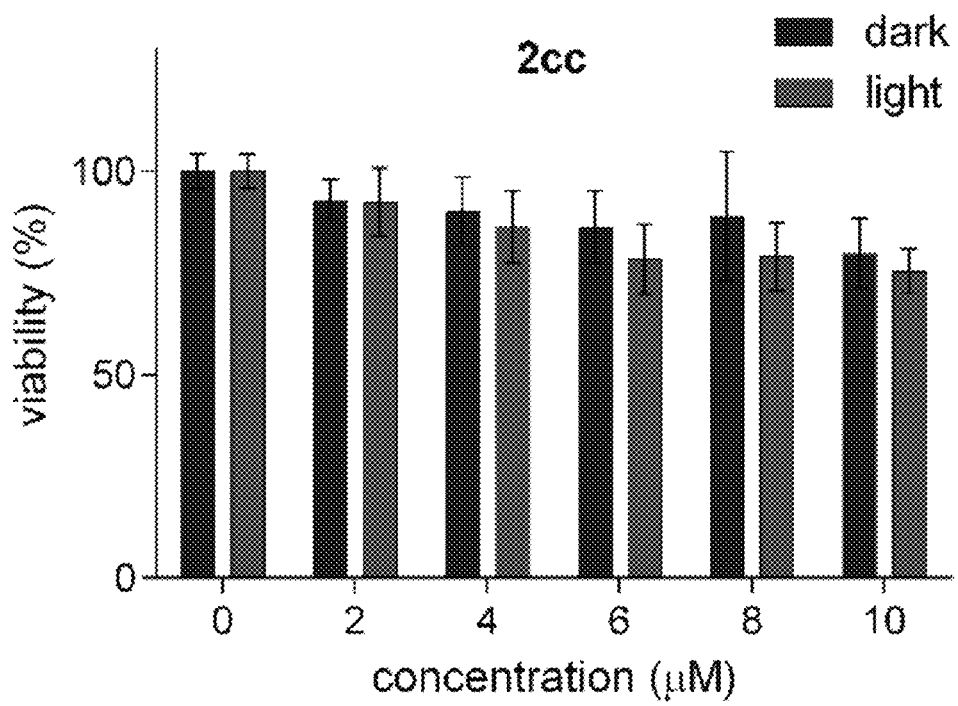
FIGS. 17A to 17F show light and dark cytotoxicity of compound 2aa (FIG. 17A); 2bb (FIG. 17B); 2ab (FIG. 17C); 2cc (FIG. 17D); 2ac (FIG. 17E); and 2bc (FIG. 17F) was determined after irradiation under 780 nm LED or kept in dark as control. 2ac and 2bc are more photocytotoxic than compound 2bb.
Figure 17B:
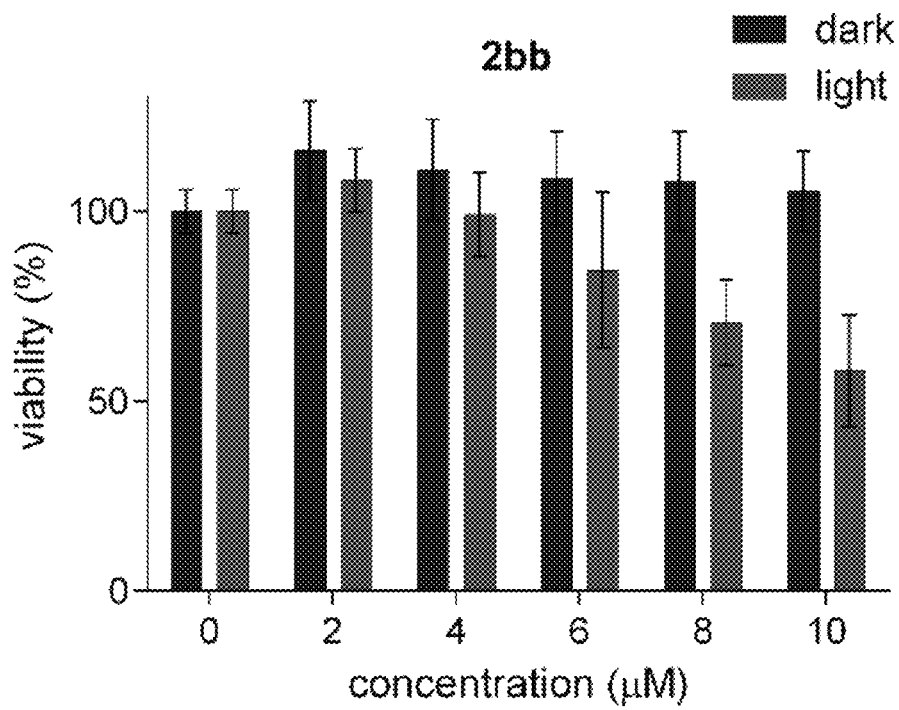
Figure 17C:
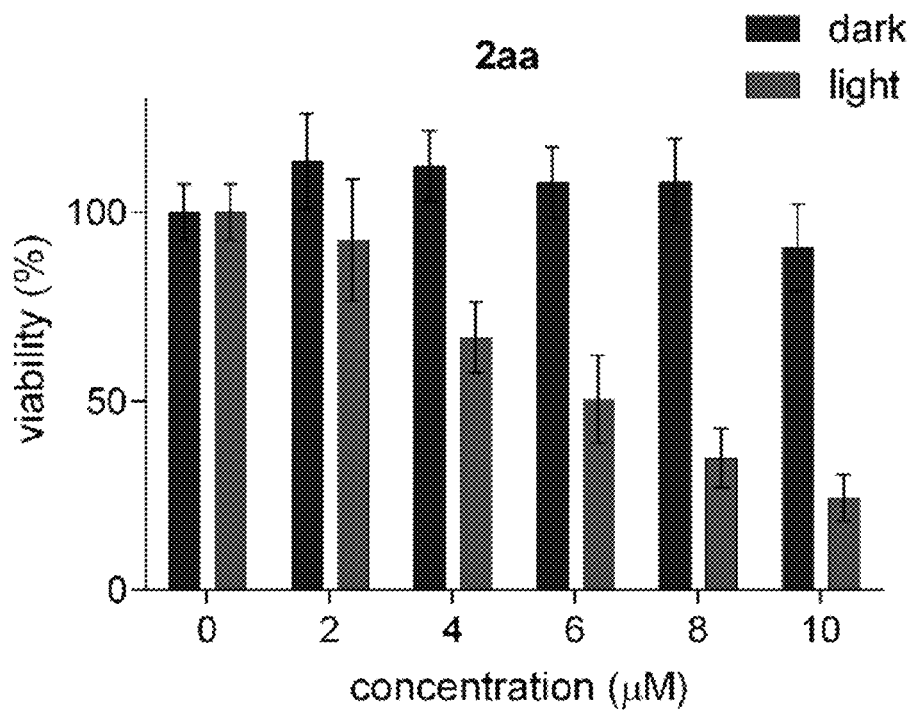
Figure 17D:
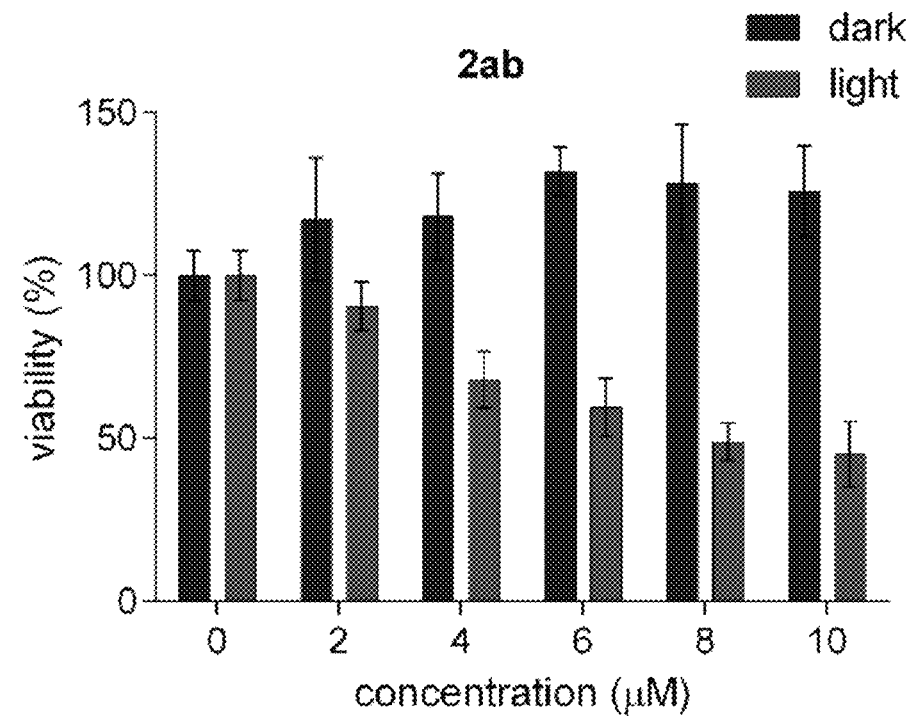
Figure 17E:
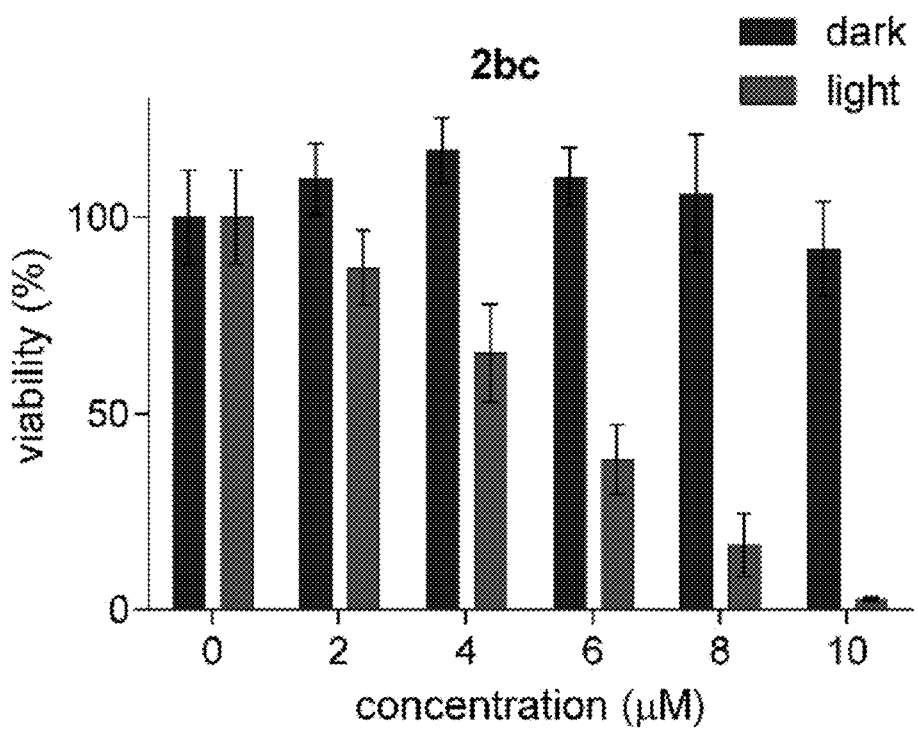
Figure 17F:
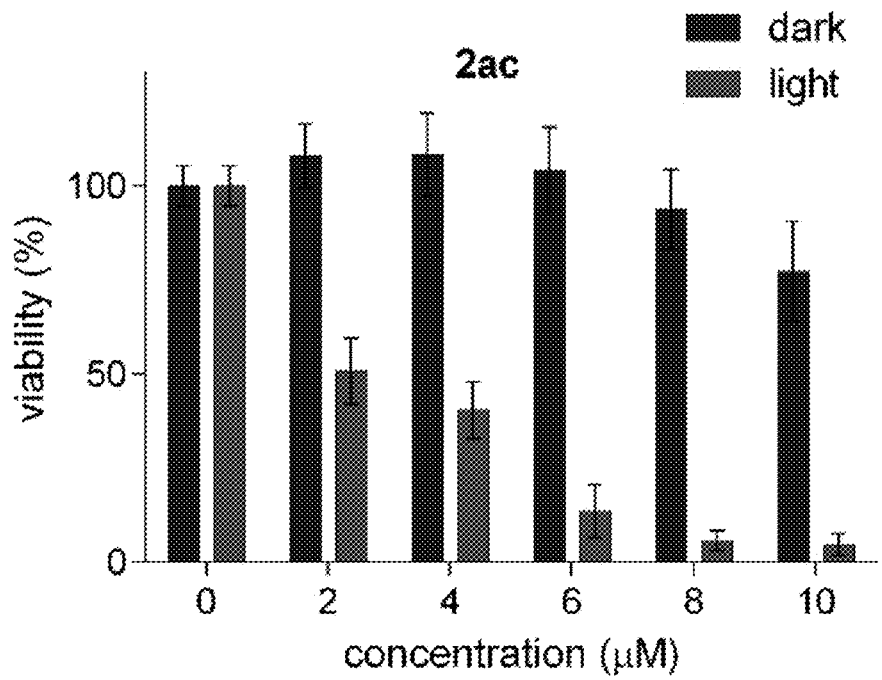
Figure 18:
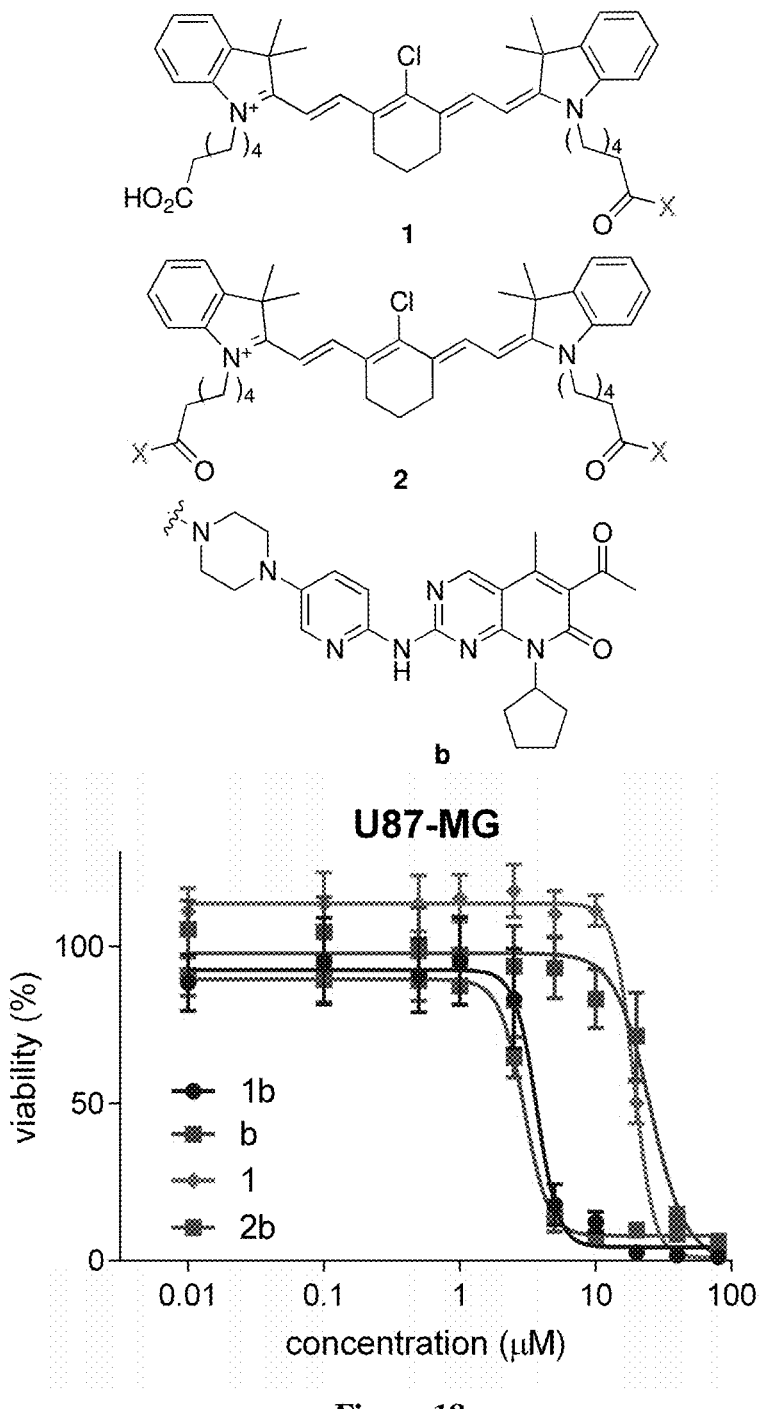
FIG. 18 shows compounds 1a and 1b. Cytotoxicity of 2b as compared to 1b, 1 and b on U87-MG (Glioblastoma cells). It was observed that 1b and 2b were more toxic than b or 1. Compound 1b was more toxic than 1 and b on MDA-MB231 (Triple Negative Breast Cancer Cells).
Figure 19:
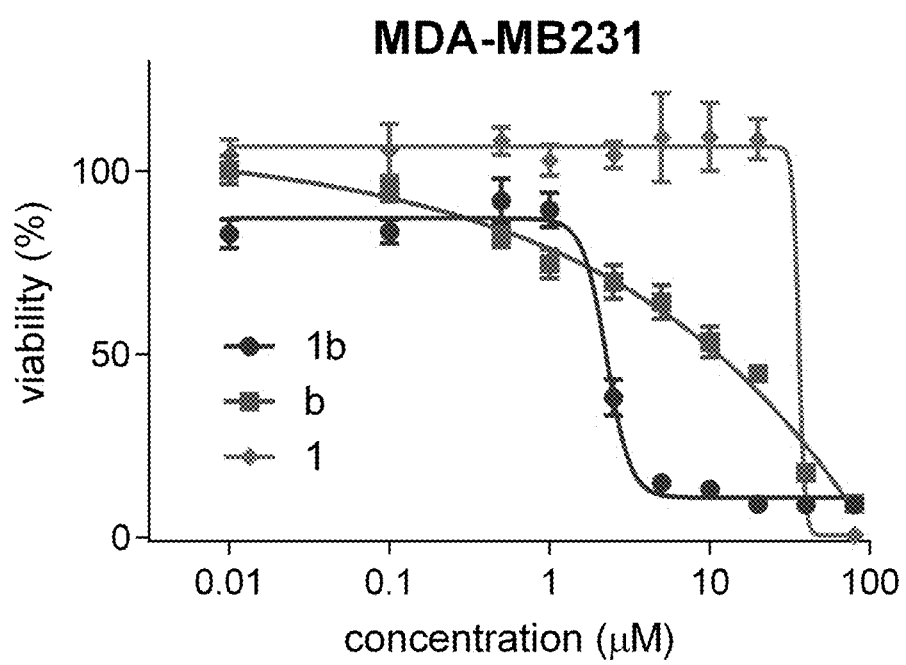
FIG. 19 shows cytotoxicity of 2b as compared to 1b, 1 and b on MBA-MB-231 (Breast Cancer). It was observed that 1b was more toxic than b or 1.
Figure 20:
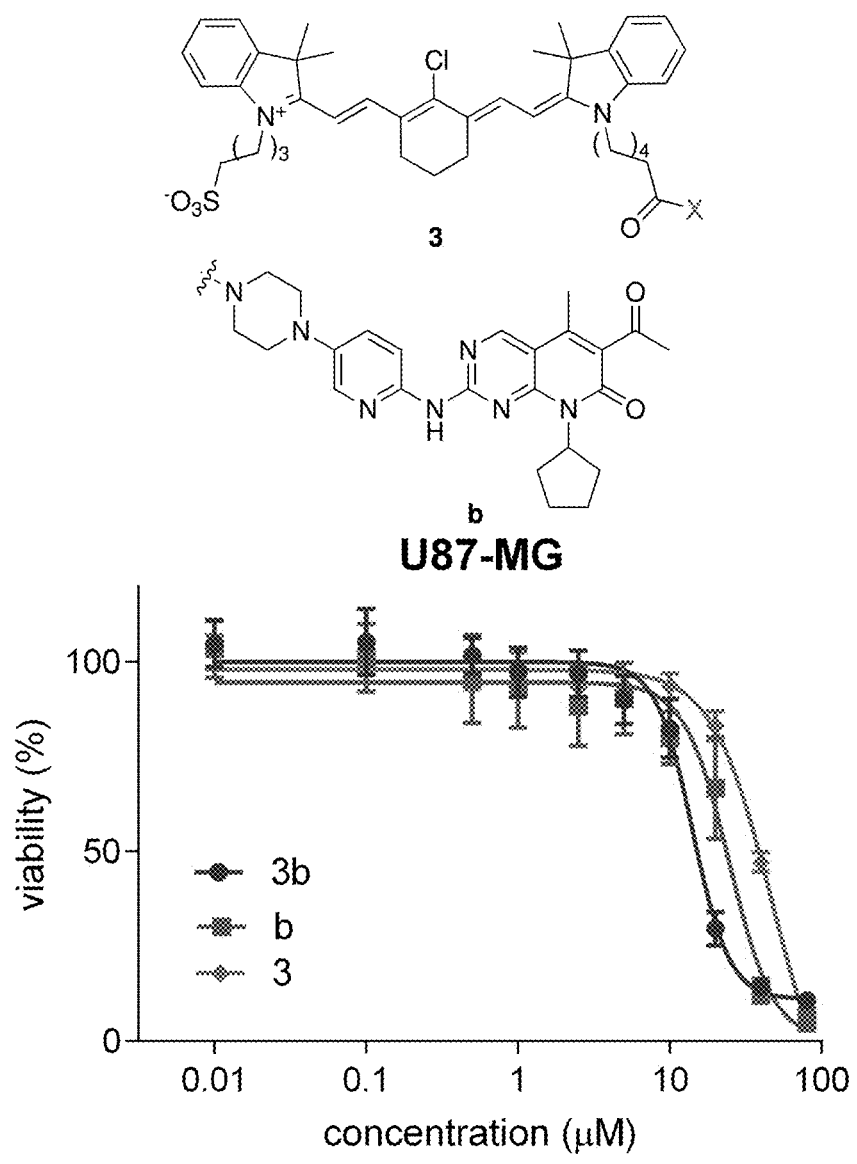
FIG. 20 shows cytotoxicity of 3b as compared to 3 and b on U87-MG. It was observed that 3b was more toxic than b or 3.
Figure 21:
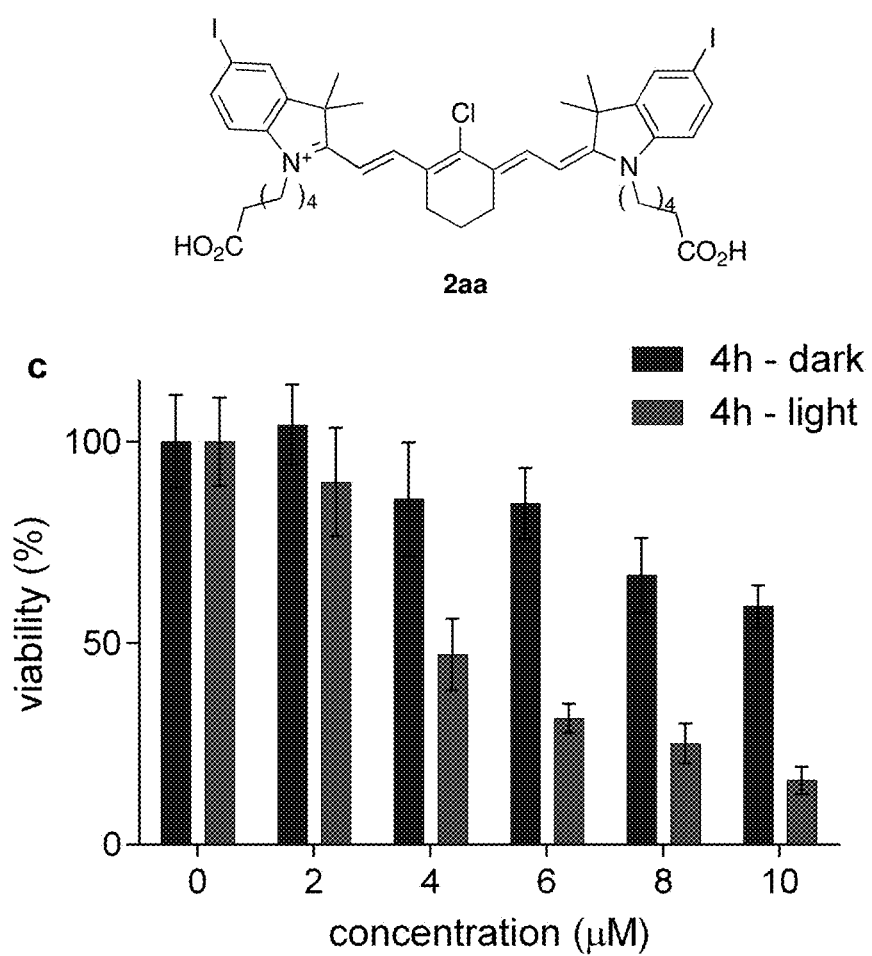
FIG. 21 shows light and dark toxicity of 2aa on U87-MG cells after 1, 2, 4, and 6 h of incubation at 10 mins irradiation. Light toxicity was more than light in every case, and 2-4 gave optimal difference; only data at 4 h is shown.
Figure 22:
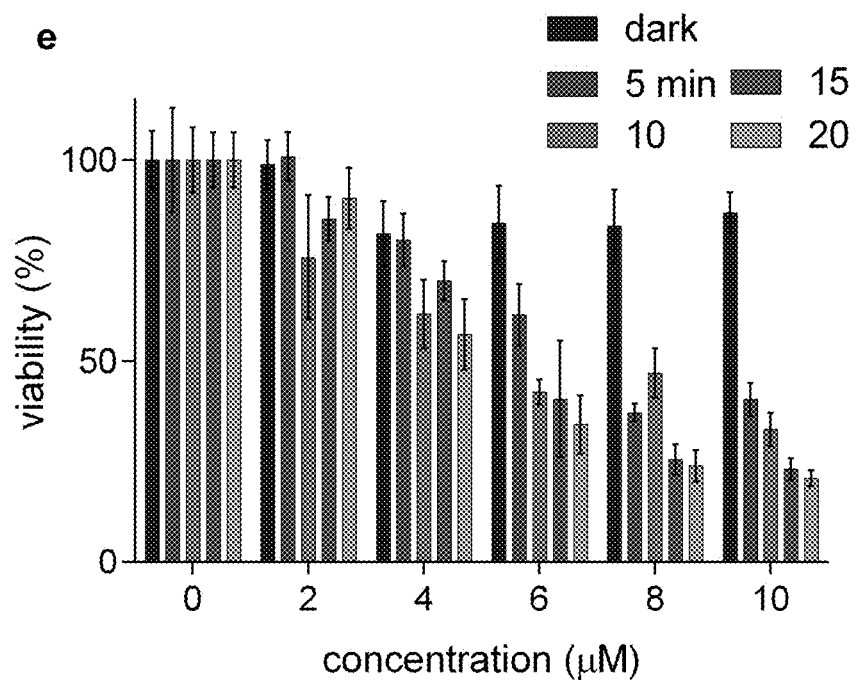
FIG. 22 shows light and dark toxicity of 2aa on U87-MG (Glioblatsoma) at 1 h of incubation with different irradiation times (5, 10, 15, 20 minutes). This data shows that 2aa kills the cells more in light than in dark.
Figure 23:
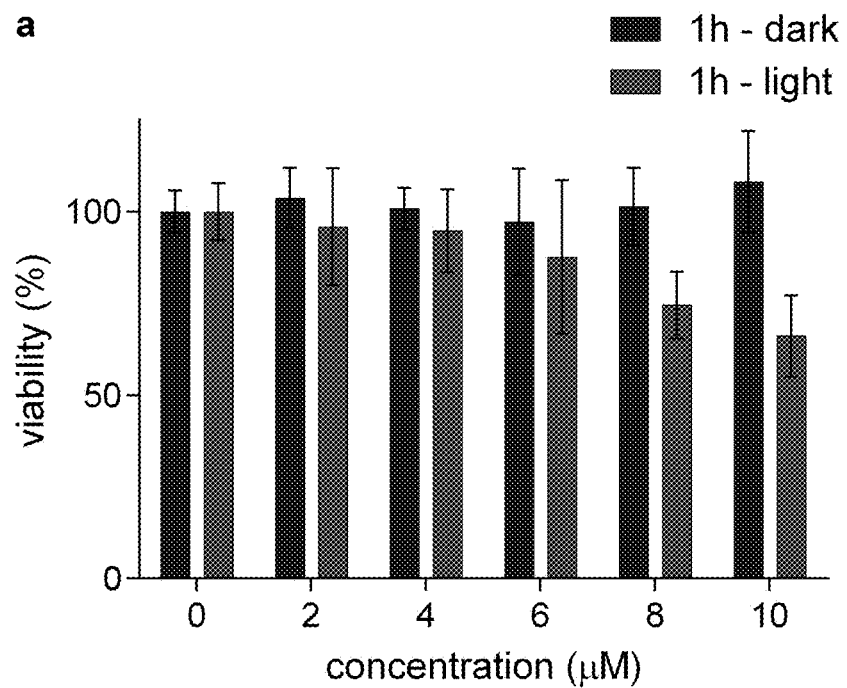
FIG. 23 shows light and dark toxicity of 2aa on HUVEC at 1 h incubation after at 10 minutes irradiation. HUVEC cells are non-carcinogentic, "normal" epitheliual cells. They do not have the OATP receptor overexpressed, and may not import albumin so readily. This data compares the phototoxic effect of 2aa on HUVEC (normal) cells at different incubation time at similar irradiation time. This data shows that 2aa does not significantly kill normal cells at different irradiation time.
Figure 26:
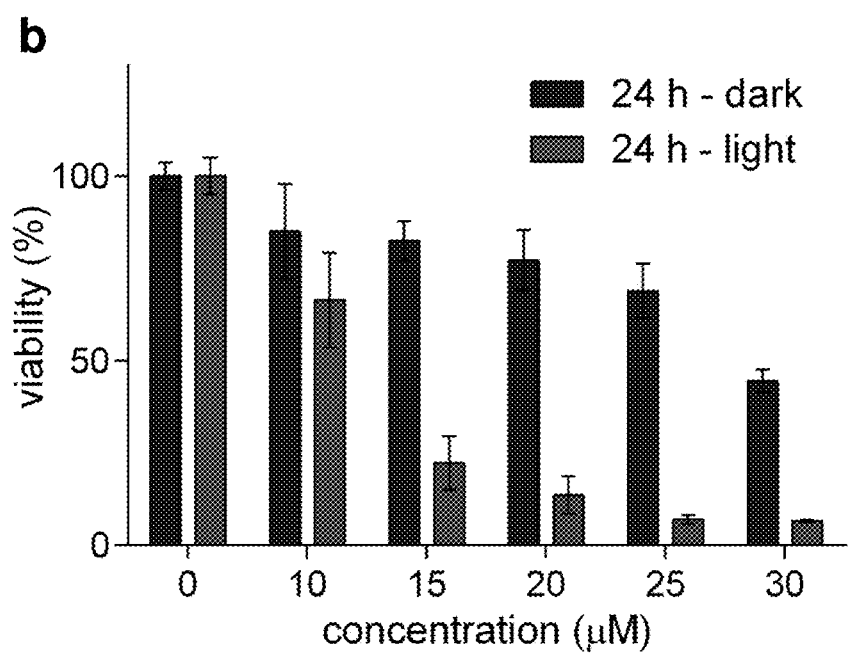
FIG. 26 shows light and dark toxicity of I2-1-NMe$_2$ on U87-MG (Glioblastoma) cells at different a, 6; b, 24 h at 20 mins irradiation. I2-1-NMe$_2$ showed was more toxic in light than in dark on U87-MG (Glioblastoma) cells.
Figure 27:
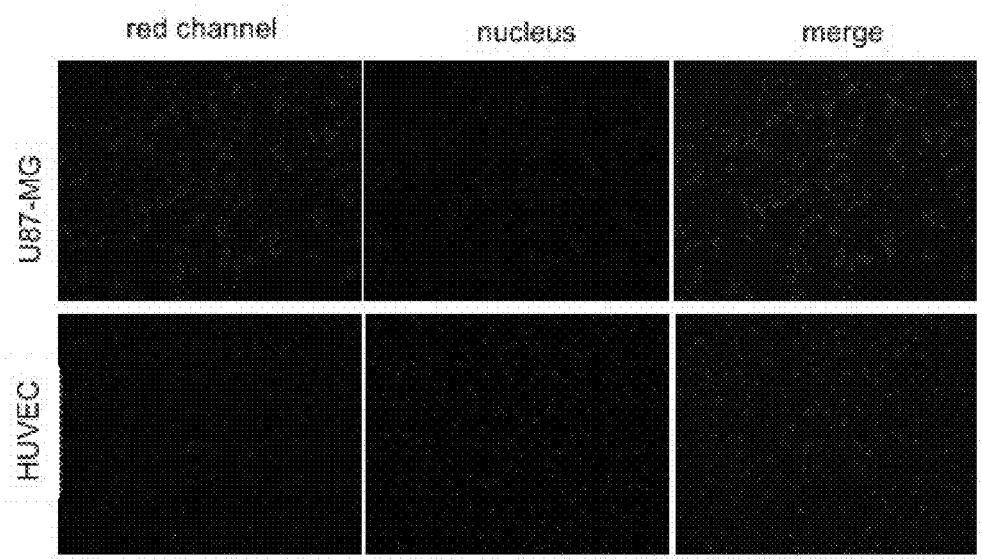
FIG. 27 shows 1a uptake by U87-MG (Glioblastoma) cells as compared to HUVEC (normal cells). It was found that 1a localizes more in U87-MG cells than HUVEC cells.
Figure 28:
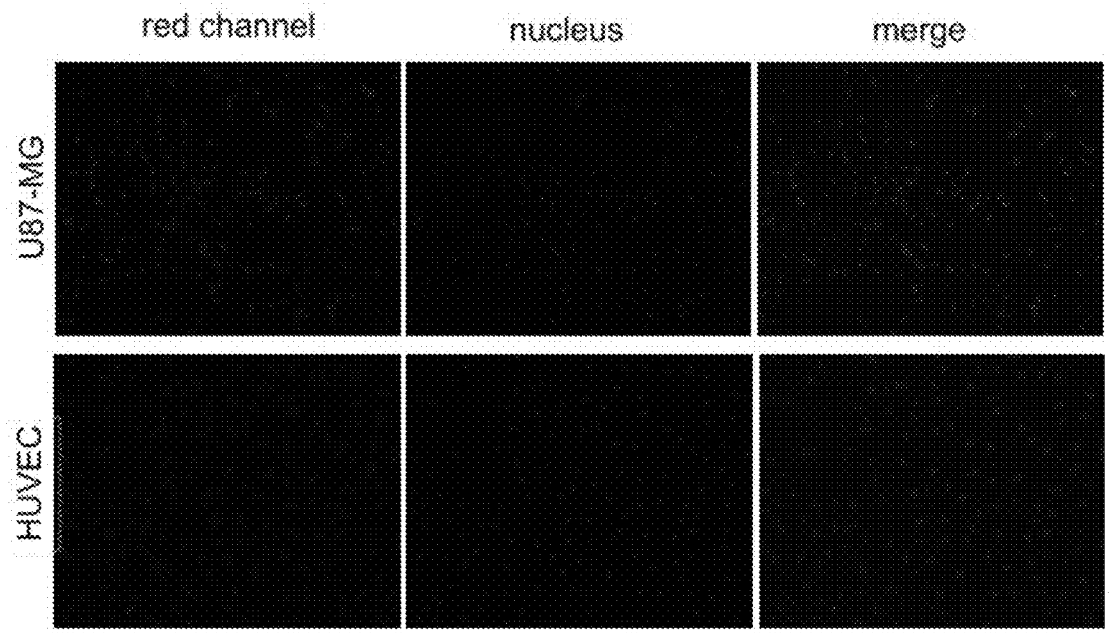
FIG. 28 shows 1b uptake by U87-MG (GBM cells) cells as compared to HUVEC (normal cells). It was found that 1b localizes more in U87-MG cells than HUVEC cells.
Figure 29A:
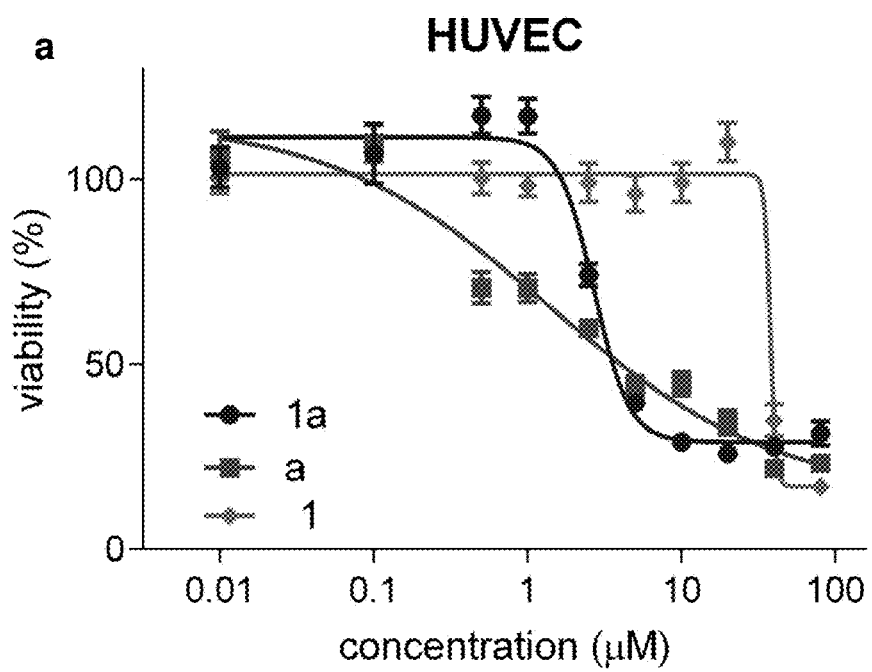
FIGS. 29A and 29B show cytotoxicity of a, 1a; b, 1b; on HUVEC (normal) cells. It was found that a, 1a and 1b had similar cytotoxicity as parent kinase inhibitor a and b.
Figure 29B:
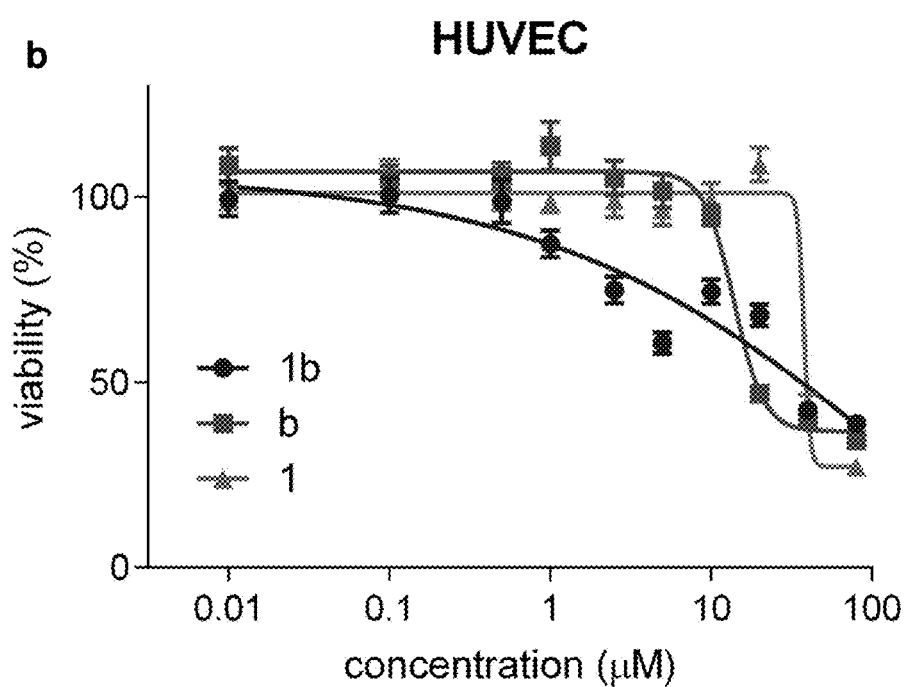
Figure 30B:
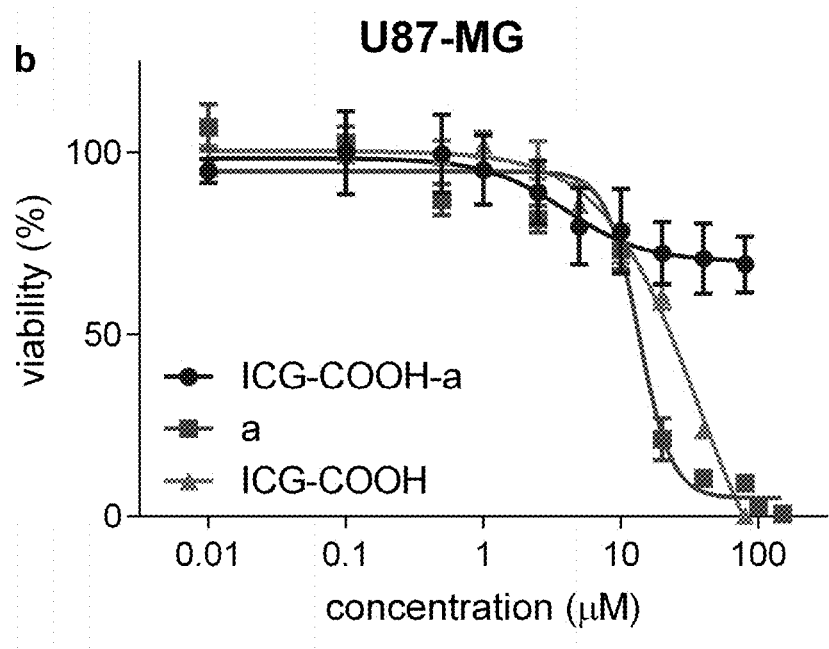
Figure 30C:
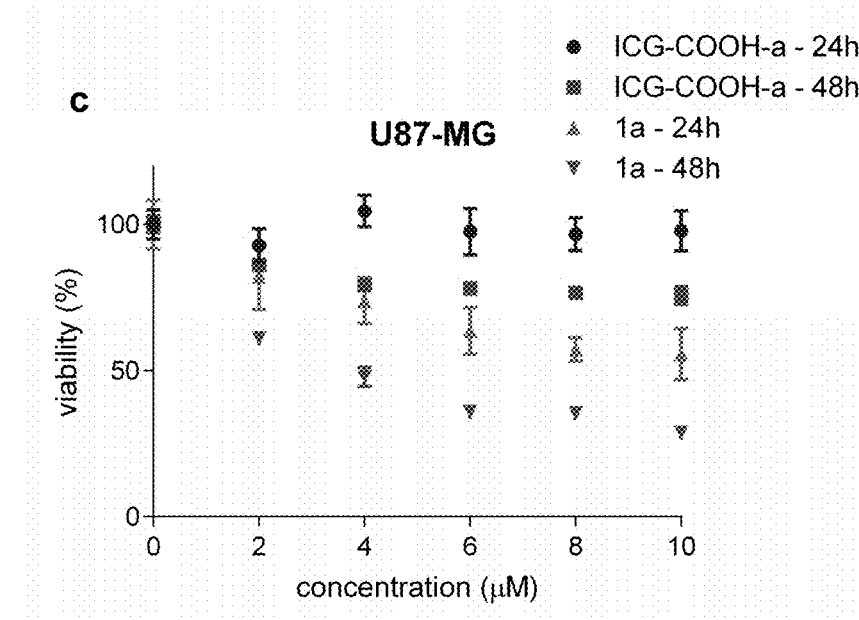
Figure 31A:
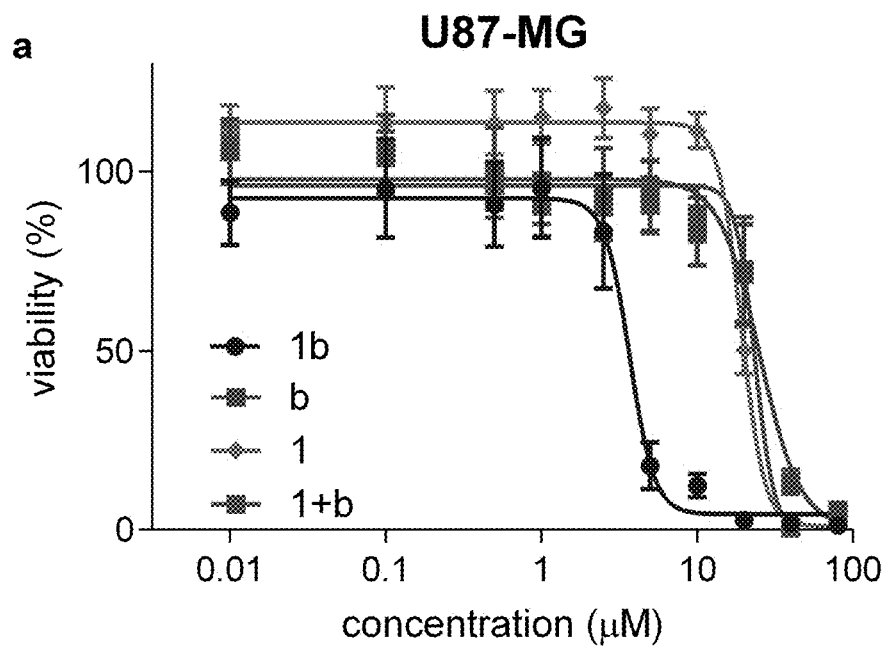
Figure 31B:
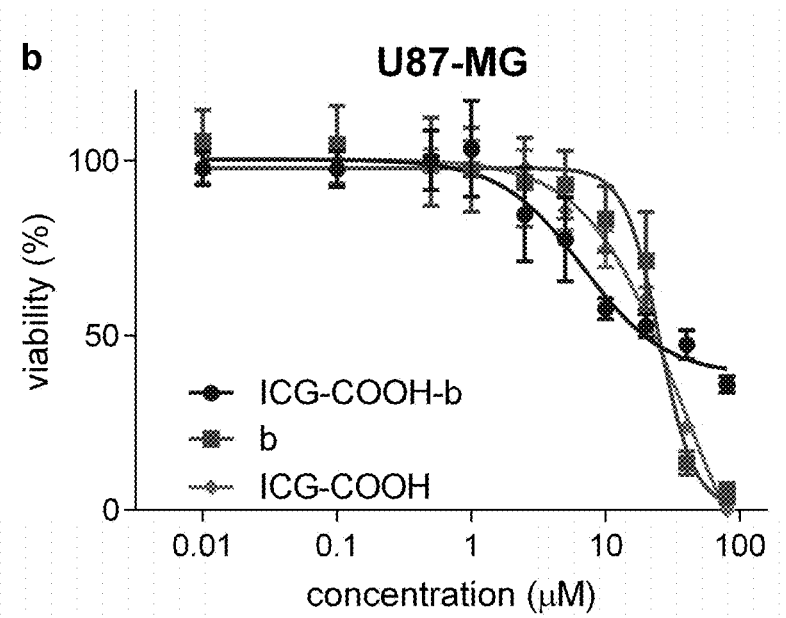
Figure 33A:
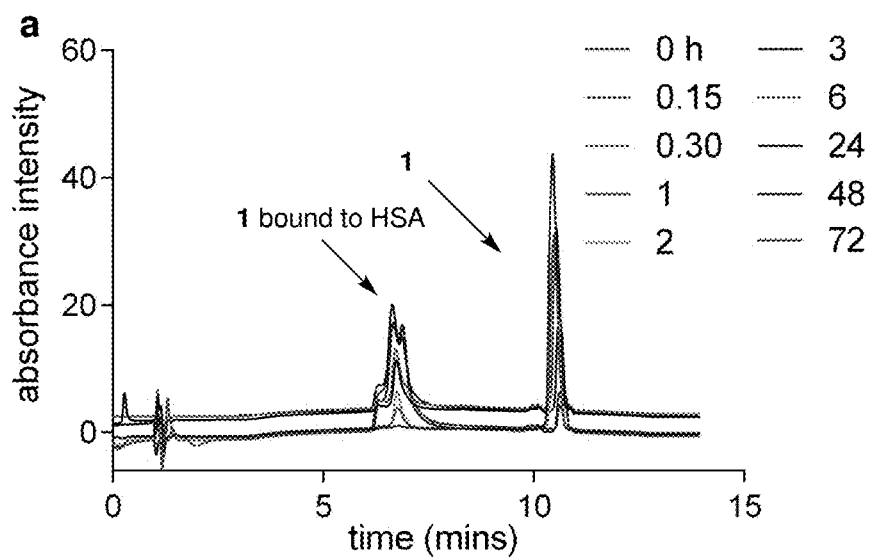
FIGS. 33A to 33D show kinetics of a, 1, c, 4, d, 5; e, 6 in 1 M HEPES buffer pH 7.4. 1 showed an increase in peak with HSA. The kinetics was examined on C, 18 column using Agilent 1200 series LC/MS at 600 nm. This data shows that meso position of 1 is essential for binding to HSA. HSA did not bind to cyanines when meso Cl was substituted to H (4), Me (5) or Ph (6).
Figure 33B:
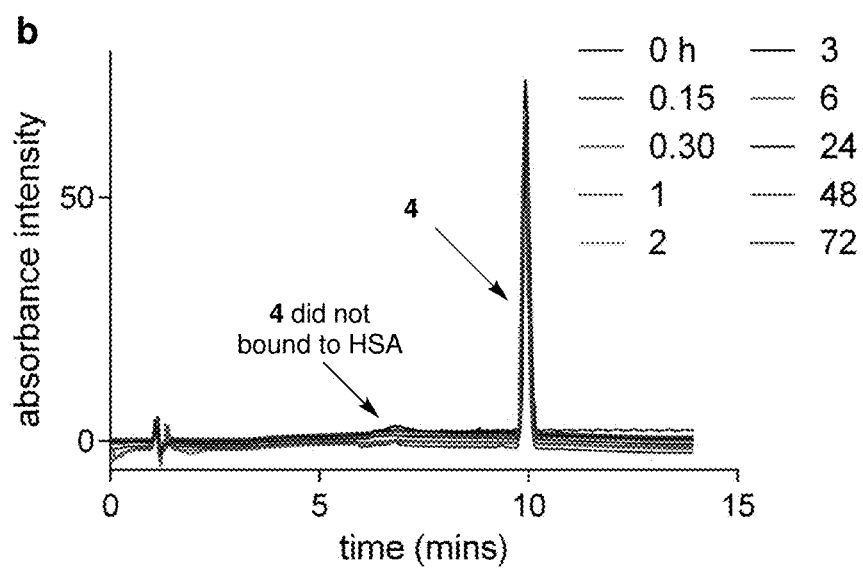
Figure 33C:
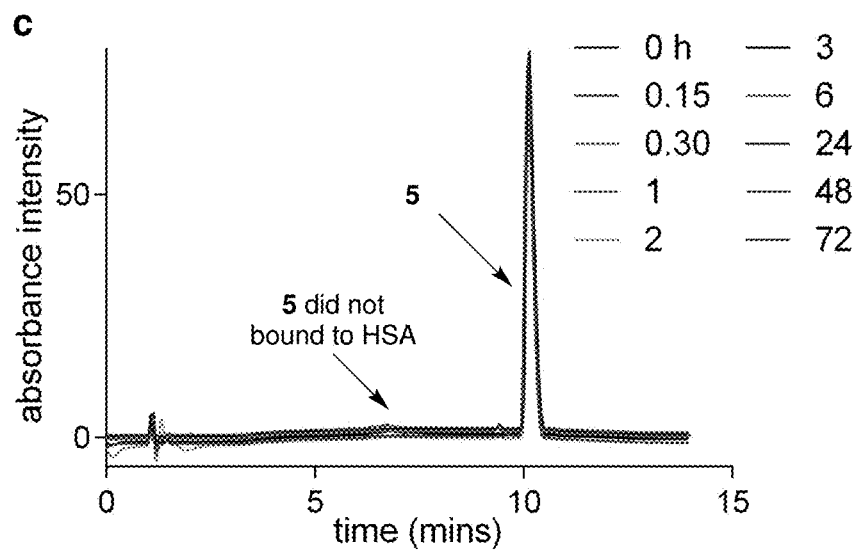
Figure 33D:
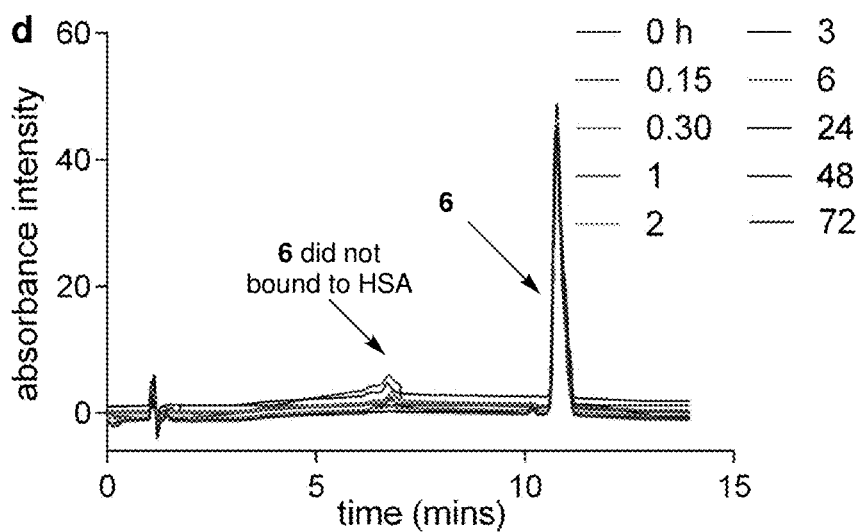
Figure 34A:
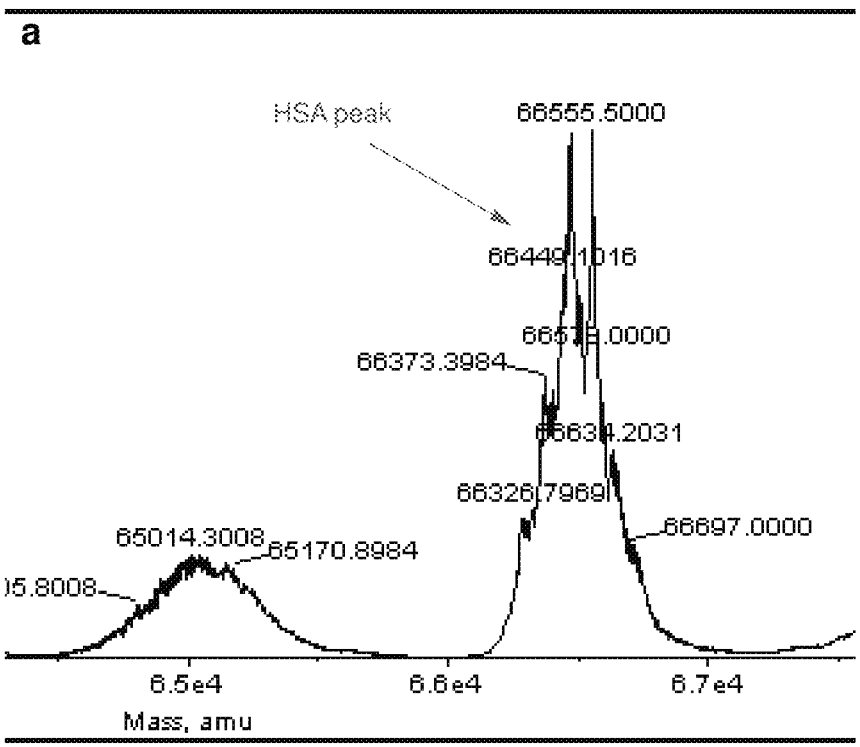
FIGS. 34A and 34B show mass spectra of a, free HSA and b, 1 bound to HSA. HSA: 1 (2.5:1); buffer 1 M HEPES. It shows that HSA is bound to 1.
Figure 34B:
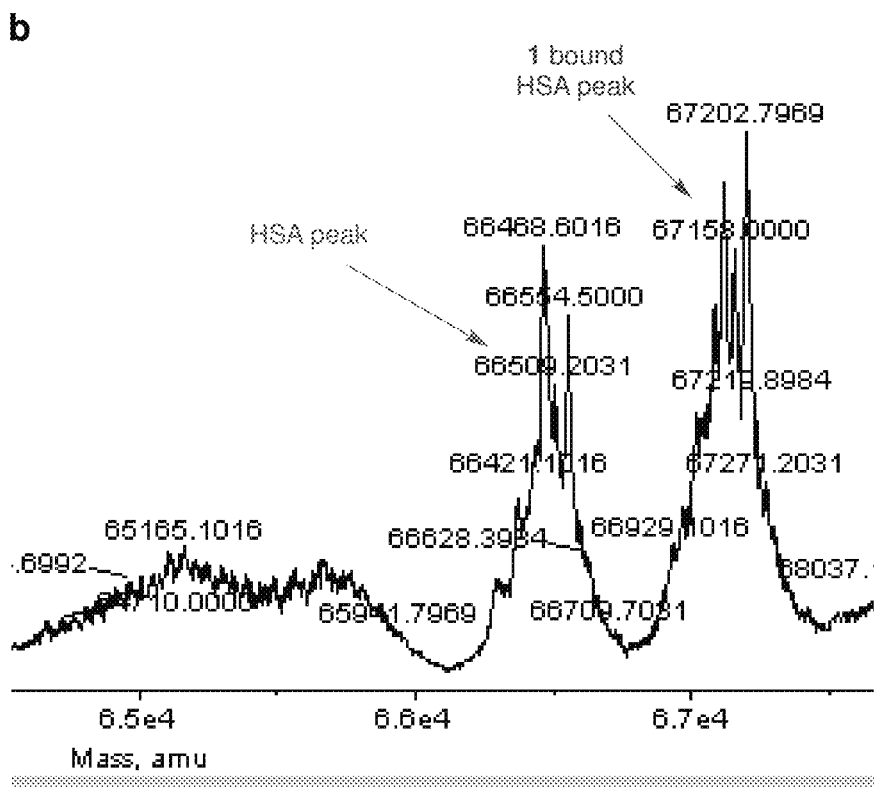
Figure 35A:
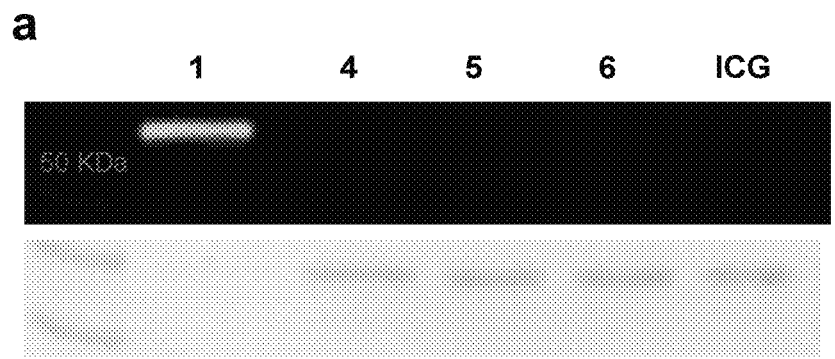
FIGS. 35A and 35B show NIR-fluorescent gel image (>800 nm) of a HSA (1 μM, 1 μg) incubated with different cyanines (10 μM) for 3 h in pH 7.4 50 mM HEPES buffer b HSA (15 μM, 1 μg) or thiol-blocked HSA (prior reacted with TECP followed by 6-maleimide hexanoic acid) (15 μM, 1 μg) treated with 1 (15 μM) in different incubation time. Figure a confirms that only 1-C; (with meso Cl) is bound to HSA but not 4, 5 and 6 (which do not have meso Cl). 1 binds to HSA at cysteine 34 position. In figure b shows confirmation by reducing all the cysteines by TCEP and then blocking cysteines by 6-maleimide hexanoic acid. HSA which was capped by 6-maleimide hexanoic acid did not bind to 1-Cl.
Figure 35B:
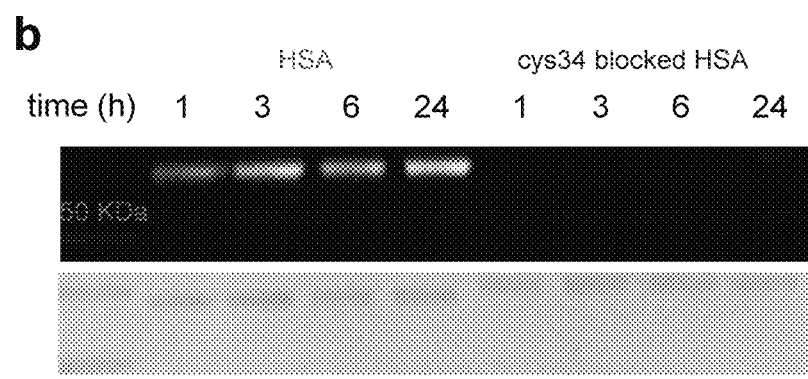

FIG. 15 shows new PDT cyanine dyes. FIG. 16 shows compounds 2 produce singlet oxygen when illuminated in the air with light of 780 nm.

Differences in the characteristics of the compounds became more prevalent in photocytotoxicity experiments. Thus, HEG2 cells were incubated with compounds 2 for 1 h, washed, then illuminated in fresh media at 780 nm (3.98 mW/cm$^2$ LED) for 10 min, incubated for 24 h, then tested of viability (Alamar Blue). FIGS. 17A to 17F are organized to show data for compounds 2 organized from least to most photocytotoxic. All the compounds were significantly more photocytotoxic than dark controls in which the illumination step was omitted. The dipropyl compound 2cc, was less photocytotoxic than the known, disulfonic acid, sensitizer 2bb, but all the others were more cytotoxic. More than 50% of the cells remained in the experiments featuring treatment with 2bb at 10 μM, but under the same conditions 2ac (sulfonic acid and propyl N-substituents) killed almost all of the cells. At 6 μM, 2ac killed more than half the cells in this assay.

Example 15. Synthesis Scheme for 2Aa-b

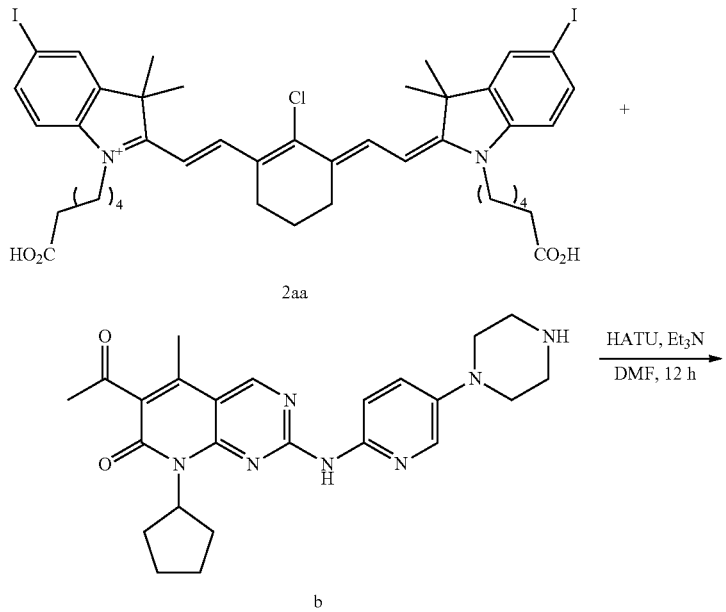

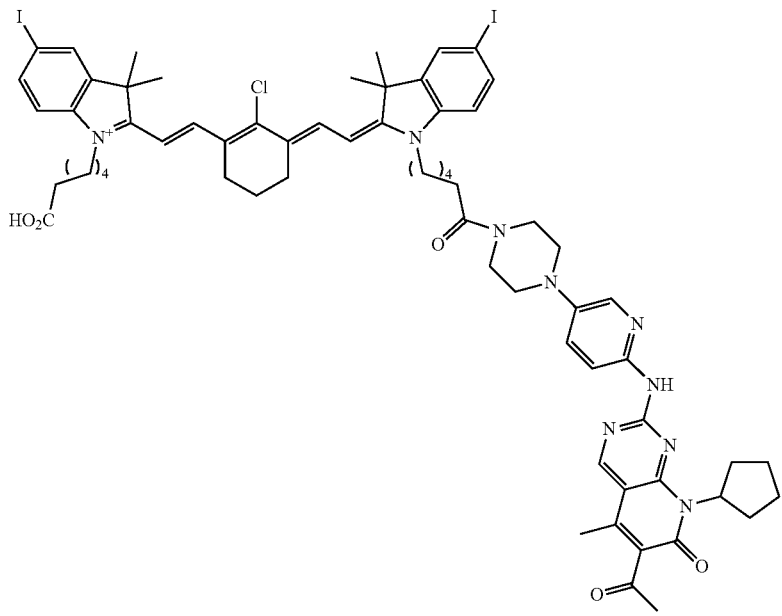

2aa-b

Iodinated cyanine dye 2aa (200.0 mg, 0.21 mmol), triethylamine (48.50 uL, 0.34 mmol) and HATU (81.06 mg, 0.21 mmol) were added in 2 mL DMF and stirred for 15 mins followed by b (93.87 mg, 0.21 mmol) was added afterwards and stirred for 12 h under argon balloon. Solvent was removed and the crude was purified by reverse phase column on prep-HPLC {50% MeCN/50% H$_2$O-90% MeCN/10% H$_2$O (containing 0.1% TFA) in 20 mins} to get the desired product as amorphous green solid (32 mg, 9.6%).

$^1$H NMR (400 MHz, MeOD) δ 9.02 (s, 1H), 8.41 (d, J=17.3 Hz, 1H), 8.37 (d, J=14.1 Hz, 1H), 8.02 (dd, J=9.5, 2.7 Hz, 1H), 7.95-7.85 (m, 2H), 7.85 (s, 1H), 7.78 (dd, J=8.4, 1.6 Hz, 1H), 7.73-7.65 (m, 2H), 7.19 (d, J=8.4 Hz, 1H), 7.08 (d, J=8.4 Hz, 1H), 6.34 (d, J=14.1 Hz, 1H), 6.22 (d, J=14.1 Hz, 1H), 6.05-5.87 (m, 1H), 4.17 (dt, J=14.8, 7.1 Hz, 4H), 3.81-3.64 (m, 4H), 3.25 (dd, J=9.0, 4.9 Hz, 3H), 2.73 (dt, J=16.5, 5.9 Hz, 3H), 2.57-2.44 (m, 5H), 2.42 (s, 2H), 2.32 (dd, J=13.9, 6.7 Hz, 4H), 2.10 (dd, J=8.0, 5.5 Hz, 2H), 1.99-1.79 (m, 7H), 1.75 (s, 5H), 1.73 (d, J=6.9 Hz, 3H), 1.70 (s, 6H), 1.68 (d, J=7.6 Hz, 1H), 1.49 (dd, J=15.1, 7.4 Hz, 3H).

$^{13}$C NMR (101 MHz, MeOD) δ 202.54, 175.75, 172.52, 172.42, 171.96, 161.17, 157.16, 155.88, 155.66, 150.15, 144.30, 144.08, 143.61, 143.44, 143.12, 143.04, 142.12, 141.96, 141.69, 137.59, 137.50, 132.26, 131.44, 131.37, 127.38, 127.35, 115.96, 112.98, 112.67, 109.66, 101.53, 101.13, 88.32, 88.16, 54.11, 49.27, 49.13, 44.89, 43.79, 40.92, 33.15, 31.73, 30.12, 27.69, 26.83, 26.81, 26.51, 25.90, 25.33, 24.60, 24.19, 20.66, 12.82.

Example 16. Synthesis Scheme for 1-NMe$_2$-b

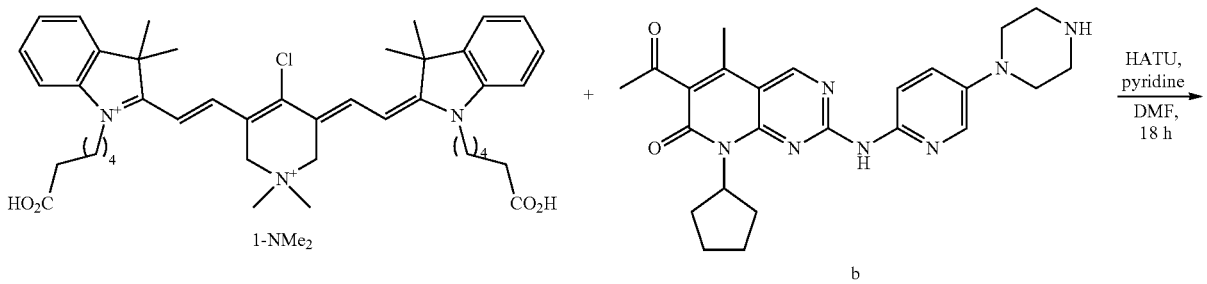

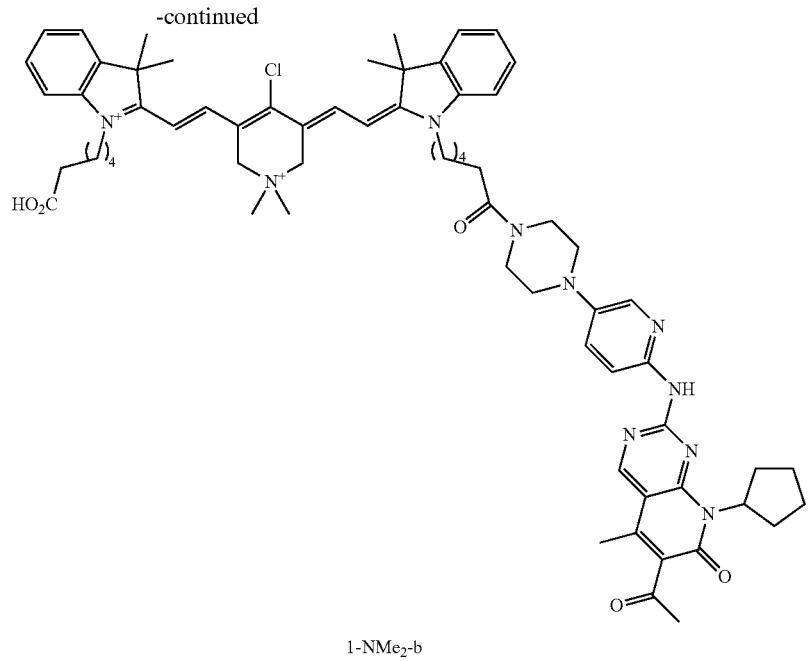

1-NMe₂-b

Compound 1-NMe₂ (100.0 mg, 0.14 mmol), pyridine (11.30 uL, 0.14 mmol) and HATU (50.0 mg, 0.14 mmol) were added in 5 mL DMF and stirred for 15 mins followed by b (62 mg, 0.14 mmol) was added afterwards and stirred for 18 h under argon balloon. Solvent was removed and the crude was purified by reverse phase column on prep-HPLC preparative reverse-phase HPLC (50-70% CH₃CN/H₂O containing 0.1% TFA) in 20 min to get the desired product as amorphous green solid (19 mg, 12%).

$^1$H NMR (400 MHz, MeOD) δ 9.11 (s, 1H), 8.47 (dd, J=14.8, 6.4 Hz, 2H), 8.17 (d, J=9.5 Hz, 1H), 7.90 (s, 1H), 7.66-7.48 (m, 6H), 7.48-7.35 (m, 2H), 6.32 (t, J=14.0 Hz 2H), 6.06-5.97 (m, 1H), 4.69 (d, J=5.0 Hz, 4H), 4.32 (dd, J=17.3, 7.8 Hz, 4H), 3.78 (s, 4H), 3.42 (s, 6H), 3.28 (s, 4H), 2.52 (s, 5H), 2.44 (s, 3H), 2.29-2.25 (m, 4H), 2.13 (s, 2H), 2.00-1.93 (m, 6H), 1.80 (s, 12H), 1.79-1.70 (m, 6H), 1.56-1.53 (m, 4H).

Example 17. Experimental Procedures and Characterization for New Non-Iodinated Compounds Prepared From QCy

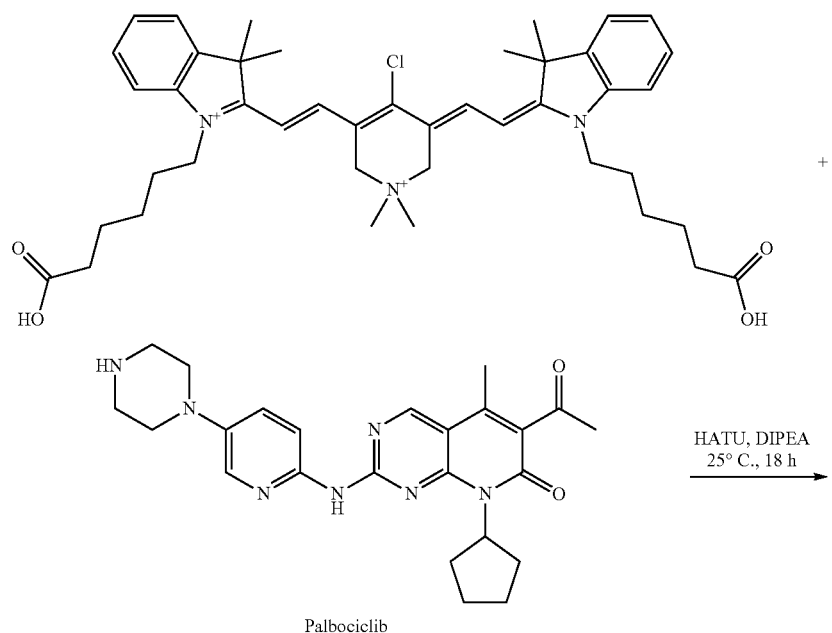

Palbociclib

HATU, DIPEA
25° C., 18 h

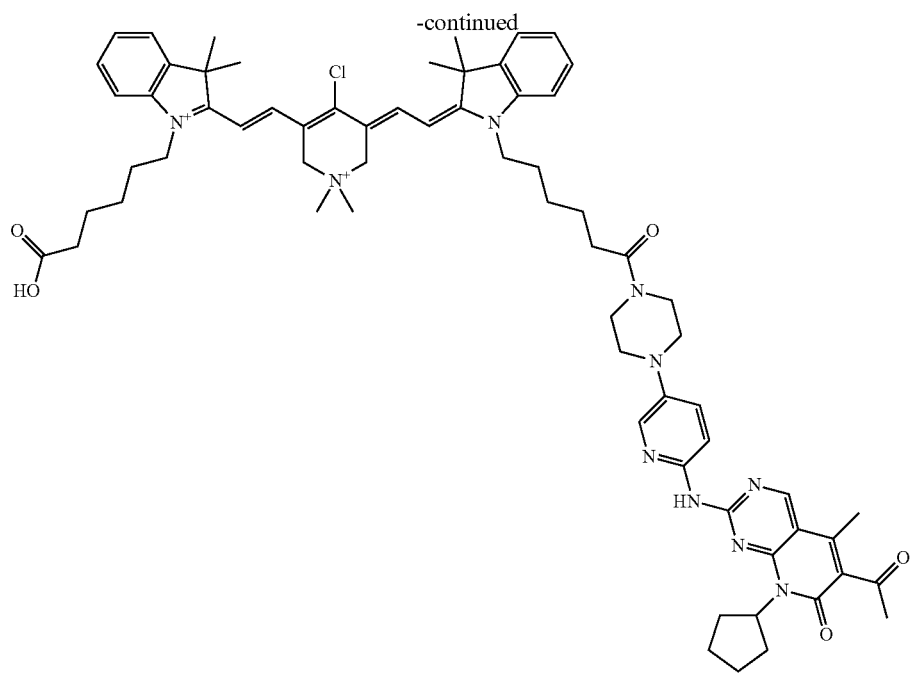

QCy (100.0 mg, 0.14 mmol), pyridine (11.30 uL, 0.14 mmol) and HATU (50.0 mg, 0.14 mmol) were added in 5 mL DMF and stirred for 15 mins followed by Palbociclib (62 mg, 0.14 mmol) was added afterwards and stirred for 18 h under argon balloon. Solvent was removed and the crude was purified by reverse phase column on prep-HPLC preparative reverse-phase HPLC (50-70% CH$_3$CN/H$_2$O containing 0.1% TFA) in 20 min to get the desired product as amorphous green solid (19 mg, 12%).

$^1$H NMR (400 MHz, MeOD) δ 9.11 (s, 1H), 8.47 (dd, J=14.8, 6.4 Hz, 2H), 8.17 (d, J=9.5 Hz, 1H), 7.90 (s, 1H), 7.66-7.48 (m, 6H), 7.48-7.35 (m, 2H), 6.32 (t, J=14.0 Hz 2H), 6.06-5.97 (m, 1H), 4.69 (d, J=5.0 Hz, 4H), 4.32 (dd, J=17.3, 7.8 Hz, 4H), 3.78 (s, 4H), 3.42 (s, 6H), 3.28 (s, 4H), 2.52 (s, 5H), 2.44 (s, 3H), 2.29-2.25 (m, 4H), 2.13 (s, 2H), 2.00-1.93 (m, 6H), 1.80 (s, 12H), 1.79-1.70 (m, 6H), 1.56-1.53 (m, 4H).

HRMS (ESI) m/z calcd for C$_{67}$H$_{83}$C$_1$N$_{10}$O$_5$$^{2+}$ calculated: 571.3113; found 571.3112.

Example 18. QCy-DasNH

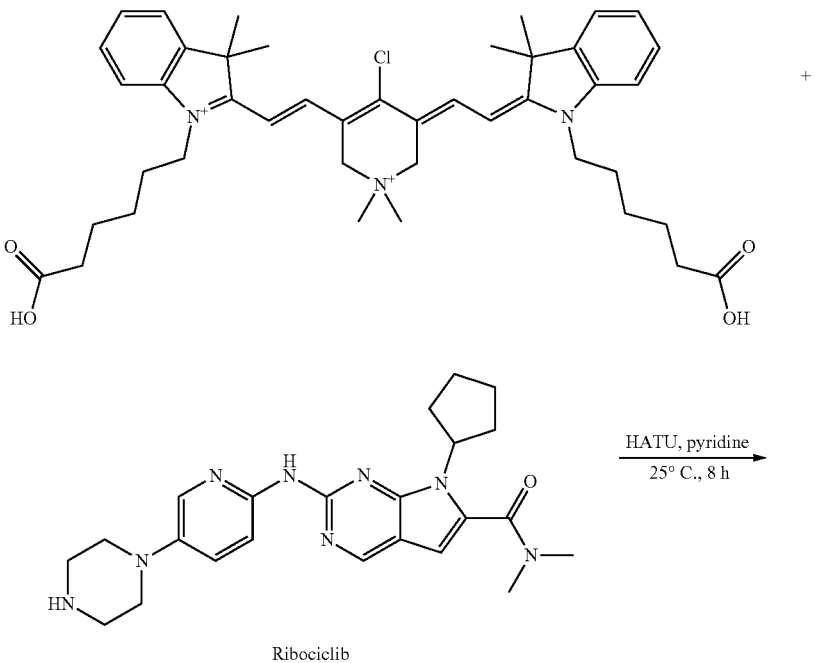

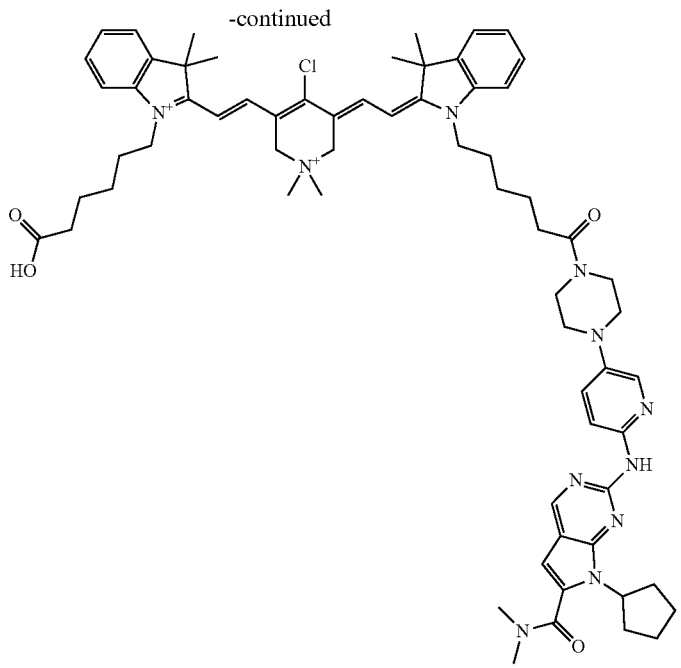

QCy (50.0 mg, 0.07 mmol), pyridine (6.00 uL, 0.07 mmol) and HATU (26.0 mg, 0.07 mmol) were added in 5 mL DMF and stirred for 15 mins followed by Ribociclib (35 mg, 0.08 mmol) was added afterwards and stirred for 8 under argon balloon. Solvent was removed and the crude was purified by reverse phase column on prep-HPLC preparative reverse-phase HPLC (40-70% $CH_3CN/H_2O$ containing 0.1% TFA) in 20 min to get the desired product as amorphous green solid (5 mg, 6%).

$^1$H NMR (400 MHz, MeOD) δ 8.97 (s, 1H), 8.47 (dd, J=14.8, 5.0 Hz, 2H), 8.06 (dd, J=9.5, 2.8 Hz, 1H), 7.86 (d, J=2.8 Hz, 1H), 7.63-7.60 (m, 2H), 7.53-7.38 (m, 7H), 6.81 (s, 1H), 6.33 (t, J=13.1 Hz, 2H), 4.71 (d, J=6.7 Hz, 4H), 4.36-4.29 (m, 4H), 3.78 (t, J=4.5 Hz 4H), 3.43 (s, 6H), 3.28-3.17 (m, 11H), 2.54-2.45 (m, 4H), 2.36 (t, J=7.2 Hz, 2H), 2.12 (brs, 4H), 2.01-1.92 (m, 4H), 1.78 (s, 12H), 1.76-1.60 (m, 6H), 1.59-1.53 (s, 4H)

HRMS (ESI) m/z calcd for $C_{66}H_{84}ClN_{11}O_4^{2+}$ calculated: 564.8193; found 564.8197.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the invention encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A conjugate of Formula (Ia):

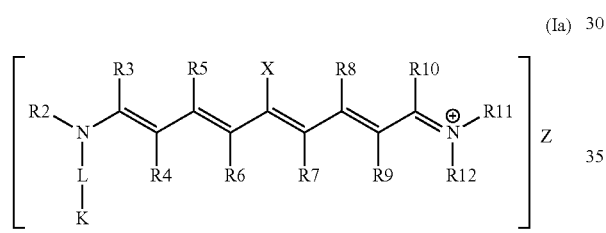

(Ia)

or a pharmaceutically acceptable salt thereof, wherein:
L is selected from optionally substituted $C_{1-10}$ alkyl, and optionally substituted heteroC$_{1-10}$ alkyl;
K is selected from:

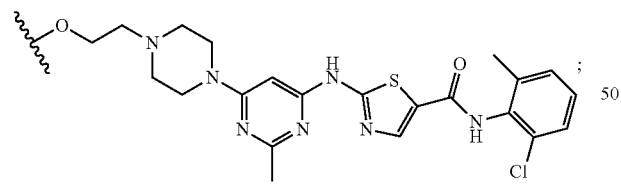

a

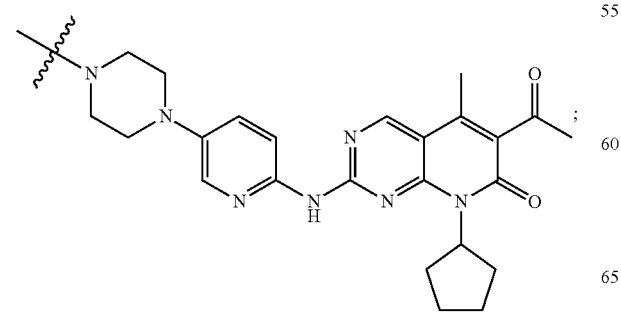

b

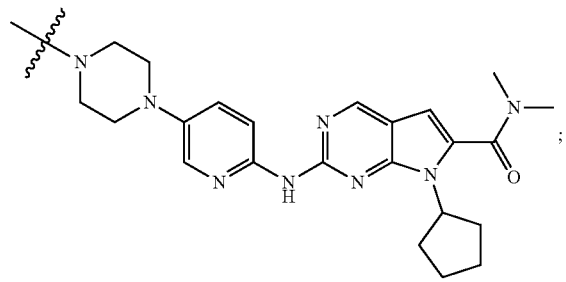

c

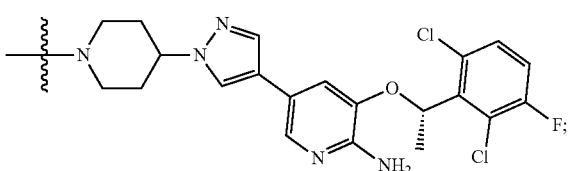

d and

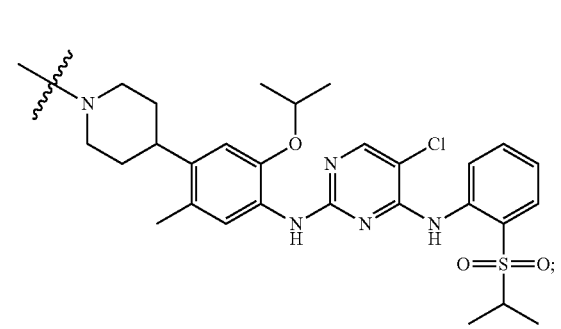

e each — is a covalent bond;
X is halogen;
Z is one or more anions to achieve electrical neutrality;
R2 and R3 combine to form a five- or six-membered ring, wherein the five- or six-membered ring is optionally substituted and optionally fused to an aryl or heteroaryl ring;
R4 and R5 independently are hydrogen, optionally substituted aliphatic, optionally substituted heteroaliphatic, optionally substituted aryl, or optionally substituted heteroaryl;
R6 and R7 are independently hydrogen, or aliphatic, or combine to form a five- or six-membered carbocyclic or heterocyclic ring;
R8 and R9 independently are hydrogen, optionally substituted aliphatic, optionally substituted heteroaliphatic, optionally substituted aryl, or optionally substituted heteroaryl;
R10 and R11 combine to form a five- or six-membered ring, wherein the five- or six-membered ring is optionally substituted and optionally fused to an aryl or heteroaryl ring; and R12 is optionally substituted aliphatic, or optionally substituted heteroaliphatic.

2. A method of inhibiting the proliferation of a cancer cell, comprising contacting the cell with a conjugate of claim 1.

3. A method of treating cancer in a subject in need thereof, comprising administering a conjugate of claim 1.

4. The conjugate of claim 1, wherein Formula (Ia) is of Formula (Ib):

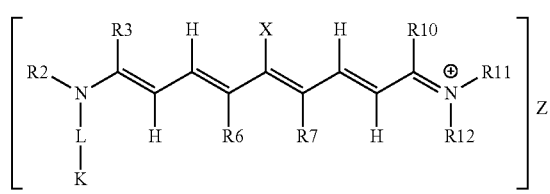

(Ib)

or a pharmaceutically acceptable salt thereof.

5. The conjugate of claim 4, wherein Formula (Ib) is of Formula (Ic):

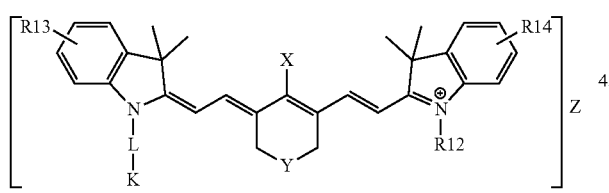

(Ic)

or a pharmaceutically acceptable salt thereof, wherein:
R13 and R14 independently are hydrogen, halogen, cyano, nitro, optionally substituted amino, optionally substituted alkyl, or optionally substituted heteroalkyl; and
Y is C(R15)(R16) or N(R17)(R18); wherein:
R15 and R16 independently are hydrogen, alkyl, heteroalkyl, aryl or heteroaryl; and
R17 and R18 independently are alkyl, heteroalkyl, aryl or heteroaryl.

6. The conjugate of claim 5, wherein Formula (Ic) is of Formula (Id):

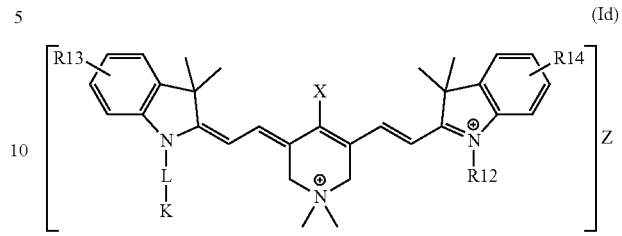

(Id)

or a pharmaceutically acceptable salt thereof.

7. The conjugate of claim 5, wherein Formula (Ic) is of Formula (Ie):

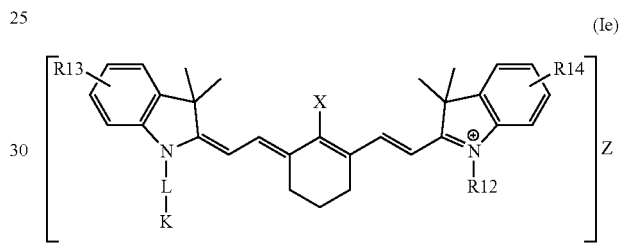

(Ie)

or a pharmaceutically acceptable salt thereof.

8. The conjugate of claim 7, wherein Formula (Ie) is of Formula (If):

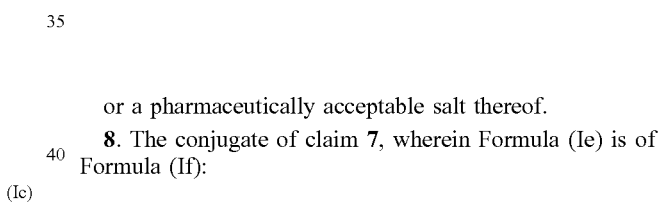

(If)

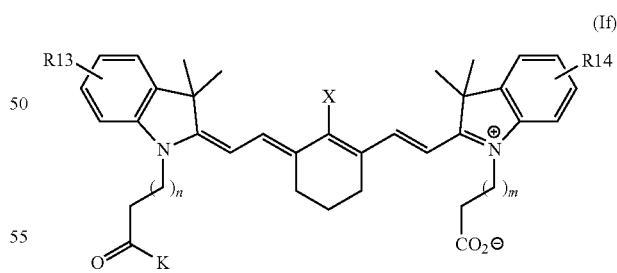

or a pharmaceutically acceptable salt thereof, wherein:
m and n independently are 2-20.

9. The conjugate of claim 1, wherein X is chlorine.

10. The conjugate of claim 5, wherein R13 and R14 are hydrogen; or wherein R13 and R14 are halogen.

11. The conjugate of claim 1, having the structure selected of:
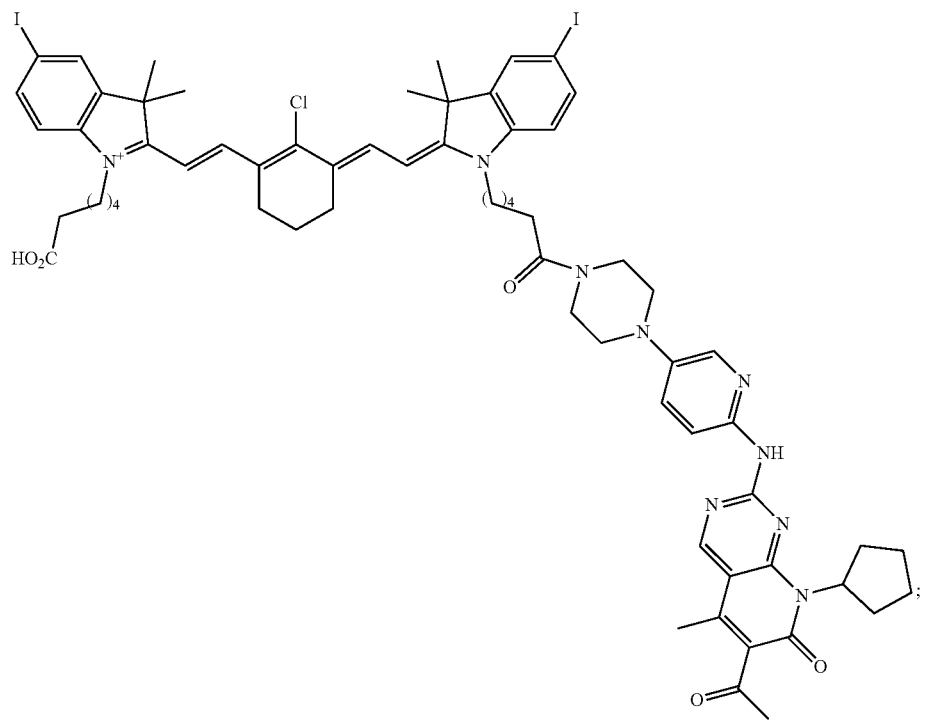
2aa-b
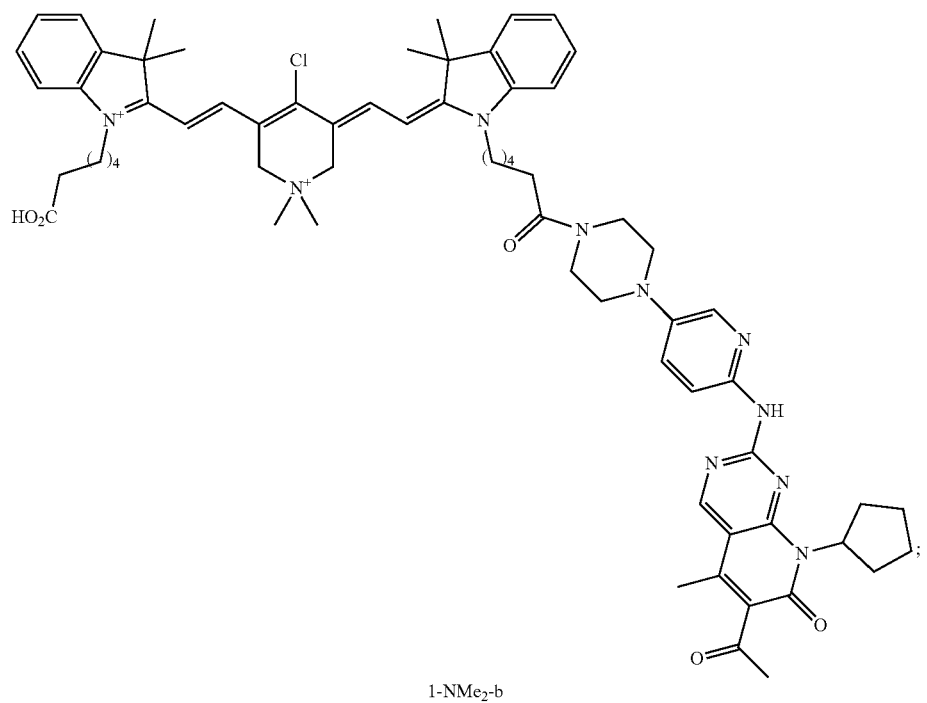
1-NMe$_2$-b -continued
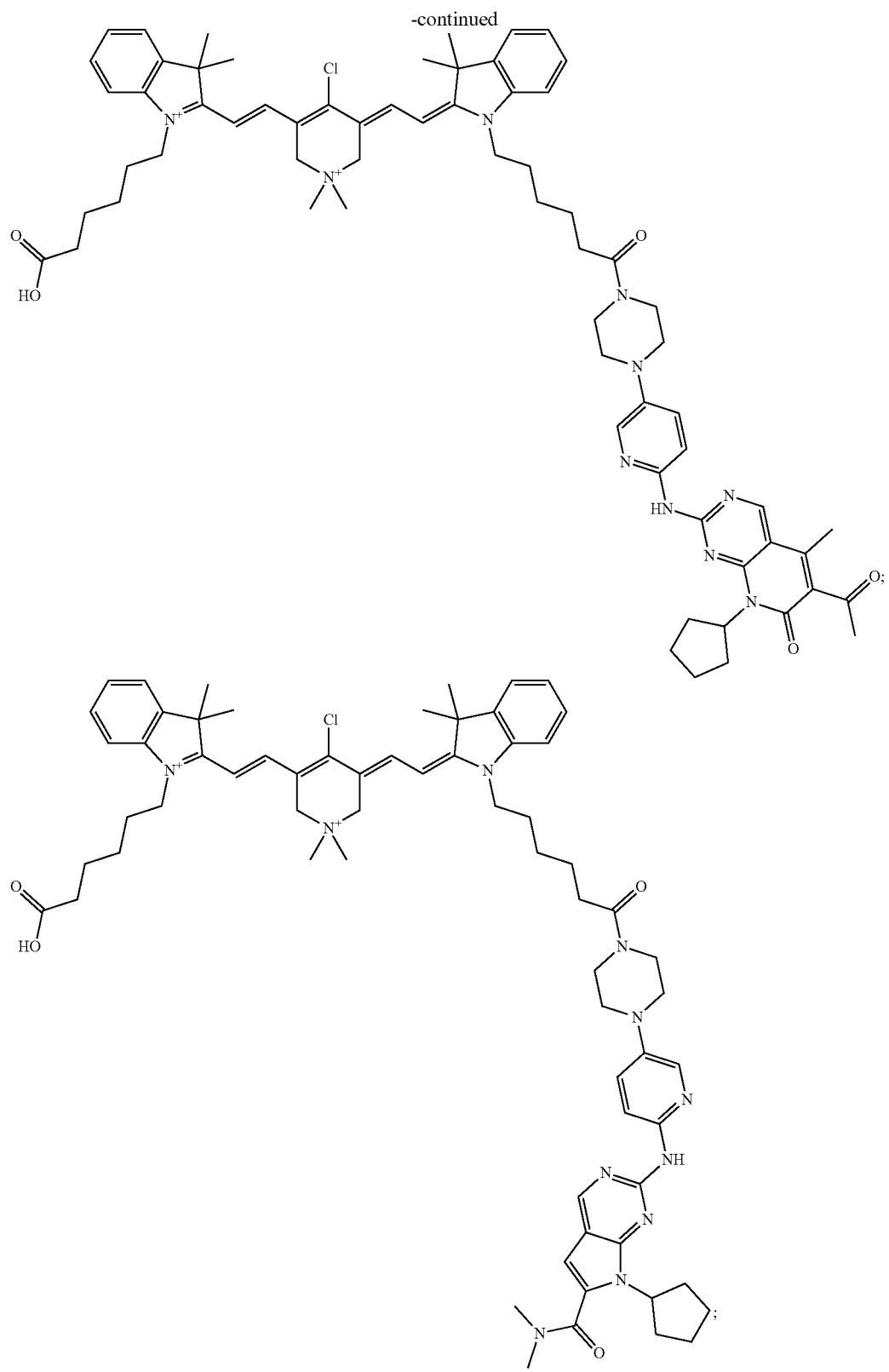
or a pharmaceutically acceptable salt thereof.
* * * * *